United States Patent
O'Sullivan et al.

(10) Patent No.: US 10,499,642 B2
(45) Date of Patent: Dec. 10, 2019

(54) ISOXAZOLINE-SUBSTITUTED BENZAMIDES AND ANALOGUES AS INSECTICIDES

(71) Applicant: SYNGENTA PARTICIPATIONS AG, Basel (CH)

(72) Inventors: Anthony Cornelius O'Sullivan, Stein (CH); Myriem El Qacemi, Stein (CH); Jérôme Yves Cassayre, Münchwilen (CH); Thomas Pitterna, Stein (CH); André Stoller, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/762,498

(22) PCT Filed: Sep. 22, 2016

(86) PCT No.: PCT/EP2016/072587
§ 371 (c)(1),
(2) Date: Mar. 22, 2018

(87) PCT Pub. No.: WO2017/050921
PCT Pub. Date: Mar. 30, 2017

(65) Prior Publication Data
US 2018/0271096 A1    Sep. 27, 2018

(30) Foreign Application Priority Data

Sep. 23, 2015 (EP) .................... 15186538

(51) Int. Cl.
| | | |
|---|---|---|
| *A01N 43/80* | (2006.01) | |
| *C07D 413/14* | (2006.01) | |
| *C07D 261/04* | (2006.01) | |
| *C07D 413/12* | (2006.01) | |

(52) U.S. Cl.
CPC ........... *A01N 43/80* (2013.01); *C07D 261/04* (2013.01); *C07D 413/12* (2013.01)

(58) Field of Classification Search
CPC .. C07D 413/14; C07D 413/12; C07D 261/04; A01N 43/80
See application file for complete search history.

(56) References Cited

U.S. PATENT DOCUMENTS

| | | |
|---|---|---|
| 2007/0066617 A1 | 3/2007 | Mita et al. |
| 2011/0144334 A1 | 3/2011 | Mita et al. |
| 2013/0095126 A1* | 4/2013 | Perret .................... A01N 43/80 424/184.1 |

FOREIGN PATENT DOCUMENTS

| | | |
|---|---|---|
| WO | 2007/089634 A2 | 8/2007 |
| WO | 2011/067272 A1 | 6/2011 |

OTHER PUBLICATIONS

International Search Report dated Jul. 12, 2016 from International Application No. PCT/EP2016/072587 (5 pages).
Magnuson, Eric C. et al.: "Theoretical study of 1,3-dipolar cycloadditions of nitrone and fulminic acid with substituted ethylenes", Journal of Computational Chemistry, vol. 19, No. 16, pp. 1795-1804 (1998).
Written Opinion of the International Searching Authority dated Jul. 12, 2016 from International Application No. PCT/EP2016/072587 (6 pages).

* cited by examiner

*Primary Examiner* — John Pak
(74) *Attorney, Agent, or Firm* — Baker & Hostetler, LLP; Toni-Junell Herbert

(57) ABSTRACT

Compounds of formula (I) wherein the substituents are as defined in claim 1, and the agrochemically acceptable salts salts, stereoisomers, enantiomers, tautomers and N-oxides of those compounds, and their uses as insecticides.

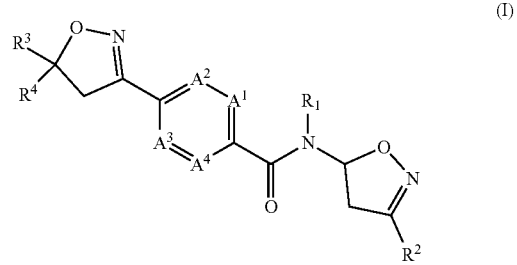

16 Claims, No Drawings

ISOXAZOLINE-SUBSTITUTED BENZAMIDES AND ANALOGUES AS INSECTICIDES

CROSS-REFERENCE TO RELATED APPLICATIONS

This application is a 371 National Stage application of International Application No. PCT/EP2016/072587, filed Sep. 22, 2016, which claims priority to European Patent Application No. 15186538.3, filed Sep. 23, 2015, the entire contents of which are hereby incorporated by reference.

The present invention relates to certain isoxazoline derivatives, to intermediates for preparing such derivatives, to insecticidal, acaricidal, nematicidal and molluscicidal compositions comprising such derivatives and to methods of using these derivatives to control insect, acarine, nematode and mollusc pests.

Certain isoxazoline derivatives with insecticidal properties are disclosed, for example, in WO2011067272. It has now surprisingly been found that certain isoxazoline derivatives have highly potent insecticidal properties.

The present invention accordingly relates to compounds of formula (I),

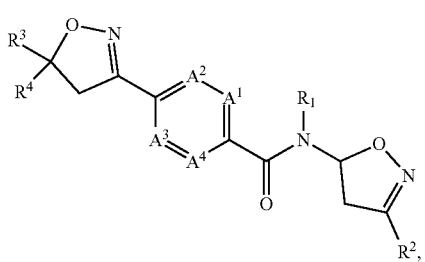

wherein
$A^1$, $A^2$, $A^3$ and $A^4$ are, independently of one another, C—H, C—$R^5$ or N;
$R^1$ is hydrogen, formyl, $C_1$-$C_8$alkyl, $C_1$-$C_8$alkylcarbonyl-, $C_1$-$C_8$alkoxy, $C_1$-$C_8$alkoxy-$C_1$-$C_8$alkyl or $C_1$-$C_8$alkoxycarbonyl, phenyl-$C_1$-$C_8$alkoxycarbonyl, phenyl-$C_1$-$C_4$alkyl, phenyl-$C_1$-$C_4$alkyl wherein the phenyl moiety is substituted by one to three $R^7$;
$R^2$ is hydrogen, halogen, cyano, $C_1$-$C_8$alkyl or $C_1$-$C_8$alkyl substituted by one to three $R^{6a}$, $C_1$-$C_8$haloalkyl or $C_1$-$C_8$haloalkyl substituted by one to three $R^{6a}$, $C_3$-$C_8$cycloalkyl or $C_3$-$C_8$cycloalkyl substituted by one to three $R^{6b}$, $C_3$-$C_8$cycloalkyl where one carbon atom is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_3$-$C_8$cycloalkyl-$C_1$-$C_8$haloalkyl, $C_2$-$C_8$alkenyl or $C_2$-$C_8$alkenyl substituted by one to three $R^{6a}$, $C_2$-$C_5$haloalkenyl or $C_2$-$C_8$haloalkenyl substituted by one to three $R^{6a}$, $C_2$-$C_5$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl or 5-6 membered heteroaryl-$C_1$-$C_4$alkyl wherein the heteroaryl moiety is substituted by one to three $R^7$, —NH($R^8$), —N($R^8$)($R^9$), —O$R^{10}$, —S$R^{10}$, —S(O)$R^{10}$, —S(O)$_2R^{10}$, CO$R^{10}$, COO$R^{10}$;
$R^3$ is $C_1$-$C_8$haloalkyl;
$R^4$ is phenyl or phenyl substituted by one to three $R^{6b}$ or pyridine or pyridine substituted by one to three $R^{6b}$;
$R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —CH=CH—CH=CH— bridge or a —N=CH—CH=CH— bridge;
each $R^{6a}$ is independently halogen, cyano, nitro, amino, hydroxy, oxo, $C_1$-$C_8$alkylamino, hydroxyimino, $C_1$-$C_8$alkyloxyimino, di-$C_1$-$C_8$alkylamino, $C_1$-$C_8$alkoxy, acetyloxy, formyloxy, $C_1$-$C_8$haloalkoxy, $C_1$-$C_4$alkylthio or $(C_1$-$C_4$alkyl$)_{0-3}$silyl;
each $R^{6b}$ is independently halogen, cyano, nitro, $C_1$-$C_8$alkyl, $C_1$-$C_8$haloalkyl, amino, $C_1$-$C_8$alkylamino, di-$C_1$-$C_8$alkylamino, hydroxyl, $C_1$-$C_4$alkylthio, $C_1$-$C_8$alkoxy or $C_1$-$C_8$haloalkoxy;
$R^7$ is independently halogen, cyano, nitro, $C_1$-$C_8$alkyl, $C_1$-$C_8$haloalkyl, $C_1$-$C_8$alkoxy, or $C_1$-$C_8$haloalkoxy;
$R^8$ and $R^9$ are independently hydrogen, cyano, $C_1$-$C_8$alkyl or $C_1$-$C_8$alkyl substituted by one to three $R^{6a}$, $C_1$-$C_8$alkoxy, $C_1$-$C_8$haloalkoxy, $C_1$-$C_8$haloalkoxy substituted by one to three $R^{6a}$, $C_1$-$C_5$alkoxy substituted by one to three $R^{6a}$, $C_1$-$C_8$haloalkyl or $C_1$-$C_8$haloalkyl substituted by one to three $R^{6a}$, $C_3$-$C_8$cycloalkyl or $C_3$-$C_8$cycloalkyl substituted by one to three $R^{6b}$, $C_3$-$C_8$cycloalkyl where one carbon atom is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_3$-$C_8$cycloalkyl-$C_1$-$C_8$haloalkyl, $C_2$-$C_8$alkenyl or $C_2$-$C_8$alkenyl substituted by one to three $R^{6a}$, $C_2$-$C_8$haloalkenyl or $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl or 5-6 membered heteroaryl-$C_1$-$C_4$alkyl wherein the heteroaryl moiety is substituted by one to three $R^7$, or $R^8$ and $R^9$ together with the nitrogen atom can be linked through a $C_3$-$C_8$alkylene chain, a $C_3$-$C_8$alkylene chain substituted by one to three $R^{6b}$ or a $C_3$-$C_8$alkylene chain, where one carbon atom is replaced by O, S, S(O) or $SO_2$;
$R^{10}$ is hydrogen, cyano, $C_1$-$C_8$alkyl or $C_1$-$C_8$alkyl substituted by one to three $R^{6a}$, $C_1$-$C_8$haloalkyl or $C_1$-$C_8$haloalkyl substituted by one to three $R^{6a}$, $C_3$-$C_8$cycloalkyl or $C_3$-$C_8$cycloalkyl substituted by one to three $R^{6b}$, $C_3$-$C_8$cycloalkyl where one carbon atom is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_3$-$C_8$cycloalkyl-$C_1$-$C_8$haloalkyl, $C_2$-$C_8$alkenyl or $C_2$-$C_8$alkenyl substituted by one to three $R^{6a}$, $C_2$-$C_8$haloalkenyl or $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl or 5-6 membered heteroaryl-$C_1$-$C_4$alkyl wherein the heteroaryl moiety is substituted by one to three $R^7$;
and an agrochemically acceptable salt, stereoisomer, enantiomer, tautomer and N-oxide thereof.

Compounds of formula (I) which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula (I) which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexyloxycarbonyl.

The cycloalkyl groups preferably have from 3 to 6 ring carbon atoms, for example cyclopropyl, cyclobutyl, cyclopentyl and cyclohexyl.

Heteroaryl groups preferably are the 5-6 membered heteroaryls or the 5-6 membered heteroaryls substituted by one to three $R^7$ where the heteroaryl groups contain 1 to 3 hetero atoms selected from the group consisting of nitrogen, oxygen and sulfur, it not being possible for each ring system to contain more than 2 oxygen atoms and more than 2 sulfur atoms. Examples of monocyclic groups include pyridyl, pyridazinyl, pyrimidinyl, pyrazinyl, pyrrolyl, pyrazolyl, imidazolyl, triazolyl (e.g. 1.2.4 triazoyl), furanyl, thiophenyl, oxazolyl, isoxazolyl, oxadiazolyl, thiazolyl, isothiazolyl, tetrazolyl and thiadiazolyl.

The compounds of formula (I) according to the invention also include hydrates which may be formed during the salt formation.

Preferred values of $A^1$, $A^2$, $A^3$, $A^4$, $R^1$, $R^2$, $R^3$, $R^4$, $R^5$, $R^{6a}$, $R^{6b}$, $R^7$, $R^8$, $R^9$ and $R^{10}$ in relation to each compound of the present invention, including the intermediate compounds, are, in any combination (including combinations of preferred values with the original values) as set out below.

Preferably no more than two of $A^1$, $A^2$, $A^3$ and $A^4$ are nitrogen.

Preferably $A^1$ is C—H or C—$R^5$; more preferably $A^1$ is C—$R^5$.

Preferably $A^2$ is C—H or C—$R^5$; more preferably $A^2$ is C—H.

Preferably $A^3$ is C—H or N; more preferably $A^3$ is C—H.
Preferably $A^4$ is C—H or N; more preferably $A^4$ is C—H.
Preferably $A^1$ is C—$R^5$; $A^2$ is C—H; $A^3$ is C—H; and $A^4$ is C—H.

Preferably $R^1$ is hydrogen, formyl, $C_1$-$C_8$alkyl, $C_1$-$C_8$alkylcarbonyl- or $C_1$-$C_8$alkoxycarbonyl-; more preferably hydrogen, methyl, ethyl, methylcarbonyl-, or methoxycarbonyl; most preferably hydrogen, formyl, methyl or methoxycarbonyl; especially hydrogen or formyl; more especially hydrogen.

Preferably $R^2$ is halogen, $C_1$-$C_4$alkyl, $C_3$-$C_6$cycloalkyl, $C_1$-$C_4$haloalkyl, $C_1$-$C_4$alkoxy, $C_1$-$C_4$haloalkoxy or di-$C_1$-$C_4$alkylamino, $C_1$-$C_4$alkylthio, $C_1$-$C_4$alkyloxycarbonyl, cyano, most preferably chlorine, bromine, fluorine, methyl, ethyl, propyl, isopropyl, cyclopropyl, cyclobutyl, trifluoromethyl, allyl, methoxy, ethoxy, 2,2,2-trifluoroethoxy, 2,2-difluoroethoxy, methoxycarbonyl, ethoxycarbonyl, methylthio and methylsulfone.

Preferably $R^3$ is $C_1$-$C_4$haloalkyl; more preferably chlorodifluoromethyl or trifluoromethyl; most preferably trifluoromethyl.

$R^4$ is preferably phenyl or phenyl substituted by one to three $R^{6b}$; more preferably $R^4$ is phenyl substituted by one to three substituents selected from F, Cl, Br, $CF_3$ or $SCH_3$; even more preferably $R^4$ is phenyl substituted by one to three $R^{6b}$; most preferably $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 4-fluoro-3,5-dichlorophenyl or 3,4,5-trichloro-phenyl; more especially $R^4$ is 3-chloro-5-trifluoromethyl-phenyl, 3,5-dichloro-phenyl, 3,5-bis-(trifluoromethyl)-phenyl, 3,5-dichloro-4-fluoro-phenyl or 3,4,5-trichloro-phenyl.

Preferably $R^5$ is independently halogen, cyano, nitro, $C_1$-$C_8$alkyl, $C_3$-$C_8$cycloalkyl, $C_1$-$C_8$haloalkyl, or $C_2$-$C_8$alkenyl, or two $R^5$ on adjacent carbon atoms together form a —CH=CH—CH=CH— bridge; more preferably $R^5$ is independently halogen, cyano, nitro, $C_1$-$C_8$alkyl, $C_3$-$C_8$cycloalkyl, $C_1$-$C_8$haloalkyl, or $C_2$-$C_8$alkenyl; even more preferably $R^5$ is halogen, cyano, nitro, $C_1$-$C_8$alkyl, $C_2$-$C_8$ alkenyl, $C_3$-$C_8$cycloalkyl, or $C_1$-$C_8$haloalkyl.

In a further embodiment $R^5$ is independently fluoro, chloro, bromo, trifluoromethyl, methyl or two $R^5$ on adjacent carbon atoms together form a —CH=CH—CH=CH— bridge; more preferably $R^5$ is bromo, chloro, fluoro, cyclopropyl, trifluoromethyl, vinyl, or methyl; most preferably chloro, bromo, trifluoromethyl, fluoro, methyl.

Preferably $R^{6a}$ independently is cyano, halogen, nitro, $C_1$-$C_4$alkoxy, $C_1$-$C_4$haloalkoxy or $C_1$-$C_4$alkylthio; more preferably fluoro, cyano, nitro, methoxy, difluoromethoxy, trifluoromethoxy or methylthio.

Preferably $R^{6b}$ independently is halogen, cyano, nitro, $C_1$-$C_4$alkyl, $C_1$-$C_4$haloalkyl, $C_1$-$C_4$alkoxy, or $C_1$-$C_4$haloalkoxy; more preferably bromo, chloro, fluoro, cyano, nitro, methyl, ethyl, trifluoromethyl, methoxy, difluoromethoxy, trifluoromethoxy; more preferably chloro, fluoro, cyano, nitro, methyl, ethyl, trifluoromethyl, methoxy, or trifluoromethoxy; especially chloro, fluoro, cyano, nitro, methyl, ethyl, trifluoromethyl, methoxy, or trifluoromethoxy; more especially bromo, fluoro, chloro, or trifluoromethyl.

Preferably $R^7$ are independently from each other halogen, cyano, $C_1$-$C_4$alkyl, $C_1$-$C_4$haloalkyl, $C_1$-$C_4$alkoxy or $C_1$-$C_4$haloalkoxy; more preferably, methyl, fluoro, chloro, bromo, trifluoromethyl, trifluoromethoxy, cyano or methoxy.

Preferably $R^8$ and $R^9$ are independently hydrogen, $C_1$-$C_8$alkyl, $C_3$-$C_8$cycloalkyl, $C_1$-$C_8$haloalkyl, $C_1$-$C_8$alkoxyalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^7$, 5-6 membered heteoaryl-$C_1$-$C_4$alkyl or 5-6 membered heteroaryl-$C_1$-$C_4$alkyl wherein the heteroaryl moiety is substituted by one to three $R^7$; more preferably $R^8$ and $R^9$ are independently hydrogen, $C_1$-$C_8$alkyl, $C_3$-$C_8$cycloalkyl, $C_1$-$C_8$alkoxyalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^7$, 5-6 membered heteoaryl-$C_1$-$C_4$alkyl or 5-6 membered heteroaryl-$C_1$-$C_4$alkyl wherein the heteroaryl moiety is substituted by one to three $R^7$; yet even more preferably $R^8$ and $R^9$ are independently hydrogen, $C_1$-$C_4$alkyl, $C_3$-$C_6$cycloalkyl, $C_1$-$C_4$haloalkyl, $C_1$-$C_4$alkoxy-$C_1$-$C_4$alkyl, phenyl-$CH_2$— or phenyl-$CH_2$— wherein the phenyl moiety is substituted by one to three $R^7$, thietanyl, oxetanyl, oxo-thietanyl, or dioxo-thietanyl; yet even more preferably $R^8$ and $R^9$ are independently methyl, ethyl, propyl, isopropyl, cyclopropyl, cyclobutyl, oxetanyl, thietanyl, trifluoroethyl, difluoroethyl, allyl, propargyl, cyanomethyl, benzyl, benzyl substituted by one to three $R^7$, or pyridine-methyl- or pyridine-methyl-substituted by one to three $R^7$; especially $R^8$ and $R^9$ are independently methyl, ethyl, cyclopropyl and trifluoroethyl.

Preferably each $R^{10}$ is independently hydrogen, $C_1$-$C_8$alkyl, $C_1$-$C_8$haloalkyl or $C_3$-$C_8$cycloalkyl, more preferably $C_1$-$C_4$alkyl, $C_1$-$C_4$haloalkyl or $C_3$-$C_6$cycloalkyl, most preferably, methyl, ethyl, 2,2,2-trifluoroethyl, 2,2-difluoroethyl or cyclopropyl.

In an embodiment E1 of formula (I), independent of other embodiments, $A^1$ is $CR^5$ and $A^2$, $A^3$ and $A^4$ are each CH, wherein $R^5$ is as defined under formula (I) above.

In an embodiment E2 of formula (I), independent of other embodiments, $R^1$ is hydrogen, formyl, $C_1$-$C_8$alkyl, $C_1$-$C_8$alkylcarbonyl- or $C_1$-$C_8$alkoxycarbonyl.

In an embodiment E3 of formula (I), independent of other embodiments, $R^2$ is selected from halogen, $C_1$-$C_8$alkyl, $C_1$-$C_8$alkyl substituted by one to three $R^{6a}$, $C_3$-$C_8$cycloalkyl, $C_1$-$C_8$haloalkyl, di-$C_1$-$C_8$alkylamino, —$SR^{10}$, —$S(O)R^{10}$, —$S(O)_2R^{10}$, phenyl and phenyl substituted by one to three $R^{6b}$.

In an embodiment E4 of formula (I), independent of other embodiments, $R^3$ is $C_1$-$C_4$haloalkyl.

In an embodiment E5 of formula (I), independent of other embodiments, $R^4$ is phenyl or phenyl substituted by one to three $R^{6b}$, wherein $R^{6b}$ is as defined under formula (I) above.

Embodiment E6 of formula (I) provides compounds of formula (I) wherein $A^1$ is $CR^5$ and $A^2$, $A^3$ and $A^4$ are each CH; $R^1$ is hydrogen, methyl, ethyl, formyl, methylcarbonyl-, or methoxycarbonyl; $R^2$ is selected from halogen, cyano, $C_1$-$C_8$alkyl, $C_1$-$C_8$alkyl substituted by one to three $R^{6a}$, $C_3$-$C_8$cycloalkyl, $C_1$-$C_8$haloalkyl, $C_1$-$C_8$haloalkyl substituted by one to three $R^{6a}$, $C_3$-$C_8$cycloalkyl-$C_1$-$C_8$alkyl, $C_8$cycloalkyl substituted by one to three $R^{6b}$, di-$C_1$-$C_8$alkylamino, phenyl and phenyl substituted by one to three $R^{6b}$, —$OR^{10}$, —$S(O)R^{10}$, —$S(O)_2R^{10}$, $R^3$ is $C_1$-$C_4$haloalkyl; $R^4$ is phenyl or phenyl substituted by one to three $R^{6b}$; wherein $R^5$ is halogen or $C_1$-$C_8$alkyl, $C_3$-$C_8$cycloalkyl, $C_1$-$C_8$haloalkyl, or $C_2$-$C_8$alkenyl; $R^{6a}$ is independently cyano, nitro, $C_1$-$C_4$alkoxy, or $C_1$-$C_4$haloalkoxy; and $R^{6b}$ is independently halogen, cyano, nitro, $C_1$-$C_4$alkyl, or $C_1$-$C_4$haloalkyl, $C_1$-$C_4$alkylthio, $C_1$-$C_4$alkoxy, or $C_1$-$C_4$haloalkoxy.

Embodiment E7 of formula (I) provides compounds of formula (I) wherein $A^1$ is $CR^5$ and $A^2$, $A^3$ and $A^4$ are each CH; $R^1$ is hydrogen, methyl, ethyl, formyl, methylcarbonyl-, or methoxycarbonyl; $R^2$ is selected from halogen, $C_1$-$C_4$alkyl, $C_1$-$C_4$alkyl substituted by one to three $R^{6a}$, $C_3$-$C_5$cycloalkyl, $C_4$haloalkyl, $C_1$-$C_4$haloalkyl substituted by one to three $R^{6a}$, $C_3$-$C_6$cycloalkyl-$C_1$-$C_4$alkyl, di-$C_1$-$C_4$alkylamino, phenyl, cyano, —$OR^{10}$, —$S(O)R^{10}$ —$S(O)_2R^{10}$; $R^3$ is $C_1$-$C_4$haloalkyl; $R^4$ is phenyl or phenyl substituted by one to three $R^{6b}$; wherein $R^5$ is halogen, cyano, nitro, $C_1$-$C_4$alkyl, $C_3$-$C_6$cycloalkyl, $C_1$-$C_4$haloalkyl, $C_2$-$C_4$alkenyl; $R^{6a}$ is independently cyano, nitro, methoxy, difluoromethoxy or trifluoromethoxy; and $R^{6b}$ is independently bromo, chloro, fluoro, cyano, nitro, methyl, ethyl, trifluoromethyl, methoxy, difluoromethoxy, trifluoromethoxy.

Embodiment E8 of formula (I) provides compounds of formula (I) wherein $A^1$ is $CR^5$ and $A^2$, $A^3$ and $A^4$ are each CH; $R^1$ is hydrogen; $R^2$ is selected from halogen, $C_1$-$C_4$alkyl, $C_1$-$C_4$alkyl substituted by one to three $R^{6a}$, $C_3$-$C_5$cycloalkyl, $C_1$-$C_4$haloalkyl, $C_1$-$C_4$haloalkyl substituted by one to three $R^{6a}$, $C_3$-$C_5$cycloalkyl-$C_1$-$C_4$alkyl, $C_3$-$C_5$cycloalkyl substituted by one to three $R^{6b}$, di-$C_1$-$C_4$alkylamino, —$OR^{10}$, —$SR^{10}$, —$S(O)R^{10}$, —$S(O)_2R^{10}$ and phenyl which can be mono- di- or trisubstituted by halogen; $R^3$ is chlorodifluoromethyl or trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; and wherein $R^5$ is bromo, chloro, fluoro, cyano, nitro, methyl, ethyl, trifluoromethyl, cyclopropyl, or vinyl; $R^{6a}$ is independently cyano, nitro, methoxy, difluoromethoxy or trifluoromethoxy;

Embodiment E9 of formula (I) provides compounds of formula (I) wherein $A^1$ is $CR^5$ and $A^2$, $A^3$ and $A^4$ are each CH; $R^1$ is hydrogen; $R^2$ is selected from halogen, $C_1$-$C_4$alkyl, $C_1$-$C_4$alkyl substituted by one to three $R^{6a}$, $C_3$-$C_5$cycloalkyl, —$OR^{10}$, —$S(O)R^{10}$, —$S(O)_2R^{10}$, $C_1$-$C_4$haloalkyl, $C_1$-$C_4$haloalkyl substituted by one to three $R^{6a}$, $C_3$-$C_5$cycloalkyl-$C_1$-$C_4$alkyl, $C_3$-$C_5$cycloalkyl substituted by one to three $R^{6b}$, and di-$C_1$-$C_4$alkylamino; $R^3$ is chlorodifluoromethyl or trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; wherein $R^5$ is bromo, chloro, fluoro, cyano, nitro, methyl, ethyl, trifluororomethyl, cyclopropyl, or vinyl; $R^{6a}$ is independently fluoro, cyano, nitro, methoxy, difluoromethoxy or trifluoromethoxy;

Embodiment E10 of formula (I) provides compounds of formula (I) wherein $A^1$ is $CR^5$ and $A^2$, $A^3$ and $A^4$ are each CH; $R^1$ is hydrogen; $R^2$ is selected from chloro, bromo, methyl, ethyl, propyl, trifluoromethyl, difluoromethyl, cyanomethyl, methoxy, ethoxy, 2,2,2-trifluoroethoxy, 2,2-difluoroethoxy, and dimethylamino; $R^3$ is chlorodifluoromethyl or trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,5-dichloro-4-fluoro-phenyl, 3,4-dichloro-phenyl, 3-trifluoromethyl-phenyl, 4-bromo-3,5-dichlorophenyl, 4-fluoro-3,5-dichlorophenyl or 3,4,5-trichloro-phenyl; wherein $R^5$ is bromo, chloro, fluoro, cyano, nitro, methyl, ethyl, trifluoromethyl, cyclopropyl, or vinyl; each $R^{6a}$ is independently fluoro, cyano, nitro, methoxy, difluoromethoxy or trifluoromethoxy.

Embodiment E11 of formula (I) provides compounds of formula (I) wherein $A^2$, $A^3$ and $A^4$ are each CH; $R^1$ is hydrogen; $R^3$ is chlorodifluoromethyl or trifluoromethyl; $A^1$ is $CR^5$, wherein $R^5$ is chloro, bromo, trifluoromethyl, or methyl; $R^2$ is selected from chloro, bromo, methyl, ethyl, propyl, trifluoromethyl, difluoromethyl, methoxy, ethoxy, 2,2,2-trifluoroethoxy, 2,2-difluoroethoxy, and dimethylamino; and $R^4$ is 3-chloro-5-trifluoromethyl-phenyl, 3-bromo-5-trifluoromethyl-phenyl, 3-trifluoromethyl-phenyl, 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluoro-phenyl, pyridyl, or 3-5-substituted pyridyl wherein the substituents are selected from bromo, chloro, fluoro and trifluoromethyl.

Embodiment E12 of formula (I) provides compounds of formula (I) wherein $A^2$, $A^3$ and $A^4$ are each CH; $R^1$ is hydrogen; $R^3$ is trifluoromethyl; $A^1$ is $CR^5$, wherein $R^5$ is chloro or methyl; $R^2$ is selected from chloro, bromo, methyl, ethyl, propyl, trifluoromethyl, difluoromethyl, cyanomethyl, methoxy, ethoxy, 2,2,2-trifluoroethoxy, 2,2-difluoroethoxy and dimethylamino; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 4-fluoro-3,5-dichlorophenyl or 3,4,5-trichloro-phenyl, 3,5-dichloro-4-fluoro-phenyl; especially $R^4$ is 3,5-dibromo-phenyl, 3,5-dichloro-phenyl, 3,5-bis-(trifluoromethyl)-phenyl, 3-chloro-5-trifluoromethyl-phenyl, 3-bromo-5-trifluoromethyl-phenyl, 4-bromo-3,5-dichlorophenyl, 3,4,5-trichloro-phenyl, 3,5-dichloro-4-fluoro-phenyl, pyridyl, or 3-5-substituted pyridyl wherein the substituents are selected from the group consisting of bromo, chloro, fluoro and trifluoromethyl.

Embodiment E13 of formula (I) provides compounds of formula (I) wherein $A^2$, $A^3$ and $A^4$ are each CH; $R^1$ is hydrogen; $R^3$ is chlorodifluoromethyl or trifluoromethyl; $A^1$ is $CR^5$, wherein $R^5$ is chloro, bromo, trifluoromethyl, fluoro, or methyl; $R^2$ is selected from, chloro, bromo, methyl, ethyl, propyl, trifluoromethyl, difluoromethyl, cyanomethyl, methoxy, ethoxy, 2,2,2-trifluoroethoxy and 2,2-difluoroethoxy, and $R^4$ is phenyl, pyridyl, mono-, di- or tri-substituted phenyl where the substituents are independently selected from the group consisting of chloro, bromo, fluoro and trifluoromethyl, or mono- or di-substituted pyridyl where the substituents are independently selected from chloro, bromo, fluoro and trifluoromethyl.

Embodiment E14 of formula (I) provides compounds of formula (I) wherein $A^2$, $A^3$ and $A^4$ are each CH; $R^1$ is hydrogen; $R^3$ is trifluoromethyl; $A^1$ is $CR^5$, wherein $R^5$ is chloro or methyl; $R^2$ is independently selected from chloro, bromo, methyl, ethyl, propyl, cyclopropyl, trifluoromethyl, difluoromethyl, methoxy, ethoxy, 2,2,2-trifluoroethoxy, 2,2-difluoroethoxy; and $R^4$ is 3,5-dichloro-4-fluoro-phenyl, 3,5-dichloro-phenyl, 3,4,5-trichloro-phenyl, 3-bromo-5-trifluoromethyl-phenyl, 3-trifluoromethyl-phenyl or 3-chloro-5-trifluoromethyl-phenyl.

Embodiment E15 of formula (I) provides compounds of formula (I) wherein $A^2$, $A^3$ and $A^4$ are each CH; $R^1$ is hydrogen; $R^3$ is trifluoromethyl; $A^1$ is $CR^5$, wherein $R^5$ is chloro; $R^2$ is selected from chloro, bromo, methyl, ethyl, propyl, trifluoromethyl, difluoromethyl, cyanomethyl, methoxy, ethoxy, 2,2,2-trifluoroethoxy, 2,2-difluoroethoxy and dimethylamino; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 4-fluoro-3,5-dichlorophenyl or 3,4,5-trichloro-phenyl, 3,5-dichloro-4-fluoro-phenyl; especially $R^4$ is 3,5-dibromo-phenyl, 3,5-dichloro-phenyl, 3,5-bis-(trifluoromethyl)-phenyl, 3-chloro-5-trifluoromethyl-phenyl, 3-bromo-5-trifluoromethyl-phenyl, 4-bromo-3,5-dichlorophenyl, 3,4,5-trichloro-phenyl, 3,5-dichloro-4-fluoro-phenyl, pyridyl, or 3-5-substituted pyridyl wherein the substituents are selected from the group consisting of bromo, chloro, fluoro and trifluoromethyl.

Embodiment E16 of formula (I) provides compounds of formula (I) wherein $A^2$, $A^3$ and $A^4$ are each CH; $R^1$ is hydrogen; $R^3$ is chlorodifluoromethyl or trifluoromethyl; $A^1$ is $CR^5$, wherein $R^5$ is chloro; $R^2$ is selected from, chloro, bromo, methyl, ethyl, propyl, trifluoromethyl, difluoromethyl, cyanomethyl, methoxy, ethoxy, 2,2,2-trifluoroethoxy and 2,2-difluoroethoxy, and $R^4$ is phenyl, pyridyl, mono-, di- or tri-substituted phenyl where the substituents are independently selected from the group consisting of chloro, bromo, fluoro and trifluoromethyl, or mono- or di-substituted pyridyl where the substituents are independently selected from chloro, bromo, fluoro and trifluoromethyl.

Embodiment E17 of formula (I) provides compounds of formula (I) wherein $A^2$, $A^3$ and $A^4$ are each CH; $R^1$ is hydrogen; $R^3$ is trifluoromethyl; $A^1$ is $CR^5$, wherein $R^5$ is chloro; $R^2$ is independently selected from chloro, bromo, methyl, ethyl, propyl, cyclopropyl, trifluoromethyl, difluoromethyl, methoxy, ethoxy, 2,2,2-trifluoroethoxy, 2,2-difluoroethoxy; and $R^4$ is 3,5-dichloro-4-fluoro-phenyl, 3,5-dichloro-phenyl, 3,4,5-trichloro-phenyl, 3-bromo-5-trifluoromethyl-phenyl, 3-trifluoromethyl-phenyl or 3-chloro-5-trifluoromethyl-phenyl.

Embodiment E18 of formula (I) provides compounds of formula (I) wherein $A^2$, $A^3$ and $A^4$ are each CH; $R^1$ is hydrogen; $R^3$ is trifluoromethyl; $A^1$ is $CR^5$, wherein $R^5$ is bromo; $R^2$ is selected from chloro, bromo, methyl, ethyl, propyl, trifluoromethyl, difluoromethyl, cyanomethyl, methoxy, ethoxy, 2,2,2-trifluoroethoxy, 2,2-difluoroethoxy and dimethylamino; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 4-fluoro-3,5-dichlorophenyl or 3,4,5-trichloro-phenyl, 3,5-dichloro-4-fluoro-phenyl; especially $R^4$ is 3,5-dibromo-phenyl, 3,5-dichloro-phenyl, 3,5-bis-(trifluoromethyl)-phenyl, 3-chloro-5-trifluoromethyl-phenyl, 3-bromo-5-trifluoromethyl-phenyl, 4-bromo-3,5-dichlorophenyl, 3,4,5-trichloro-phenyl, 3,5-dichloro-4-fluoro-phenyl, pyridyl, or 3-5-substituted pyridyl wherein the substituents are selected from the group consisting of bromo, chloro, fluoro and trifluoromethyl.

Embodiment E19 of formula (I) provides compounds of formula (I) wherein $A^2$, $A^3$ and $A^4$ are each CH; $R^1$ is hydrogen; $R^3$ is chlorodifluoromethyl or trifluoromethyl; $A^1$ is $CR^5$, wherein $R^5$ is bromo; $R^2$ is selected from, chloro, bromo, methyl, ethyl, propyl, trifluoromethyl, difluoromethyl, cyanomethyl, methoxy, ethoxy, 2,2,2-trifluoroethoxy and 2,2-difluoroethoxy, and $R^4$ is phenyl, pyridyl, mono-, di- or tri-substituted phenyl where the substituents are independently selected from the group consisting of chloro, bromo, fluoro and trifluoromethyl, or mono- or di-substituted pyridyl where the substituents are independently selected from chloro, bromo, fluoro and trifluoromethyl.

Embodiment E20 of formula (I) provides compounds of formula (I) wherein $A^2$, $A^3$ and $A^4$ are each CH; $R^1$ is hydrogen; $R^3$ is trifluoromethyl; $A^1$ is $CR^5$, wherein $R^5$ is bromo; $R^2$ is independently selected from chloro, bromo, methyl, ethyl, propyl, cyclopropyl, trifluoromethyl, difluoromethyl, methoxy, ethoxy, 2,2,2-trifluoroethoxy, 2,2-difluoroethoxy; and $R^4$ is 3,5-dichloro-4-fluoro-phenyl, 3,5-dichloro-phenyl, 3,4,5-trichloro-phenyl, 3-bromo-5-trifluoromethyl-phenyl, 3-trifluoromethyl-phenyl or 3-chloro-5-trifluoromethyl-phenyl.

Embodiment E21 of formula (I) provides compounds of formula (I) wherein $A^2$, $A^3$ and $A^4$ are each CH; $R^1$ is hydrogen; $R^3$ is trifluoromethyl; $A^1$ is $CR^5$, wherein $R^5$ is trifluoromethyl; $R^2$ is selected from chloro, bromo, methyl, ethyl, propyl, trifluoromethyl, difluoromethyl, cyanomethyl, methoxy, ethoxy, 2,2,2-trifluoroethoxy, 2,2-difluoroethoxy and dimethylamino; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 4-fluoro-3,5-dichlorophenyl or 3,4,5-trichloro-phenyl, 3,5-dichloro-4-fluoro-phenyl; especially $R^4$ is 3,5-dibromo-phenyl, 3,5-dichloro-phenyl, 3,5-bis-(trifluoromethyl)-phenyl, 3-chloro-5-trifluoromethyl-phenyl, 3-bromo-5-trifluoromethyl-phenyl, 4-bromo-3,5-dichloro-phenyl, 3,4,5-trichloro-phenyl, 3,5-dichloro-4-fluoro-phenyl, pyridyl, or 3-5-substituted pyridyl wherein the substituents are selected from the group consisting of bromo, chloro, fluoro and trifluoromethyl.

Embodiment E22 of formula (I) provides compounds of formula (I) wherein $A^2$, $A^3$ and $A^4$ are each CH; $R^1$ is hydrogen; $R^3$ is chlorodifluoromethyl or trifluoromethyl; $A^1$ is $CR^5$, wherein $R^5$ is trifluoromethyl; $R^2$ is selected from, chloro, bromo, methyl, ethyl, propyl, trifluoromethyl, difluoromethyl, cyanomethyl, methoxy, ethoxy, 2,2,2-trifluoroethoxy and 2,2-difluoroethoxy, and $R^4$ is phenyl, pyridyl, mono-, di- or tri-substituted phenyl where the substituents are independently selected from the group consisting of chloro, bromo, fluoro and trifluoromethyl, or mono- or di-substituted pyridyl where the substituents are independently selected from chloro, bromo, fluoro and trifluoromethyl.

Embodiment E23 of formula (I) provides compounds of formula (I) wherein $A^2$, $A^3$ and $A^4$ are each CH; $R^1$ is hydrogen; $R^3$ is trifluoromethyl; $A^1$ is $CR^5$, wherein $R^5$ is trifluoromethyl; $R^2$ is independently selected from chloro, bromo, methyl, ethyl, propyl, cyclopropyl, trifluoromethyl, difluoromethyl, methoxy, ethoxy, 2,2,2-trifluoroethoxy, 2,2-difluoroethoxy; and $R^4$ is 3,5-dichloro-4-fluoro-phenyl, 3,5-dichloro-phenyl, 3,4,5-trichloro-phenyl, 3-bromo-5-trifluoromethyl-phenyl, 3-trifluoromethyl-phenyl or 3-chloro-5-trifluoromethyl-phenyl.

Embodiment E24 of formula (I) provides compounds of formula (I) wherein $A^2$, $A^3$ and $A^4$ are each CH; $R^1$ is hydrogen; $R^3$ is trifluoromethyl; $A^1$ is $CR^5$, wherein $R^5$ is methyl; $R^2$ is selected from chloro, bromo, methyl, ethyl, propyl, trifluoromethyl, difluoromethyl, cyanomethyl, methoxy, ethoxy, 2,2,2-trifluoroethoxy, 2,2-difluoroethoxy and dimethylamino; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 4-fluoro-3,5-dichlorophenyl or 3,4,5-trichloro-phenyl, 3,5-dichloro-4-fluoro-phenyl; especially $R^4$ is 3,5-dibromo-phenyl, 3,5-dichloro-phenyl, 3,5-bis-(trifluoromethyl)-phenyl, 3-chloro-5-trifluoromethyl-phenyl, 3-bromo-5-trifluoromethyl-phenyl, 4-bromo-3,5-dichloro-phenyl, 3,4,5-trichloro-phenyl, 3,5-dichloro-4-fluoro-phenyl, pyridyl, or 3-5-substituted pyridyl wherein the substituents are selected from the group consisting of bromo, chloro, fluoro and trifluoromethyl.

Embodiment E25 of formula (I) provides compounds of formula (I) wherein $A^2$, $A^3$ and $A^4$ are each CH; $R^1$ is hydrogen; $R^3$ is chlorodifluoromethyl or trifluoromethyl; $A^1$ is $CR^5$, wherein $R^5$ is methyl; $R^2$ is selected from, chloro, bromo, methyl, ethyl, propyl, trifluoromethyl, difluoromethyl, cyanomethyl, methoxy, ethoxy, 2,2,2-trifluoroethoxy and 2,2-difluoroethoxy, and $R^4$ is phenyl, pyridyl, mono-, di- or tri-substituted phenyl where the substituents are independently selected from the group consisting of chloro, bromo, fluoro and trifluoromethyl, or mono- or di-substituted pyridyl where the substituents are independently selected from chloro, bromo, fluoro and trifluoromethyl.

Embodiment E26 of formula (I) provides compounds of formula (I) wherein $A^2$, $A^3$ and $A^4$ are each CH; $R^1$ is hydrogen; $R^3$ is trifluoromethyl; $A^1$ is $CR^5$, wherein $R^5$ is methyl; $R^2$ is independently selected from chloro, bromo, methyl, ethyl, propyl, cyclopropyl, trifluoromethyl, difluoromethyl, methoxy, ethoxy, 2,2,2-trifluoroethoxy, 2,2-difluoroethoxy; and $R^4$ is 3,5-dichloro-4-fluoro-phenyl, 3,5-dichloro-phenyl, 3,4,5-trichloro-phenyl, 3-bromo-5-trifluoromethyl-phenyl, 3-trifluoromethyl-phenyl or 3-chloro-5-trifluoromethyl-phenyl.

In a preferred embodiment the compound of formula (I) is represented by the compound of formula (Ib)

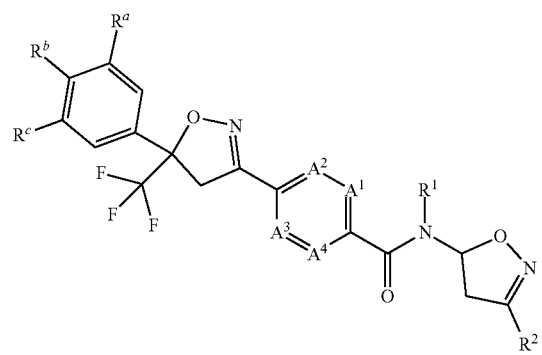

wherein
$A^1$ is C—$R^5$ and $A^2$, $A^3$ and $A^4$ are C—H;
$R^1$ is hydrogen, formyl, phenyl-$C_1$-$C_4$alkyl, phenyl-$C_1$-$C_4$alkyl wherein the phenyl moiety is substituted by one to three $R^7$;

$R^2$ is hydrogen, halogen, $C_1$-$C_8$haloalkyl or $C_1$-$C_8$haloalkyl substituted by one to three $R^{6a}$, $C_3$-$C_8$cycloalkyl or $C_3$-$C_8$cycloalkyl substituted by one to three $R^{6b}$, —NH($R^8$), —N($R^8$)($R^9$), —OR$^{10}$, —SR$^{10}$, —S(O)R$^{10}$, —S(O)$_2$R$^{10}$, COR$^{10}$, COOR$^{10}$;

$R^a$, $R^b$ and $R^c$ independently are hydrogen, halogen, $C_1$-$C_8$haloalkyl, $C_1$-$C_4$alkylthio;

$R^5$ is independently halogen, $C_1$-$C_8$alkyl;

each $R^{6a}$ is independently hydroxy, oxo, hydroxyimino, $C_1$-$C_8$alkyloxyimino, $C_1$-$C_8$alkoxy, acetyloxy, formyloxy or tri($C_1$-$C_4$alkyl)silyl;

each $R^{6b}$ is halogen, $C_1$-$C_8$haloalkyl, $C_1$-$C_4$alkylthio;

$R^7$ is independently halogen, $C_1$-$C_8$alkoxy, or $C_1$-$C_8$haloalkoxy;

$R^8$ and $R^9$ are independently hydrogen, $C_1$-$C_8$alkyl or $C_1$-$C_8$alkyl substituted by one to three $R^{6a}$;

$R^{10}$ is hydrogen, $C_1$-$C_8$alkyl or $C_1$-$C_8$alkyl substituted by one to three $R^{6a}$, $C_1$-$C_8$haloalkyl or $C_1$-$C_8$haloalkyl substituted by one to three $R^{6a}$, $C_3$-$C_8$cycloalkyl or $C_3$-$C_8$cycloalkyl substituted by one to three $R^{6b}$, $C_3$-$C_8$cycloalkyl where one carbon atom is replaced by O, S, S(O) or SO$_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, or $C_3$-$C_8$cycloalkyl-$C_1$-$C_8$haloalkyl, $C_2$-$C_8$alkenyl or $C_2$-$C_8$alkenyl substituted by one to three $R^{6a}$, $C_2$-$C_8$haloalkenyl or $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl or 5-6 membered heteroaryl-$C_1$-$C_4$alkyl wherein the heteroaryl moiety is substituted by one to three $R^7$.

In a further preferred embodiment the compound of formula (I) is represented by the compound of formula (Ib) wherein $A^1$ is C—$R^5$ and $A^2$, $A^3$ and $A^4$ are C—H;

$R^1$ is hydrogen, formyl, phenyl-$C_1$-$C_4$alkyl, phenyl-$C_1$-$C_4$alkyl wherein the phenyl moiety is substituted by one to three $R^7$;

$R^2$ is hydrogen, halogen, $C_1$-$C_8$haloalkyl or $C_1$-$C_8$haloalkyl substituted by one to three $R^{6a}$, $C_3$-$C_8$cycloalkyl, —NH($R^8$), —N($R^8$)($R^9$), —SR$^{10}$, —S(O)$_2$R$^{10}$, COR$^{10}$, COOR$^{10}$; $R^a$, $R^b$ and $R^c$ independently are hydrogen, halogen, $C_1$-$C_8$haloalkyl, $C_1$-$C_4$alkylthio; $R^5$ is independently halogen, $C_1$-$C_8$alkyl;

each $R^{6a}$ is independently hydroxy, oxo, hydroxyimino, $C_1$-$C_8$alkyloxyimino, $C_1$-$C_8$alkoxy, acetyloxy, formyloxy or tri($C_1$-$C_4$alkyl)silyl ?);

each $R^{6b}$ is halogen, $C_1$-$C_8$haloalkyl, $C_1$-$C_4$alkylthio;

$R^7$ is independently $C_1$-$C_8$alkoxy;

$R^8$ and $R^9$ are independently $C_1$-$C_8$alkyl;

$R^{10}$ is hydrogen, $C_1$-$C_8$alkyl or $C_1$-$C_8$alkyl substituted by one to three $R^{6a}$, $C_1$-$C_8$haloalkyl, $C_3$-$C_8$cycloalkyl, $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, $C_2$-$C_8$alkenyl or $C_2$-$C_8$alkenyl substituted by one to three $R^{6a}$, phenyl-$C_1$-$C_4$alkyl, 5-6 membered heteroaryl substituted by one to three $R^7$, 5-6 membered heteroaryl-$C_1$-$C_4$alkyl. Preferably at least one of the $R^a$, $R^b$ and $R^c$ is not hydrogen.

In a further preferred embodiment the compound of formula (I) is represented by the compound of formula (Ib) wherein $A^1$ is C—$R^5$ and $A^2$, $A^3$ and $A^4$ are C—H;

$R^a$ is hydrogen, halogen, $C_1$-$C_4$alkylthio or $C_1$-$C_4$haloalkyl; preferably H, chloro, fluoro, bromo, methylthio or trifluoromethyl;

$R^b$ is hydrogen, halogen, $C_1$-$C_4$alkylthio or $C_1$-$C_4$haloalkyl; preferably H, chloro, fluoro, bromo, methylthio or trifluoromethyl;

$R^c$ is hydrogen, halogen, $C_1$-$C_4$alkylthio or $C_1$-$C_4$haloalkyl; preferably H, chloro, fluoro, bromo, methylthio or trifluoromethyl;

$R^5$ is halogen or $C_1$-$C_4$alkyl, preferably chloro, methyl, trifluoromethyl or ethyl;

$R^1$ is CHO, H, CO2-tBu, (1S)-1-phenylethyl, (1R)-1-phenylethyl, (1S)-1-(4-methoxyphenyl)ethyl or (1R)-1-(4-methoxyphenyl)ethyl; preferably hydrogen or formyl;

$R^2$ is COCH$_3$, SCH$_3$, methoxy, CH$_2$CH$_3$, cyclopropyl, Cl, Br, CF$_3$, COOEt, methyl, ethoxy, methylsulfanyl, ethylsulfanyl, ethylsulfonyl, tetrahydropyran-2-yloxymethyl, acetoxymethyl, n-propoxy, 2,2-difluoroethoxy, allyloxy, isobutoxy, prop-2-ynoxy, 2,2,3,4,4,4-hexafluorobutoxy, 2-methoxyethoxy, isopropoxy, cyclopropoxy, cyclobutoxy, 2-methylallyloxy, 2-fluoroallyloxy, oxetan-3-yloxy, cyclopropylmethyl, (E)-4,4,4-trifluorobut-2-enoxy, 3-methylbut-2-enoxy, H, CH$_2$—OH, methoxymethyl, formyloxymethyl, diethoxymethyl, CHO, 2-chloroallyloxy, OCH$_2$CF$_2$CHF$_2$, OCH$_2$CF$_2$CF$_3$, OCH$_2$CF$_3$, n-butoxy, N(CH$_3$)$_2$, isopentyloxy, 2-ethoxyethoxy, 4-chlorophenoxy, 2-trimethylsilylethoxy, benzyloxy, 0-CH$_2$-cyclobutyl, O—CH$_2$-2-pyridyl, pent-4-ynoxy, 2-(dimethylamino)-2-oxo-ethoxy, 2-(ethylamino)-2-oxo-ethoxy, (2E)-2-methoxyiminopropoxy, CO$_2$H, CH=N—OH, CH=N—OCH$_3$, NH—CH$_3$, acetonyloxy, (3-ethyloxetan-3-yl)methoxy, (3-methyloxetan-3-yl)methoxy, —OCH$_2$-4-pyridyl, —O—SO$_2$CH$_3$, O—N=C(CH$_3$)—NH$_2$ or C(=N—OH)Br. Preferably at least one of the $R^a$, $R^b$ and $R^c$ is not hydrogen. More preferably at least two of the $R^a$, $R^b$ and $R^c$ are not hydrogen.

An especially preferred compound of formula (I) is represented by the compound of formula (Ib) wherein $A^1$ is C—$R^5$ and $A^2$, $A^3$ and $A^4$ are C—H;

$R^a$ is hydrogen, halogen or $C_1$-$C_4$haloalkyl; preferably chloro, fluoro, bromo or trifluoromethyl;

$R^b$ is hydrogen halogen, $C_1$-$C_4$haloalkyl or $C_1$-$C_4$alkylthio; preferably chloro, fluoro, bromo or trifluoromethyl;

$R^c$ is hydrogen, halogen or $C_1$-$C_4$haloalkyl; preferably chloro, fluoro, bromo or trifluoromethyl;

$R^5$ is halogen or $C_1$-$C_4$alkyl, preferably chloro, methyl, trifluoromethyl or ethyl;

$R^1$ is hydrogen or formyl;

$R^2$ is halogen, $C_1$-$C_4$alkyl, $C_3$-$C_6$cycloalkyl, $C_1$-$C_4$haloalkyl, $C_1$-$C_4$alkoxy, $C_1$-$C_4$alkylthio, $C_1$-$C_4$alkoxycarbonyl, $C_1$-$C_4$haloalkoxy, preferably chlorine, fluorine, bromine, methyl, ethyl, cyclopropyl, trifluoromethyl, ethoxycarbonyl, methoxycarbonyl, methoxy, ethoxy, 2,2,2-trifluoroethoxy, 2,2-difluoroethoxy or methylthio. Preferably at least one of the $R^a$, $R^b$ and $R^c$ is not hydrogen.

An equally especially preferred compound of formula (I) is represented by the compound of formula (Ib) wherein $A^1$ is C—$R^5$ and $A^2$, $A^3$ and $A^4$ are C—H;

$R^a$ is hydrogen, halogen or $C_1$-$C_4$haloalkyl;

$R^b$ is hydrogen halogen or $C_1$-$C_4$haloalkyl or $C_1$-$C_4$alkylthio;

$R^c$ is halogen or $C_1$-$C_4$haloalkyl;

$R^5$ is hydrogen, halogen or $C_1$-$C_4$alkyl, $R^1$ is hydrogen or formyl;

$R^2$ is chlorine, bromine, methyl, ethyl, cyclopropyl, trifluoromethyl, ethoxycarbonyl, methoxycarbonyl, methoxy, ethoxy, 2,2,2-trifluoroethoxy, 2,2-difluoroethoxy or methylthio. Preferably at least one of the $R^a$, $R^b$ and $R^c$ is not hydrogen. More preferably at least two of the $R^a$, $R^b$ and $R^c$ are not hydrogen.

More preferably $A^1$ is C—$R^5$ and $A^2$, $A^3$ and $A^4$ are C—H;
$R^a$ is hydrogen, halogen or $C_1$-$C_4$haloalkyl;
$R^b$ is hydrogen, halogen or $C_1$-$C_4$alkylthio;
$R^c$ is hydrogen, halogen or $C_1$-$C_4$haloalkyl;
$R^5$ is halogen or $C_1$-$C_4$alkyl,
$R^1$ is hydrogen, formyl or acetyl;
$R^2$ is chlorine, bromine, methyl, ethyl, cyclopropyl, trifluoromethyl, ethoxycarbonyl, methoxycarbonyl, methoxy, ethoxy, 2,2,2-trifluoroethoxy, 2,2-difluoroethoxy or methylthio. Preferably at least one of the $R^a$, $R^b$ and $R^c$ is not hydrogen. More preferably at least two of the $R^a$, $R^b$ and $R^c$ are not hydrogen.

Equally more preferably $A^1$ is C—$R^5$ and $A^2$, $A^3$ and $A^4$ are C—H;
$R^a$ is hydrogen, chloro, bromo, fluoro, or trifluoromethyl;
$R^b$ is hydrogen, chloro, bromo, fluoro, or trifluoromethyl;
$R^c$ is hydrogen, chloro, bromo, fluoro, or trifluoromethyl;
$R^5$ is chloro, methyl, trifluoromethyl or ethyl;
$R^1$ is hydrogen or formyl;
$R^2$ is chlorine, bromine, methyl, ethyl, cyclopropyl, trifluoromethyl, ethoxycarbonyl, methoxycarbonyl, methoxy, ethoxy, 2,2,2-trifluoroethoxy, 2,2-difluoroethoxy or methylthio. Preferably at least one of the $R^a$, $R^b$ and $R^c$ is not hydrogen. More preferably at least two of the $R^a$, $R^b$ and $R^c$ are not hydrogen. Compounds of formula (I) include at least one chiral centre and may exist as compounds of formula (I*) or compounds of formula (I**):

(I*)

(I**)

Generally compounds of formula (I**) are more biologically active than compounds of formula (I*). The invention includes mixtures of compounds (I*) and (I) in any ratio e.g. in a molar ratio of 1:99 to 99:1, e.g. 10:1 to 1:10, e.g. a substantially 50:50 molar ratio. In an enantiomerically (or epimerically) enriched mixture of formula (I), the molar proportion of compound (I**) compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixture of formula (I*), the molar proportion of the compound of formula (I*) compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula (I**) are preferred.

The compounds of the invention may be made by a variety of methods as shown in Schemes 1 to 8.

Scheme 1

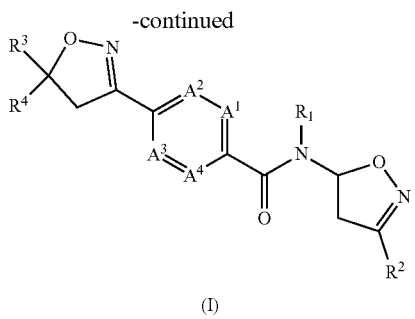

(I)

1) Compounds of formula (I) can be prepared by reacting a compound of formula (II) wherein R is OH, $C_1$-$C_6$alkoxy or Cl, F or Br, with an amine of formula (III), as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis (2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (III) can be prepared using method 11 described below.

2) Acid halides of formula (II), wherein R is Cl, F or Br, may be made from carboxylic acids of formula (II), wherein R is OH, under standard conditions, as described for example in WO09080250.

3) Carboxylic acids of formula (II), wherein R is OH, may be formed from esters of formula (II), wherein R is $C_1$-$C_6$alkoxy as described for example in WO09080250.

4) Compounds of formula (I) can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis-(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

5) Compounds of formula (IV) wherein $X^B$ is a leaving group, for example a halogen, such as bromo, can be made by a various of methods, for example as described in WO09080250.

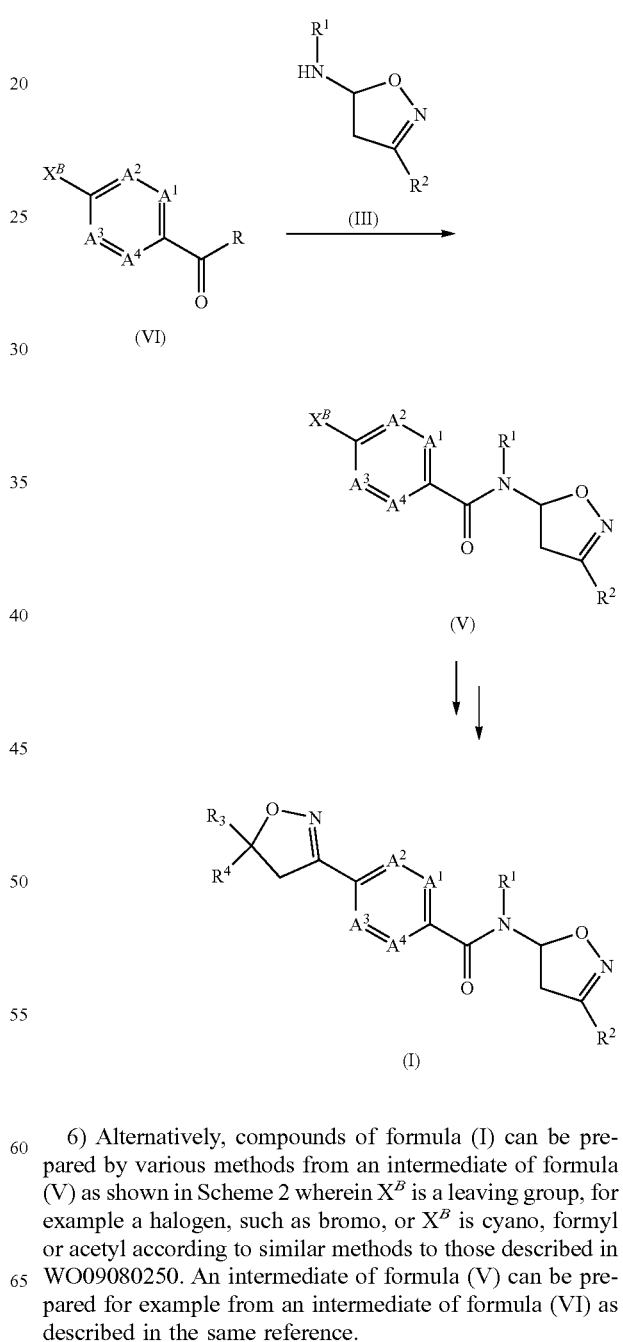

Scheme 2

6) Alternatively, compounds of formula (I) can be prepared by various methods from an intermediate of formula (V) as shown in Scheme 2 wherein $X^B$ is a leaving group, for example a halogen, such as bromo, or $X^B$ is cyano, formyl or acetyl according to similar methods to those described in WO09080250. An intermediate of formula (V) can be prepared for example from an intermediate of formula (VI) as described in the same reference.

Scheme 3

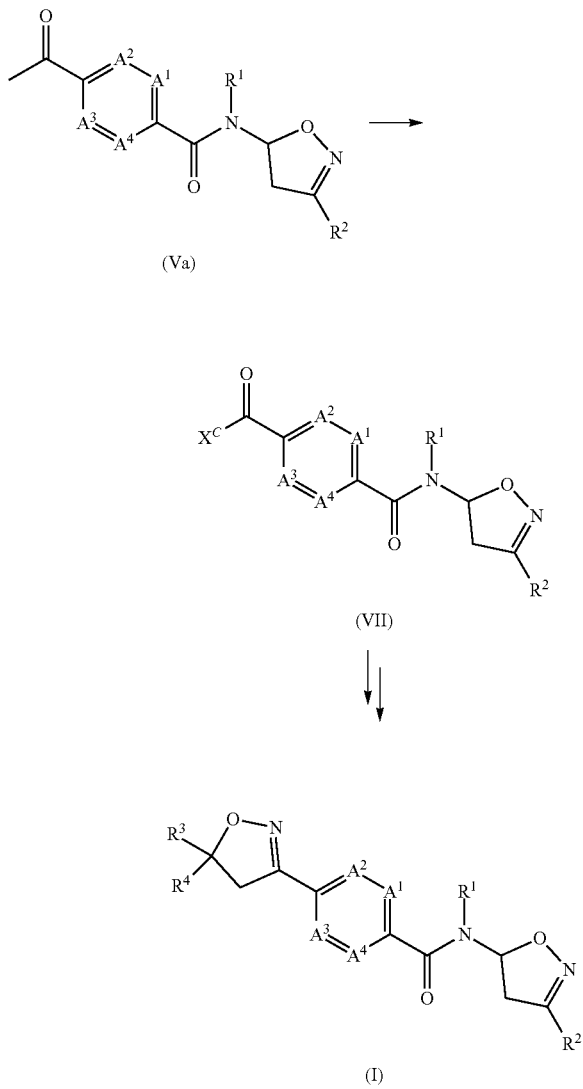

7) Alternatively, compounds of formula (I) can be prepared by various methods from an intermediate of formula (VII) as shown in Scheme 3 wherein X° is CH=C($R^3$)$R^4$, or $CH_2C(OH)(R^3)R^4$ wherein $R^3$ and $R^4$ are as defined for a compound of formula (I) according to similar methods to those described in WO09080250.

8) Compounds of formula (VII) wherein X° is CH=C($R^3$)$R^4$, or $CH_2C(OH)(R^3)R^4$ can be prepared from a compound of formula (Va) or from a compound of formula (VII) wherein X° is $CH_2$-halogen using similar methods to those described in WO09080250.

9) Compounds of formula (VII) wherein X° is $CH_2$-halogen, such as bromo or chloro, can be prepared by reacting a methyl ketone of formula (Va), with a halogenating agent, such as bromine or chlorine, in a solvent, such as acetic acid, at a temperature of from 0° C. to 50° C., preferably from ambient temperature to 40° C.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

Scheme 4

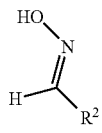

(X)

↓

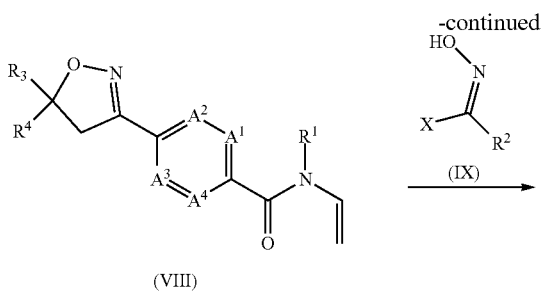

(VIII)

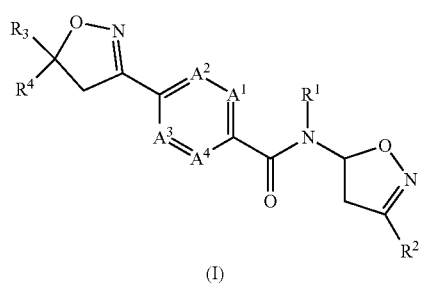

(I)

10) Compounds of formula (I) can be made by reaction of an oxime of formula (X) and a vinyl compound of formula (VIII) in a two step reaction. In the first step, the oxime of formula (X) is reacted with a halogenating agent, for example chlorine, or a succinimide, such as N-chlorosuccinimide ("NCS"), in the presence of a suitable solvent, for example a polar solvent, such as N,N-dimethylformamide. The first step is carried out at a temperature of from 0° C. to 100° C., preferably from 15° C. to 30° C., in particular at ambient temperature.

In the second step, the chloro hydroxy imine intermediate of formula (IX) is reacted with the vinyl compound of formula (VIII) in the presence of a base, for example an organic base, such as triethylamine, or an inorganic base, such as sodium hydrogen carbonate, in the presence of a suitable solvent, for example a polar solvent, such as N,N-dimethylformamide or isopropanol or an apolar solvent, such as toluene. It is possible to conduct these two steps separately and optionally to isolate the chloro hydroxy imine intermediate or more conveniently to conduct these two steps successively in one reaction vessel without isolation of the intermediate. The second step is carried out at a temperature of from 0° C. to 100° C., preferably from 15° C. to 30° C., in particular at ambient temperature. Vinyl compounds of formula (VIII) are easily prepared using methods known to a person skilled in the art, such as is described in WO2013120940.

Scheme 5

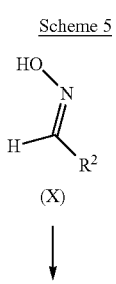

(X)

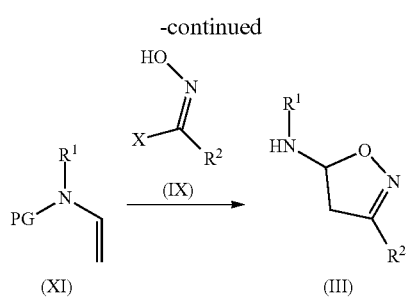

11) Compounds of formula (III) can be made by reaction of an oxime of formula (X) and a vinyl compound of formula (XI) in a two step reaction, such as is described in 10). Vinyl compounds of formula (XI), wherein PG is a protecting group, as described by Greene's Protective Groups in Organic Synthesis, Peter G. M. Wuts (Author), John Wiley & Sons; 5th Edition (23. Dec. 2014), ISBN-10: 1118057481, ISBN-13: 978-1118057483, see chapter 7 especially chapter 7 part C, are easily prepared using methods known to a person skilled in the art, or are commercially available.

Scheme 6

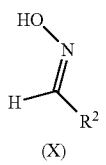

(X)

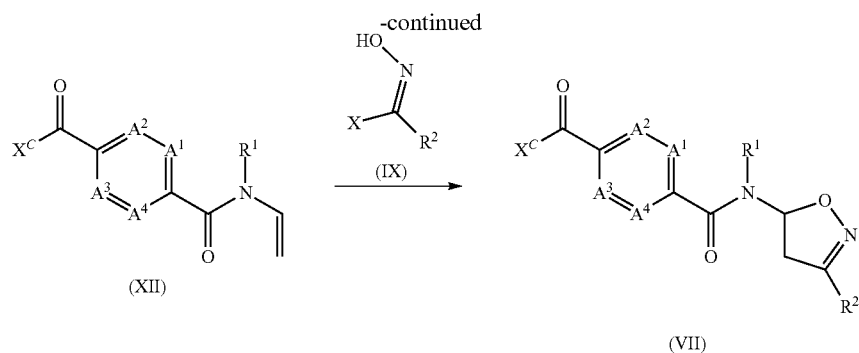

12) Compounds of formula (VII) can be made by reaction of an oxime of formula (X) and a vinyl compound of formula (XII) in a two step reaction, such as is described in 10). Vinyl compounds of formula (XII) are easily prepared using methods known to a person skilled in the art such as is described in WO2013120940.

Scheme 7

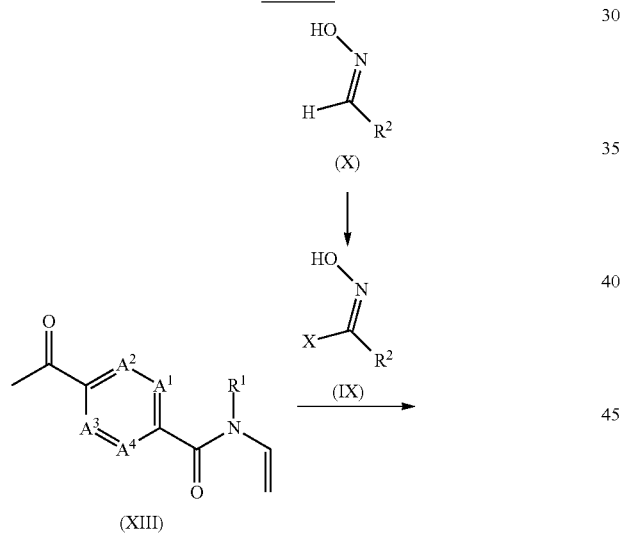

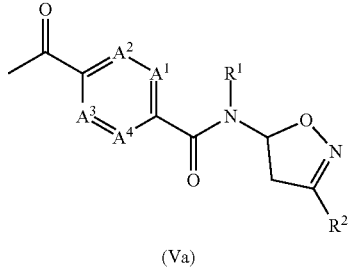

13) Compounds of formula (Va) can be made by reaction of an oxime of formula (X) and a vinyl compound of formula (XIII) in a two step reaction, such as is described in 10). Vinyl compounds of formula (XIII) are easily prepared using methods known to a person skilled in the art such as is described in WO2013120940.

Scheme 8

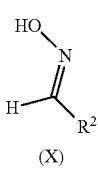

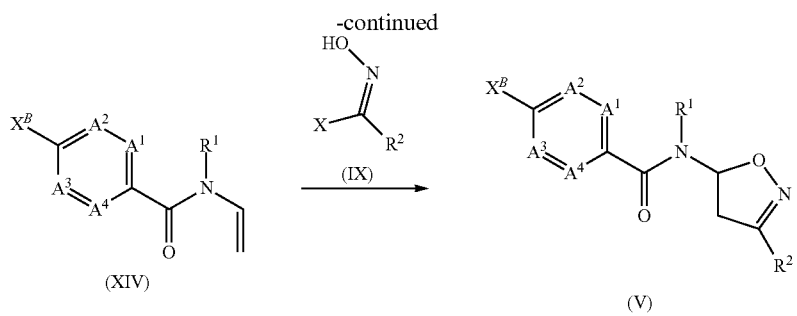

14) Compounds of formula (V) can be made by reaction of an oxime of formula (X) and a vinyl compound of formula (XIV) in a two step reaction, such as is described in 10). Vinyl compounds of formula (XIV) are easily prepared using methods known to a person skilled in the art such as is described in WO2013120940.

A compound of formula (I) can be converted in a manner known per se into another compound of formula (I) by replacing one or more substituents of the starting compound of formula (I) in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula (I) can be prepared in a manner known per se. Thus, for example, acid addition salts of compounds of formula (I) are obtained by treatment with a suitable acid or a suitable ion exchanger reagent and salts with bases are obtained by treatment with a suitable base or with a suitable ion exchanger reagent.

Salts of compounds of formula (I) can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula (I) can be converted in a manner known per se into other salts of compounds of formula (I), acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula (I), which have salt-forming properties can be obtained in free form or in the form of salts.

The compounds of formula (I) and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula (I), in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula (I) with a suitable oxidizing agent, for example the H2O2/urea adduct in the presence of an acid anhydride, e.g. trifluoroacetic anhydride. Such oxidations are known from the literature, for example from J. Med. Chem., 32 (12), 2561-73, 1989 or WO200015615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

Tables 1 to 48 Compounds of Formula (Ia)

The invention is further illustrated by making available the following individual compounds of formula (Ia) listed below in Tables 1 to 48.

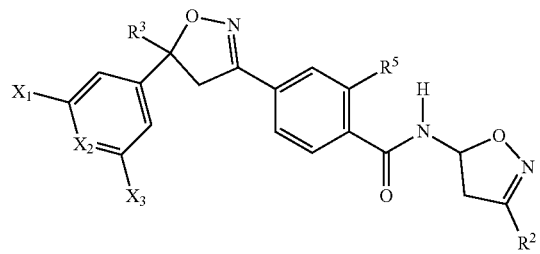
(Ia)

Each of Tables 1 to 48, which follow the Table P below, make available 250 compounds of the formula (Ia) in which $X^3$, $R^3$, $X^1$ and $R^5$ are the substituents defined in Table P and $R^2$ and $X^2$ are the substituents defined in the relevant Table 1 to 48. Thus Table 1 individualises 250 compounds of formula (Ia) wherein for each row of Table P, the $R^2$ and $X^2$ substituents are as defined in Table 1; similarly, Table 2 individualises 250 compounds of formula (Ia) wherein for each row of Table P, the $R^2$ and $X^2$ substituents are as defined in Table 2; and so on for Tables 3 to 48.

Each compound disclosed in Tables 1 to 48 represents a disclosure of a compound according to the compound of formula (I*), and a disclosure according to the compound of formula (I**) as well as mixtures thereof.

TABLE P

|    | $X^3$ | $R^3$ | $X^1$ | $R^5$ |
|----|-------|-------|-------|-------|
| 1  | H     | $CF_3$ | H    | $CH_3$ |
| 2  | Cl    | $CF_3$ | H    | $CH_3$ |
| 3  | Br    | $CF_3$ | H    | $CH_3$ |
| 4  | F     | $CF_3$ | H    | $CH_3$ |
| 5  | $CF_3$ | $CF_3$ | H   | $CH_3$ |
| 6  | H     | $CF_2Cl$ | H  | $CH_3$ |
| 7  | Cl    | $CF_2Cl$ | H  | $CH_3$ |
| 8  | Br    | $CF_2Cl$ | H  | $CH_3$ |
| 9  | F     | $CF_2Cl$ | H  | $CH_3$ |
| 10 | $CF_3$ | $CF_2Cl$ | H | $CH_3$ |
| 11 | H     | $CF_3$ | Cl   | $CH_3$ |
| 12 | Cl    | $CF_3$ | Cl   | $CH_3$ |
| 13 | Br    | $CF_3$ | Cl   | $CH_3$ |
| 14 | F     | $CF_3$ | Cl   | $CH_3$ |
| 15 | $CF_3$ | $CF_3$ | Cl  | $CH_3$ |
| 16 | H     | $CF_2Cl$ | Cl | $CH_3$ |
| 17 | Cl    | $CF_2Cl$ | Cl | $CH_3$ |
| 18 | Br    | $CF_2Cl$ | Cl | $CH_3$ |
| 19 | F     | $CF_2Cl$ | Cl | $CH_3$ |
| 20 | $CF_3$ | $CF_2Cl$ | Cl | $CH_3$ |
| 21 | H     | $CF_3$ | Br  | $CH_3$ |
| 22 | Cl    | $CF_3$ | Br  | $CH_3$ |
| 23 | Br    | $CF_3$ | Br  | $CH_3$ |
| 24 | F     | $CF_3$ | Br  | $CH_3$ |
| 25 | $CF_3$ | $CF_3$ | Br | $CH_3$ |
| 26 | H     | $CF_2Cl$ | Br | $CH_3$ |
| 27 | Cl    | $CF_2Cl$ | Br | $CH_3$ |
| 28 | Br    | $CF_2Cl$ | Br | $CH_3$ |
| 29 | F     | $CF_2Cl$ | Br | $CH_3$ |
| 30 | $CF_3$ | $CF_2Cl$ | Br | $CH_3$ |
| 31 | H     | $CF_3$ | F   | $CH_3$ |

TABLE P-continued

|     | $X^3$ | $R^3$ | $X^1$ | $R^5$ |
|-----|-------|-------|-------|-------|
| 32  | Cl    | $CF_3$ | F    | $CH_3$ |
| 33  | Br    | $CF_3$ | F    | $CH_3$ |
| 34  | F     | $CF_3$ | F    | $CH_3$ |
| 35  | $CF_3$ | $CF_3$ | F   | $CH_3$ |
| 36  | H     | $CF_2Cl$ | F  | $CH_3$ |
| 37  | Cl    | $CF_2Cl$ | F  | $CH_3$ |
| 38  | Br    | $CF_2Cl$ | F  | $CH_3$ |
| 39  | F     | $CF_2Cl$ | F  | $CH_3$ |
| 40  | $CF_3$ | $CF_2Cl$ | F | $CH_3$ |
| 41  | H     | $CF_3$ | $CF_3$ | $CH_3$ |
| 42  | Cl    | $CF_3$ | $CF_3$ | $CH_3$ |
| 43  | Br    | $CF_3$ | $CF_3$ | $CH_3$ |
| 44  | F     | $CF_3$ | $CF_3$ | $CH_3$ |
| 45  | $CF_3$ | $CF_3$ | $CF_3$ | $CH_3$ |
| 46  | H     | $CF_2Cl$ | $CF_3$ | $CH_3$ |
| 47  | Cl    | $CF_2Cl$ | $CF_3$ | $CH_3$ |
| 48  | Br    | $CF_2Cl$ | $CF_3$ | $CH_3$ |
| 49  | F     | $CF_2Cl$ | $CF_3$ | $CH_3$ |
| 50  | $CF_3$ | $CF_2Cl$ | $CF_3$ | $CH_3$ |
| 51  | H     | $CF_3$ | H    | Cl    |
| 52  | Cl    | $CF_3$ | H    | Cl    |
| 53  | Br    | $CF_3$ | H    | Cl    |
| 54  | F     | $CF_3$ | H    | Cl    |
| 55  | $CF_3$ | $CF_3$ | H   | Cl    |
| 56  | H     | $CF_2Cl$ | H  | Cl    |
| 57  | Cl    | $CF_2Cl$ | H  | Cl    |
| 58  | Br    | $CF_2Cl$ | H  | Cl    |
| 59  | F     | $CF_2Cl$ | H  | Cl    |
| 60  | $CF_3$ | $CF_2Cl$ | H | Cl    |
| 61  | H     | $CF_3$ | Cl   | Cl    |
| 62  | Cl    | $CF_3$ | Cl   | Cl    |
| 63  | Br    | $CF_3$ | Cl   | Cl    |
| 64  | F     | $CF_3$ | Cl   | Cl    |
| 65  | $CF_3$ | $CF_3$ | Cl  | Cl    |
| 66  | H     | $CF_2Cl$ | Cl | Cl    |
| 67  | Cl    | $CF_2Cl$ | Cl | Cl    |
| 68  | Br    | $CF_2Cl$ | Cl | Cl    |
| 69  | F     | $CF_2Cl$ | Cl | Cl    |
| 70  | $CF_3$ | $CF_2Cl$ | Cl | Cl    |
| 71  | H     | $CF_3$ | Br   | Cl    |
| 72  | Cl    | $CF_3$ | Br   | Cl    |
| 73  | Br    | $CF_3$ | Br   | Cl    |
| 74  | F     | $CF_3$ | Br   | Cl    |
| 75  | $CF_3$ | $CF_3$ | Br  | Cl    |
| 76  | H     | $CF_2Cl$ | Br | Cl    |
| 77  | Cl    | $CF_2Cl$ | Br | Cl    |
| 78  | Br    | $CF_2Cl$ | Br | Cl    |
| 79  | F     | $CF_2Cl$ | Br | Cl    |
| 80  | $CF_3$ | $CF_2Cl$ | Br | Cl    |
| 81  | H     | $CF_3$ | F    | Cl    |
| 82  | Cl    | $CF_3$ | F    | Cl    |
| 83  | Br    | $CF_3$ | F    | Cl    |
| 84  | F     | $CF_3$ | F    | Cl    |
| 85  | $CF_3$ | $CF_3$ | F   | Cl    |
| 86  | H     | $CF_2Cl$ | F  | Cl    |
| 87  | Cl    | $CF_2Cl$ | F  | Cl    |
| 88  | Br    | $CF_2Cl$ | F  | Cl    |
| 89  | F     | $CF_2Cl$ | F  | Cl    |
| 90  | $CF_3$ | $CF_2Cl$ | F | Cl    |
| 91  | H     | $CF_3$ | $CF_3$ | Cl    |
| 92  | Cl    | $CF_3$ | $CF_3$ | Cl    |
| 93  | Br    | $CF_3$ | $CF_3$ | Cl    |
| 94  | F     | $CF_3$ | $CF_3$ | Cl    |
| 95  | $CF_3$ | $CF_3$ | $CF_3$ | Cl    |
| 96  | H     | $CF_2Cl$ | $CF_3$ | Cl    |
| 97  | Cl    | $CF_2Cl$ | $CF_3$ | Cl    |
| 98  | Br    | $CF_2Cl$ | $CF_3$ | Cl    |
| 99  | F     | $CF_2Cl$ | $CF_3$ | Cl    |
| 100 | $CF_3$ | $CF_2Cl$ | $CF_3$ | Cl    |
| 101 | H     | $CF_3$ | H    | Br    |
| 102 | Cl    | $CF_3$ | H    | Br    |
| 103 | Br    | $CF_3$ | H    | Br    |
| 104 | F     | $CF_3$ | H    | Br    |
| 105 | $CF_3$ | $CF_3$ | H   | Br    |
| 106 | H     | $CF_2Cl$ | H  | Br    |
| 107 | Cl    | $CF_2Cl$ | H  | Br    |
| 108 | Br    | $CF_2Cl$ | H  | Br    |
| 109 | F     | $CF_2Cl$ | H  | Br    |

TABLE P-continued

| | X³ | R³ | X¹ | R⁵ |
|---|---|---|---|---|
| 110 | CF₃ | CF₂Cl | H | Br |
| 111 | H | CF₃ | Cl | Br |
| 112 | Cl | CF₃ | Cl | Br |
| 113 | Br | CF₃ | Cl | Br |
| 114 | F | CF₃ | Cl | Br |
| 115 | CF₃ | CF₃ | Cl | Br |
| 116 | H | CF₂Cl | Cl | Br |
| 117 | Cl | CF₂Cl | Cl | Br |
| 118 | Br | CF₂Cl | Cl | Br |
| 119 | F | CF₂Cl | Cl | Br |
| 120 | CF₃ | CF₂Cl | Cl | Br |
| 121 | H | CF₃ | Br | Br |
| 122 | Cl | CF₃ | Br | Br |
| 123 | Br | CF₃ | Br | Br |
| 124 | F | CF₃ | Br | Br |
| 125 | CF₃ | CF₃ | Br | Br |
| 126 | H | CF₂Cl | Br | Br |
| 127 | Cl | CF₂Cl | Br | Br |
| 128 | Br | CF₂Cl | Br | Br |
| 129 | F | CF₂Cl | Br | Br |
| 130 | CF₃ | CF₂Cl | Br | Br |
| 131 | H | CF₃ | F | Br |
| 132 | Cl | CF₃ | F | Br |
| 133 | Br | CF₃ | F | Br |
| 134 | F | CF₃ | F | Br |
| 135 | CF₃ | CF₃ | F | Br |
| 136 | H | CF₂Cl | F | Br |
| 137 | Cl | CF₂Cl | F | Br |
| 138 | Br | CF₂Cl | F | Br |
| 139 | F | CF₂Cl | F | Br |
| 140 | CF₃ | CF₂Cl | F | Br |
| 141 | H | CF₃ | CF₃ | Br |
| 142 | Cl | CF₃ | CF₃ | Br |
| 143 | Br | CF₃ | CF₃ | Br |
| 144 | F | CF₃ | CF₃ | Br |
| 145 | CF₃ | CF₃ | CF₃ | Br |
| 146 | H | CF₂Cl | CF₃ | Br |
| 147 | Cl | CF₂Cl | CF₃ | Br |
| 148 | Br | CF₂Cl | CF₃ | Br |
| 149 | F | CF₂Cl | CF₃ | Br |
| 150 | CF₃ | CF₂Cl | CF₃ | Br |
| 151 | H | CF₃ | H | CF₃ |
| 152 | Cl | CF₃ | H | CF₃ |
| 153 | Br | CF₃ | H | CF₃ |
| 154 | F | CF₃ | H | CF₃ |
| 155 | CF₃ | CF₃ | H | CF₃ |
| 156 | H | CF₂Cl | H | CF₃ |
| 157 | Cl | CF₂Cl | H | CF₃ |
| 158 | Br | CF₂Cl | H | CF₃ |
| 159 | F | CF₂Cl | H | CF₃ |
| 160 | CF₃ | CF₂Cl | H | CF₃ |
| 161 | H | CF₃ | Cl | CF₃ |
| 162 | Cl | CF₃ | Cl | CF₃ |
| 163 | Br | CF₃ | Cl | CF₃ |
| 164 | F | CF₃ | Cl | CF₃ |
| 165 | CF₃ | CF₃ | Cl | CF₃ |
| 166 | H | CF₂Cl | Cl | CF₃ |
| 167 | Cl | CF₂Cl | Cl | CF₃ |
| 168 | Br | CF₂Cl | Cl | CF₃ |
| 169 | F | CF₂Cl | Cl | CF₃ |
| 170 | CF₃ | CF₂Cl | Cl | CF₃ |
| 171 | H | CF₃ | Br | CF₃ |
| 172 | Cl | CF₃ | Br | CF₃ |
| 173 | Br | CF₃ | Br | CF₃ |
| 174 | F | CF₃ | Br | CF₃ |
| 175 | CF₃ | CF₃ | Br | CF₃ |
| 176 | H | CF₂Cl | Br | CF₃ |
| 177 | Cl | CF₂Cl | Br | CF₃ |
| 178 | Br | CF₂Cl | Br | CF₃ |
| 179 | F | CF₂Cl | Br | CF₃ |
| 180 | CF₃ | CF₂Cl | Br | CF₃ |
| 181 | H | CF₃ | F | CF₃ |
| 182 | Cl | CF₃ | F | CF₃ |
| 183 | Br | CF₃ | F | CF₃ |
| 184 | F | CF₃ | F | CF₃ |
| 185 | CF₃ | CF₃ | F | CF₃ |
| 186 | H | CF₂Cl | F | CF₃ |
| 187 | Cl | CF₂Cl | F | CF₃ |
| 188 | Br | CF₂Cl | F | CF₃ |
| 189 | F | CF₂Cl | F | CF₃ |
| 190 | CF₃ | CF₂Cl | F | CF₃ |
| 191 | H | CF₃ | CF₃ | CF₃ |
| 192 | Cl | CF₃ | CF₃ | CF₃ |
| 193 | Br | CF₃ | CF₃ | CF₃ |
| 194 | F | CF₃ | CF₃ | CF₃ |
| 195 | CF₃ | CF₃ | CF₃ | CF₃ |
| 196 | H | CF₂Cl | CF₃ | CF₃ |
| 197 | Cl | CF₂Cl | CF₃ | CF₃ |
| 198 | Br | CF₂Cl | CF₃ | CF₃ |
| 199 | F | CF₂Cl | CF₃ | CF₃ |
| 200 | CF₃ | CF₂Cl | CF₃ | CF₃ |
| 201 | H | CF₃ | H | F |
| 202 | Cl | CF₃ | H | F |
| 203 | Br | CF₃ | H | F |
| 204 | F | CF₃ | H | F |
| 205 | CF₃ | CF₃ | H | F |
| 206 | H | CF₂Cl | H | F |
| 207 | Cl | CF₂Cl | H | F |
| 208 | Br | CF₂Cl | H | F |
| 209 | F | CF₂Cl | H | F |
| 210 | CF₃ | CF₂Cl | H | F |
| 211 | H | CF₃ | Cl | F |
| 212 | Cl | CF₃ | Cl | F |
| 213 | Br | CF₃ | Cl | F |
| 214 | F | CF₃ | Cl | F |
| 215 | CF₃ | CF₃ | Cl | F |
| 216 | H | CF₂Cl | Cl | F |
| 217 | Cl | CF₂Cl | Cl | F |
| 218 | Br | CF₂Cl | Cl | F |
| 219 | F | CF₂Cl | Cl | F |
| 220 | CF₃ | CF₂Cl | Cl | F |
| 221 | H | CF₃ | Br | F |
| 222 | Cl | CF₃ | Br | F |
| 223 | Br | CF₃ | Br | F |
| 224 | F | CF₃ | Br | F |
| 225 | CF₃ | CF₃ | Br | F |
| 226 | H | CF₂Cl | Br | F |
| 227 | Cl | CF₂Cl | Br | F |
| 228 | Br | CF₂Cl | Br | F |
| 229 | F | CF₂Cl | Br | F |
| 230 | CF₃ | CF₂Cl | Br | F |
| 231 | H | CF₃ | F | F |
| 232 | Cl | CF₃ | F | F |
| 233 | Br | CF₃ | F | F |
| 234 | F | CF₃ | F | F |
| 235 | CF₃ | CF₃ | F | F |
| 236 | H | CF₂Cl | F | F |
| 237 | Cl | CF₂Cl | F | F |
| 238 | Br | CF₂Cl | F | F |
| 239 | F | CF₂Cl | F | F |
| 240 | CF₃ | CF₂Cl | F | F |
| 241 | H | CF₃ | CF₃ | F |
| 242 | Cl | CF₃ | CF₃ | F |
| 243 | Br | CF₃ | CF₃ | F |
| 244 | F | CF₃ | CF₃ | F |
| 245 | CF₃ | CF₃ | CF₃ | F |
| 246 | H | CF₂Cl | CF₃ | F |
| 247 | Cl | CF₂Cl | CF₃ | F |
| 248 | Br | CF₂Cl | CF₃ | F |
| 249 | F | CF₂Cl | CF₃ | F |
| 250 | CF₃ | CF₂Cl | CF₃ | F |

Table 1

Table 1 provides 250 compounds of formula (Ia) wherein $X^2$ is C—H, $R^2$ is $CH_3$, and $X^3$, $R^3$, $X^1$, $R^5$ are as defined in Table P.

Table 2

Table 2 provides 250 compounds of formula (Ia) wherein $X^2$ is C—Cl, $R^2$ is $CH_3$, and $X^3$, $R^3$, $X^1$, $R^5$ are as defined in Table P.

Table 3

Table 3 provides 250 compounds of formula (Ia) wherein $X^2$ is C—F, $R^2$ is $CH_3$, and $X^3$, $R^3$, $X^1$, $R^5$ are as defined in Table P.

Table 4
Table 4 provides 250 compounds of formula (Ia) wherein $X^2$ is N, $R^2$ is $CH_3$, and $X^3$, $R^3$, $X^1$, $R^5$ are as defined in Table P.
Table 5
Table 5 provides 250 compounds of formula (Ia) wherein $X^2$ is C—H, $R^2$ is $CH_2CH_3$, and $X^3$, $R^3$, $X^1$, $R^5$ are as defined in Table P.
Table 6
Table 6 provides 250 compounds of formula (Ia) wherein $X^2$ is C—Cl, $R^2$ is $CH_2CH_3$, and $X^3$, $R^3$, $X^1$, $R^5$ are as defined in Table P.
Table 7
Table 7 provides 250 compounds of formula (Ia) wherein $X^2$ is C—F, $R^2$ is $CH_2CH_3$, and $X^3$, $R^3$, $X^1$, $R^5$ are as defined in Table P.
Table 8
Table 8 provides 250 compounds of formula (Ia) wherein $X^2$ is N, $R^2$ is $CH_2CH_3$, and $X^3$, $R^3$, $X^1$, $R^5$ are as defined in Table P.
Table 9
Table 9 provides 250 compounds of formula (Ia) wherein $X^2$ is C—H, $R^2$ is $CF_3$, and $X^3$, $R^3$, $X^1$, $R^5$ are as defined in Table P.
Table 10
Table 10 provides 250 compounds of formula (Ia) wherein $X^2$ is C—Cl, $R^2$ is $CF_3$, and $X^3$, $R^3$, $X^1$, $R^5$ are as defined in Table P.
Table 11
Table 11 provides 250 compounds of formula (Ia) wherein $X^2$ is C—F, $R^2$ is $CF_3$, and $X^3$, $R^3$, $X^1$, $R^5$ are as defined in Table P.
Table 12
Table 12 provides 250 compounds of formula (Ia) wherein $X^2$ is N, $R^2$ is $CF_3$, and $X^3$, $R^3$, $X^1$, $R^5$ are as defined in Table P.
Table 13
Table 13 provides 250 compounds of formula (Ia) wherein $X^2$ is C—H, $R^2$ is cyclopropyl, and $X^3$, $R^3$, $X^1$, $R^5$ are as defined in Table P.
Table 14
Table 14 provides 250 compounds of formula (Ia) wherein $X^2$ is C—Cl, $R^2$ is cyclopropyl, and $X^3$, $R^3$, $X^1$, $R^5$ are as defined in Table P.
Table 15
Table 15 provides 250 compounds of formula (Ia) wherein $X^2$ is C—F, $R^2$ is cyclopropyl, and $X^3$, $R^3$, $X^1$, $R^5$ are as defined in Table P.
Table 16
Table 16 provides 250 compounds of formula (Ia) wherein $X^2$ is N, $R^2$ is cyclopropyl, and $X^3$, $R^3$, $X^1$, $R^5$ are as defined in Table P.
Table 17
Table 17 provides 250 compounds of formula (Ia) wherein $X^2$ is C—H, $R^2$ is $OCH_2CH_3$, and $X^3$, $R^3$, $X^1$, $R^5$ are as defined in Table P.
Table 18
Table 18 provides 250 compounds of formula (Ia) wherein $X^2$ is C—Cl, $R^2$ is $OCH_2CH_3$, and $X^3$, $R^3$, $X^1$, $R^5$ are as defined in Table P.
Table 19
Table 19 provides 250 compounds of formula (Ia) wherein $X^2$ is C—F, $R^2$ is $OCH_2CH_3$, and $X^3$, $R^3$, $X^1$, $R^5$ are as defined in Table P.
Table 20
Table 20 provides 250 compounds of formula (Ia) wherein $X^2$ is N, $R^2$ is $OCH_2CH_3$, and $X^3$, $R^3$, $X^1$, $R^5$ are as defined in Table P.
Table 21
Table 21 provides 250 compounds of formula (Ia) wherein $X^2$ is C—H, $R^2$ is $OCH_3$, and $X^3$, $R^3$, $X^1$, $R^5$ are as defined in Table P.
Table 22
Table 22 provides 250 compounds of formula (Ia) wherein $X^2$ is C—Cl, $R^2$ is $OCH_3$, and $X^3$, $R^3$, $X^1$, $R^5$ are as defined in Table P.
Table 23
Table 23 provides 250 compounds of formula (Ia) wherein $X^2$ is C—F, $R^2$ is $OCH_3$, and $X^3$, $R^3$, $X^1$, $R^5$ are as defined in Table P.
Table 24
Table 24 provides 250 compounds of formula (Ia) wherein $X^2$ is N, $R^2$ is $OCH_3$, and $X^3$, $R^3$, $X^1$, $R^5$ are as defined in Table P.
Table 25
Table 25 provides 250 compounds of formula (Ia) wherein $X^2$ is C—H, $R^2$ is Cl, and $X^3$, $R^3$, $X^1$, $R^5$ are as defined in Table P.
Table 26
Table 26 provides 250 compounds of formula (Ia) wherein $X^2$ is C—Cl, $R^2$ is Cl, and $X^3$, $R^3$, $X^1$, $R^5$ are as defined in Table P.
Table 27
Table 27 provides 250 compounds of formula (Ia) wherein $X^2$ is C—F, $R^2$ is Cl, and $X^3$, $R^3$, $X^1$, $R^5$ are as defined in Table P.
Table 28
Table 28 provides 250 compounds of formula (Ia) wherein $X^2$ is N, $R^2$ is Cl, and $X^3$, $R^3$, $X^1$, $R^5$ are as defined in Table P.
Table 29
Table 29 provides 250 compounds of formula (Ia) wherein $X^2$ is C—H, $R^2$ is Br, and $X^3$, $R^3$, $X^1$, $R^5$ are as defined in Table P.
Table 30
Table 30 provides 250 compounds of formula (Ia) wherein $X^2$ is C—Cl, $R^2$ is Br, and $X^3$, $R^3$, $X^1$, $R^5$ are as defined in Table P.
Table 31
Table 31 provides 250 compounds of formula (Ia) wherein $X^2$ is C—F, $R^2$ is Br, and $X^3$, $R^3$, $X^1$, $R^5$ are as defined in Table P.
Table 32
Table 32 provides 250 compounds of formula (Ia) wherein $X^2$ is N, $R^2$ is Br, and $X^3$, $R^3$, $X^1$, $R^5$ are as defined in Table P.
Table 33
Table 33 provides 250 compounds of formula (Ia) wherein $X^2$ is C—H, $R^2$ is F, and $X^3$, $R^3$, $X^1$, $R^5$ are as defined in Table P.
Table 34
Table 34 provides 250 compounds of formula (Ia) wherein $X^2$ is C—Cl, $R^2$ is F, and $X^3$, $R^3$, $X^1$, $R^5$ are as defined in Table P.
Table 35
Table 35 provides 250 compounds of formula (Ia) wherein $X^2$ is C—F, $R^2$ is F, and $X^3$, $R^3$, $X^1$, $R^5$ are as defined in Table P.
Table 36
Table 36 provides 250 compounds of formula (Ia) wherein $X^2$ is N, $R^2$ is F, and $X^3$, $R^3$, $X^1$, $R^5$ are as defined in Table P.

Table 37
Table 37 provides 250 compounds of formula (Ia) wherein $X^2$ is C—H, $R^2$ is $OCH_2CF_3$, and $X^3$, $R^3$, $X^1$, $R^5$ are as defined in Table P.
Table 38
Table 38 provides 250 compounds of formula (Ia) wherein $X^2$ is C—Cl, $R^2$ is $OCH_2CF_3$, and $X^3$, $R^3$, $X^1$, $R^5$ are as defined in Table P.
Table 39
Table 39 provides 250 compounds of formula (Ia) wherein $X^2$ is C—F, $R^2$ is $OCH_2CF_3$, and $X^3$, $R^3$, $X^1$, $R^5$ are as defined in Table P.
Table 40
Table 40 provides 250 compounds of formula (Ia) wherein $X^2$ is N, $R^2$ is $OCH_2CF_3$, and $X^3$, $R^3$, $X^1$, $R^5$ are as defined in Table P.
Table 41
Table 41 provides 250 compounds of formula (Ia) wherein $X^2$ is C—H, $R^2$ is $OCH_2CHF_2$, and $X^3$, $R^3$, $X^1$, $R^5$ are as defined in Table P.
Table 42
Table 42 provides 250 compounds of formula (Ia) wherein $X^2$ is C—Cl, $R^2$ is $OCH_2CHF_2$, and $X^3$, $R^3$, $X^1$, $R^5$ are as defined in Table P.
Table 43
Table 43 provides 250 compounds of formula (Ia) wherein $X^2$ is C—F, $R^2$ is $OCH_2CHF_2$, and $X^3$, $R^3$, $X^1$, $R^5$ are as defined in Table P.
Table 44
Table 44 provides 250 compounds of formula (Ia) wherein $X^2$ is N, $R^2$ is $OCH_2CHF_2$, and $X^3$, $R^3$, $X^1$, $R^5$ are as defined in Table P.
Table 45
Table 45 provides 250 compounds of formula (Ia) wherein $X^2$ is C—H, $R^2$ is $CH_2OCH_3$, and $X^3$, $R^3$, $X^1$, $R^5$ are as defined in Table P.
Table 46
Table 46 provides 250 compounds of formula (Ia) wherein $X^2$ is C—Cl, $R^2$ is $CH_2OCH_3$, and $X^3$, $R^3$, $X^1$, $R^5$ are as defined in Table P.
Table 47
Table 47 provides 250 compounds of formula (Ia) wherein $X^2$ is C—F, $R^2$ is $CH_2OCH_3$, and $X^3$, $R^3$, $X^1$, $R^5$ are as defined in Table P.
Table 48
Table 48 provides 250 compounds of formula (Ia) wherein $X^2$ is N, $R^2$ is $CH_2OCH_3$, and $X^3$, $R^3$, $X^1$, $R^5$ are as defined in Table P.

The present invention also provides intermediates useful for the preparation of compounds of formula (I). Certain intermediates are novel and as such form a further aspect of the invention. One group of novel intermediates are compounds of formula (Int-I)

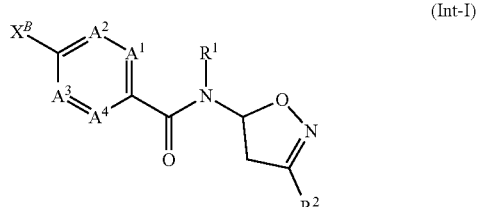

(Int-I)

wherein $A^1$, $A^2$, $A^3$, $A^4$, $R^1$ and $R^2$ are as defined for a compound of formula (I) and $X^B$ is a halogen, such as bromo, or $X^B$ is cyano, formyl, CH=N—OH or acetyl; or a salt or N-oxide thereof. The preferences for $A^1$, $A^2$, $A^3$, $A^4$, $R^1$ and $R^2$ are the same as the preferences set out for the corresponding substituents of a compound of formula (I).

Another group of novel intermediates are compounds of formula (Int-II)

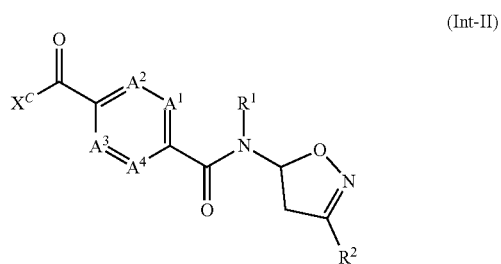

(Int-II)

wherein $A^1$, $A^2$, $A^3$, $A^4$, $R^1$ and $R^2$ are as defined for a compound of formula (I); $X^C$ is $CH_2$-halogen, wherein halogen is preferably. bromo or chloro, CH=C($R^3$)$R^4$ or $CH_2C(OH)(R^3)R^4$ wherein $R^3$ and $R^4$ are as defined for a compound of formula (I); or a salt or N-oxide thereof. The preferences for $A^1$, $A^2$, $A^3$, $A^4$, $R^1$ and $R^2$ are the same as the preferences set out for the corresponding substituents of a compound of formula (I).

Another group of novel intermediates are compounds of formula (Int-III)

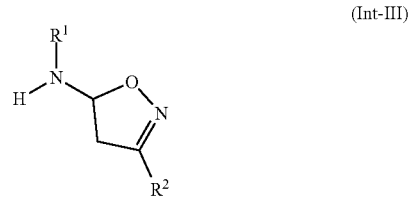

(Int-III)

wherein $R^1$ and $R^2$ are as defined for a compound of formula (I); or a salt or N-oxide thereof. The preferences for $R^1$ and $R^2$ are the same as the preferences set out for the corresponding substituents of a compound of formula (I).

Another group of novel intermediates are compounds of formula (Int-IV)

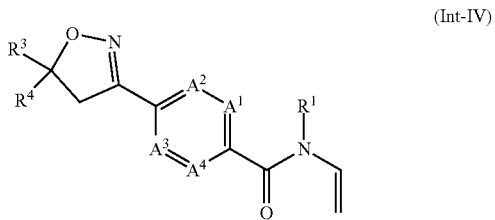

(Int-IV)

wherein $A^1$, $A^2$, $A^3$, $A^4$, $R^1$, $R^3$ and $R^4$ are as defined for a compound of formula (I) or a salt or N-oxide thereof. The preferences for $A^1$, $A^2$, $A^3$, $A^4$, $R^1$, $R^3$ and $R^4$ are the same as the preferences set out for the corresponding substituents of a compound of formula (I).

Examples of compounds of formula (Int-I) made available are those where $X^B$ is bromo, chloro, iodo, cyano, formyl, CH=NOH or acetyl, $A^2$, $A^3$ and $A^4$ are each CH, $R^1$ is hydrogen, $A^1$ is $CR^5$, and wherein $R^2$ corresponds to a substitutent $R^2$ as defined in each of Tables 1 to 48 above in context of formula (Ia), So for example, Table 1 individualises a compound of formula (Int-I) wherein $X^B$ is bromo, chloro, iodo, cyano, formyl, CH=NOH or acetyl, $A^2$, $A^3$ and $A^4$ are each CH, $R^1$ is hydrogen, $A^1$ is $CR^5$, and wherein $R^2$ is as defined in Table 1.

Examples of compounds of formula (Int-II) made available are those where $X^c$ is $CH_2Cl$, $CH_2Br$, CH=C($CF_3$)(3-chloro-5-trifluoromethyl-phenyl), CH=C($CF_3$)(3-bromo-5-trifluoromethyl-phenyl), CH=C($CF_3$)(4-fluoro-3,5-dichlorophenyl), CH=C($CF_3$)(3,4,5-trichloro-phenyl), CH=C($CF_3$)(3,5-dichloro-phenyl), $CH_2C(OH)(CF_3)$(3-chloro-5-trifluoromethyl-phenyl), $CH_2C(OH)(CF_3)$(3-bromo-5-trifluoromethyl-phenyl), $CH_2C(OH)$(—$CF_3$)(3,5-dichlorophenyl), $CH_2C(OH)(CF_3)$(4-fluoro-3,5-dichlorophenyl) or $CH_2C(OH)(CF_3)$(3,4,5-trichloro-phenyl), $A^2$, $A^3$ and $A^4$ are each CH, $R^1$ is hydrogen, $A^1$ is $CR^5$, and wherein $R^2$ is as defined in each of Tables 1 to 48 above in context of formula (Ia), So for example, Table 1 individualises a compound of formula (Int-II) wherein $X^c$ is $CH_2Cl$, $CH_2Br$, CH=C($CF_3$)(3-chloro-5-trifluoromethyl-phenyl), CH=C($CF_3$)(3-bromo-5-trifluoromethyl-phenyl), CH=C($CF_3$)(4-fluoro-3,5-dichlorophenyl), CH=C($CF_3$)(3,4,5-trichloro-phenyl), CH=C($CF_3$)(3,5-dichloro-phenyl), $CH_2C(OH)(CF_3)$(3-chloro-5-trifluoromethyl-phenyl), $CH_2C(OH)(CF_3)$(3-bromo-5-trifluoromethyl-phenyl), $CH_2C(OH)(CF_3)$(3,5-dichloro-phenyl), $CH_2C(OH)(CF_3)$(4-fluoro-3,5-dichlorophenyl) or $CH_2C(OH)(CF_3)$(3,4,5-trichloro-phenyl), $A^2$, $A^3$ and $A^4$ are each CH, $R^1$ is hydrogen, $A^1$ is $CR^5$, and wherein $R^2$ is as defined in Table 1.

Examples of compounds of formula (Int-III) made available are those where $R^1$ is hydrogen and wherein $R^2$ corresponds to a substitutent $R^2$ as defined in each of Tables 1 to 48 above in context of formula (Ia), So for example, Table 1 individualises a compound of formula (Int-III) wherein $R^1$ is hydrogen, and wherein $R^2$ is as defined in Table 1.

Examples of compounds of formula (Int-IV) made available are those where $A^2$, $A^3$ and $A^4$ are each CH, $R^1$ is hydrogen, $A^1$ is $CR^5$, and wherein $R^3$, $X^1$, $X^2$ and $X^3$ corresponds to a substitutent $R^3$, $X^1$, $X^2$ and $X^3$ as defined in each of Tables 1 to 48 above in context of formula (Ia), So for example, Table 1 individualises a compound of formula (Int-IV) wherein $A^2$, $A^3$ and $A^4$ are each CH, $R^1$ is hydrogen, $A^1$ is $CR^5$, and wherein $R^3$, $X^1$, $X^2$ and $X^3$ is as defined in Table 1.

The compounds of formula (I) according to the invention are preventively and/or curatively valuable active ingredients in the field of pest control, even at low rates of application, which have a very favorable biocidal spectrum and are well tolerated by warm-blooded species, fish and plants. The pests which may be combated and controlled by the use of the compounds of the invention include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,

*Acalitus* spp., *Aculus* spp., *Acaricalus* spp., *Aceria* spp., *Acarus siro*, *Amblyomma* spp., *Argas* spp., *Boophilus* spp., *Brevipalpus* spp., *Bryobia* spp, *Calipitrimerus* spp., *Chorioptes* spp., *Derma-nyssus gallinae*, *Dermatophagoides* spp., *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.; from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*; *Acyrthosium pisum*, *Adalges* spp, *Agalliana ensigera*, *Agonoscena targionii*, *Aleurodicus* spp,

*Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*,

*Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maid is*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris;* from the order Hymenoptera, for example,

*Acromyrmex*, *Arge* spp., *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Gra-pholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypi-ela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order Thysanura, for example, *Lepisma saccharina*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, *asparagus*, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis*, *Anthemis* spp., *Antirrhinum* spp., *Aster* spp., *Begonia* spp. (e.g. *B. elatior*, *B. semperflorens*, *B. tubéreux*), *Bougainvillea* spp., *Brachycome* spp., *Brassica* spp. (ornamental), *Calceolaria* spp., *Capsicum annuum*, *Catharanthus roseus*, *Canna* spp., *Centaurea* spp., *Chrysanthemum* spp., *Cineraria* spp. (*C. maritime*), *Coreopsis* spp., *Crassula coccinea*, *Cuphea ignea*, *Dahlia* spp., *Delphinium* spp., *Dicentra spectabilis*, *Dorotheantus* spp., *Eustoma grandiflorum*, *Forsythia* spp., *Fuchsia* spp., *Geranium gnaphalium*, *Gerbera* spp., *Gomphrena globosa*, *Heliotropium* spp., *Helianthus* spp., *Hibiscus* spp., *Hortensia* spp., *Hydrangea* spp., *Hypoestes phyllostachya*, *Impatiens* spp. (*I. Walleriana*), *Iresines* spp., *Kalanchoe* spp., *Lantana camara*, *Lavatera trimestris*, *Leonotis leonurus*, *Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum*, *P. Zonale*), *Viola* spp. (pansy), *Petunia* spp., *Phlox* spp., *Plecthranthus* spp., *Poinsettia* spp., *Parthenocissus* spp. (*P. quinquefolia*, *P. tricuspidata*),

*Primula* spp., *Ranunculus* spp., *Rhododendron* spp., *Rosa* spp. (*rose*), *Rudbeckia* spp., *Saintpaulia* spp., *Salvia* spp., *Scaevola aemola*, *Schizanthus wisetonensis*, *Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba*.

Preferred ornamental species include African violet, Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); *ochlodina*; *Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides*.

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO2008151984, WO2003034823, U.S. Pat. No. 5,631,072, WO2005064072, WO2006128870, EP1724392, WO2005113886 or WO2007090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables X and Y:

TABLE X

Examples of exotic woodborers of economic importance.

| Family | Species | Host or Crop Infested |
| --- | --- | --- |
| Buprestidae | *Agrilus planipennis* | Ash |
| Cerambycidae | *Anoplura glabripennis* | Hardwoods |
| Scolytidae | *Xylosandrus crassiusculus* | Hardwoods |
|  | *X. mutilatus* | Hardwoods |
|  | *Tomicus piniperda* | Conifers |

TABLE Y

Examples of native woodborers of economic importance.

| Family | Species | Host or Crop Infested |
| --- | --- | --- |
| Buprestidae | *Agrilus anxius* | Birch |
|  | *Agrilus politus* | Willow, Maple |
|  | *Agrilus sayi* | Bayberry, Sweetfern |
|  | *Agrilus vittaticolllis* | Apple, Pear, Cranberry, Serviceberry, Hawthorn |
|  | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
|  | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
|  | *Goes tigrinus* | Oak |
|  | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
|  | *Neoptychodes trilineatus* | Fig, Alder, Mulberry, Willow, Netleaf hackberry |
|  | *Oberea ocellata* | Sumac, Apple, Peach, Plum, Pear, Currant, Blackberry |

TABLE Y-continued

Examples of native woodborers of economic importance.

| Family | Species | Host or Crop Infested |
|---|---|---|
| | Oberea tripunctata | Dogwood, *Viburnum*, Elm, Sourwood, Blueberry, *Rhododendron*, Azalea, Laurel, Poplar, Willow, Mulberry |
| | Oncideres cingulata | Hickory, Pecan, Persimmon, Elm, Sourwood, Basswood, Honeylocust, Dogwood, *Eucalyptus*, Oak, Hackberry, Maple, Fruit trees |
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, *Viburnum*, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp.,

*Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp.*, *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, water-soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha. Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%

Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

The activity of the compositions according to the invention can be broadened considerably, and adapted to prevailing circumstances, by adding other insecticidally, acaricidally and/or fungicidally active ingredients. The mixtures of the compounds of formula (I) with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula (I) with active ingredients are preferred (the abbreviation "TX" means "one compound selected from the group consisting of the compounds described in Tables 1 to 48 and Table A of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure Bi (alternative name) (839)+TX, trimedlure B2

(alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, Bacillus thuringiensis delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, 0,0,0',0'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, aceprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium* verrucaria composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxicon-azole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoximmethyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzo-lar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX,1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX; lancotrione [1486617-21-3]+TX; florpyrauxifen [943832-81-3]+TX; ipfentrifluconazole [1417782-08-1]+TX; mefentrifluconazole [1417782-03-6]+TX; quinofumelin [861647-84-9]+TX; chloroprallethrin [399572-87-3]+TX; cyhalodiamide [1262605-53-7]+TX; fluazaindolizine [1254304-22-7]+TX; fluxametamide [928783-29-3]+TX; epsilon-metofluthrin [240494-71-7]+TX; epsilon-momfluorothrin [1065124-65-3]+TX; pydiflumetofen [1228284-64-7]+TX; kappa-bifenthrin [439680-76-9]+TX; broflanilide [1207727-04-5]+TX; dicloromezotiaz [1263629-39-5]+TX; dipymetitrone [16114-35-5]+TX; pyraziflumid [942515-63-1]+TX; and kappa-tefluthrin [391634-71-2]+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis Cry* 2Ae+TX, *Bacillus thuringiensis* CrylAb+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis* kurstaki HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain 0+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium vixens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecaniciffium longisporum* (Vertiblast®)+TX, *Lecaniciffium muscarium*

(Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botanic®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (*Aphelinus*-System®)+TX, *Acerophagus papaya*+TX, *Adalia bipunctata* (*Adalia*-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX,

*Andersoni*-System®)+TX, *Amblyseius califomicus* (Amblyline®)+TX, Spical®)+TX, *Amblyseius cucumeris* (Thripex®+TX, *Bugline cucumeris*®)+TX, *Amblyseius fallacis* (Fallacis®)+TX, *Amblyseius swirskii* (Bugline swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (Dac-Digline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus califomicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (Harmo-Beetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®))+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®))+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (*Podisus*®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinemema carpocapsae* (Nematac C®+TX, Millenium®+TX, BioNem C®+TX, NemAttack®+TX, Nemastar®+TX, Capsanem®)+TX, *Steinememia feltiae* (NemaShield®+TX, Nemasys F®+TX, BioNem F®+TX, *Steinernema*-System®)+TX, NemAttack®+TX, Nemaplus®+TX, Exhibitline sf®+TX, Sciarid®+TX, Entonem®)+TX, *Steinememia kraussei* (Nemasys L®+TX, BioNem L®+TX, Exhibitline Srb®)+TX, *Steinememia riobrave* (BioVector®+TX, BioVektor®)+TX, *Steinememia scapterisci* (Nematac S®)+TX, *Steinememia* spp.+TX, *Steinememiatid* spp. (Guardian Nematodes®)+TX, *Stethorus punctillum* (*Stethorus*®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Callego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (SD-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula (I) selected from Tables 1 to 48 and Table A with active ingredients described above comprises a compound selected from Tables 1 to 48 and Table A and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula (I) selected from Tables 1 to 48 and Table A and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) selected from Tables 1 to 48 and Table A and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula (I). The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

The invention further relates to a pesticidal composition, which comprises at least one compound of formula (I) according to this invention or at least one compound of formula (Ib) or, where appropriate, a tautomer thereof, in each case in free form or in agrochemically utilizable salt form, as active ingredient.

The invention further relates to a method for controlling pests, which comprises applying a composition according to the invention to the pests or their environment preferably with the exception of a method for treatment of the human or animal body by surgery or therapy and diagnostic methods practised on the human or animal body.

The invention further relates to a method for the protection of plant propagation material from the attack by pests, which comprises treating the propagation material or the site, where the propagation material is planted, with a composition comprising a compound according to this invention or with a compound according to this invention. The invention further relates to a plant propagation material treated with the pesticidal composition comprising a compound according to this invention or with a compound according to this invention.

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.8 ppm.

PREPARATORY EXAMPLES

"Mp" means melting point in ° C. Free radicals represent methyl groups. H NMR measurements were recorded on a Brucker 400 MHz spectrometer, chemical shifts are given in ppm relevant to a TMS standard. Spectra measured in deuterated solvents as indicated.

The following LC-MS methods were used to characterize the compounds:

Method A

| | |
|---|---|
| MS | Spectra were recorded on a Mass Spectrometer from Waters (SQD or SQDII Single quadrupole mass spectrometer) equipped with an electrospray source (Polarity: positive or negative ions, Capillary: 3.00 kV, Cone range: 30 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da). |
| LC | Acquity UPLC from Waters: Binary pump, heated column compartment and diode-array detector. Solvent degasser, binary pump, heated column compartment and diode-array detector. Column: Waters UPLC HSS T3, 1.8 μm, 30 × 2.1 mm, Temp: 60° C., DAD Wavelength range (nm): 210 to 500, Solvent Gradient: A = water + 5% MeOH + 0.05% HCOOH, B = Acetonitrile + 0.05% HCOOH: gradient: 0 min 0% B, 100% A; 1.2-1.5 min 100% B; Flow (ml/min) 0.85. |

Method B

| | |
|---|---|
| MS | Spectra were recorded on a Mass Spectrometer from Waters (SQD or SQDII Single quadrupole mass spectrometer) equipped with an electrospray source (Polarity: positive or negative ions, Capillary: 3.00 kV, Cone range: 45 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da). |
| LC | Acquity UPLC from Waters: Binary pump, heated column compartment and diode-array detector. Solvent degasser, binary pump, heated column compartment and diode-array detector. Column: Waters UPLC HSS T3, 1.8 μm, 30 × 2.1 mm, Temp: 60° C., DAD Wavelength range (nm): 210 to 500, Solvent Gradient: A = water + 5% MeOH + 0.05% HCOOH, B = Acetonitrile + 0.05% HCOOH: gradient: 0 min 0% B, 100% A; 1.2-1.5 min 100% B; Flow (ml/min) 0.85. |

Method C

| | |
|---|---|
| MS | Spectra were recorded on a Mass Spectrometer from Waters (SQD, SQDII Single quadrupole mass spectrometer) equipped with an electrospray source (Polarity: positive and negative ions), Capillary: 3.00 kV, Cone range: 30 V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) |
| LC | Acquity UPLC from Waters: Binary pump, heated column compartment, diode-array detector and ELSD detector. Column: Waters UPLC HSS T3, 1.8 μm, 30 × 2.1 mm, Temp: 60° C., DAD Wavelength range (nm): 210 to 500, Solvent Gradient: A = water + 5% MeOH + 0.05% HCOOH, B = Acetonitrile + 0.05% HCOOH, gradient: 10-100% B in 2.7 min; Flow (ml/min) 0.85 |

Example 1: 4-[(5S)-5-(3,5-dichloro-4-fluoro-phenyl)-5-(trifluoromethyl)-4H-isoxazol-3-yl]-N-formyl-2-methyl-N-vinyl-benzamide

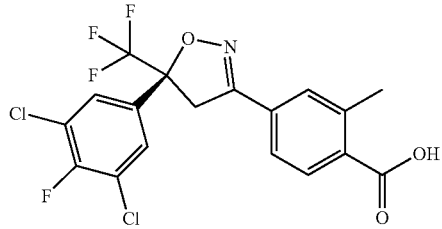

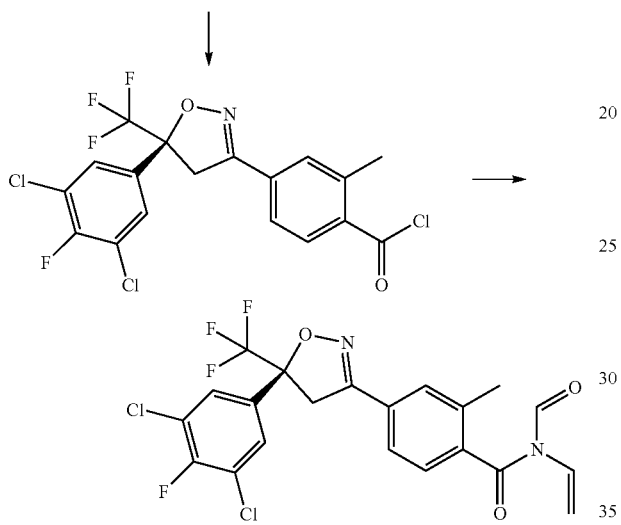

Step 1:
To a suspension of 20 g 4-[(5S)-5-(3,5-dichloro-4-fluoro-phenyl)-5-(trifluoromethyl)-4H-isoxazol-3-yl]-2-methyl-benzoic acid in 120 ml dichloromethane were added 5.0 mL oxalyl dichloride and 5 drops of N,N-dimethylformamide. The resulting mixture was stirred at ambient temperature for 5 hours. Then, an additional 1.9 mL of oxalyl dichloride was added and the resulting mixture was stirred at ambient temperature for 21 hours. The solvent was evaporated to give 21.2 g of 4-[(5S)-5-(3,5-dichloro-4-fluoro-phenyl)-5-(trifluoromethyl)-4H-isoxazol-3-yl]-2-methyl-benzoyl chloride, which was used for the next step without further purification.

Step 2:
A solution of N-vinylformamide (1.61 mL) and triethylamine (4.65 mL) in Dichloromethane (40.0 mL) was stirred at room temperature then 4-(Dimethylamino)pyridine (0.271 g) were added. The clear colorless solution was stirred and cooled to 0-5° C. for 5 minutes. To this solution, a solution of 4-[(5S)-5-(3,5-dichloro-4-fluoro-phenyl)-5-(trifluoromethyl)-4H-isoxazol-3-yl]-2-methyl-benzoyl chloride obtained in step 1 (10 g) in Dichloromethane (40.0 mL) was added dropwise. After stirring for 15 minutes, the reaction mixture was stirred at ambient temperature for 19 hours. Then the mixture was extracted between Dichloromethane and water. The combined organic layers were dried over anhydrous magnesium sulfate, filtered and evaporated to give a crude residue, which was then purified by column chromatography on silica gel using using ethyl acetate/Cyclohexane (from 0:100 to 50:50) as a solvent.

Thus, 6.8 g of 4-[(5S)-5-(3,5-dichloro-4-fluoro-phenyl)-5-(trifluoromethyl)-4H-isoxazol-3-yl]-N-formyl-2-methyl-N-vinyl-benzamide was obtained.

1H-NMR (CDCl3, 400 MHz, δ in ppm): 2.41 (s, 3H) 3.70 (d, J=17.2 Hz, 1H) 4.08-4.12 (d, 1H) 5.20-5.22 (m, 1H) 5.68 (d, J=16.1 Hz, 1H) 6.67-6.78 (m, 1H) 7.39 (d, J=8.1 Hz, 1H) 7.53-7.68 (m, 4H) 8.95 (s, 1H)

Example 2a: N-(3-bromo-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide (Compound A002 in Table A)

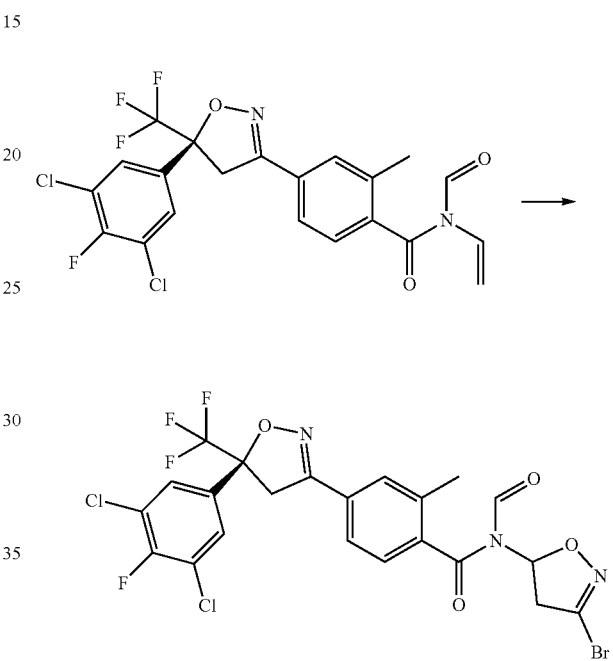

To a solution of 4-[(5S)-5-(3,5-dichloro-4-fluoro-phenyl)-5-(trifluoromethyl)-4H-isoxazol-3-yl]-N-formyl-2-methyl-N-vinyl-benzamide (1.0 g) in Ethylacetate (10 mL) was added a saturated solution of sodium hydrogencarbonate (10 mL). After 5 minutes at room temperature, 500 mg of Dibromoformaldoxime (prepared as described in the literature: Chemical Communications, 2010, p. 8475-8477) was added in 4 portions over 15 min. The reaction mixture was stirred at ambient temperature for 3.5 hours then more Dibromoformaldoxime (125 mg) was added. The reaction mixture was stirred at ambient temperature for 2 hours then it was extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 50:50) as a solvent. Thus, 1.02 g of N-(3-bromo-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide was obtained.

1H-NMR (CDCl3, 400 MHz, δ in ppm): 2.41 (s, 3H) 3.45-3.61 (m, 2H) 3.70 (d, J=17.24 Hz, 1H) 4.04-4.14 (m, 1H) 6.80-6.90 (m, 1H) 7.40 (d, J=8.07 Hz, 1H) 7.53-7.70 (m, 4H) 8.66 (s, 1H)

Example 2b: 4-[(5S)-5-(3,5-dichloro-4-fluoro-phenyl)-5-(trifluoromethyl)-4H-isoxazol-3-yl]-N-formyl-2-methyl-N-[3-(trifluoromethyl)-4,5-dihydroisoxazol-5-yl]benzamide (Compound A004 in Table A)

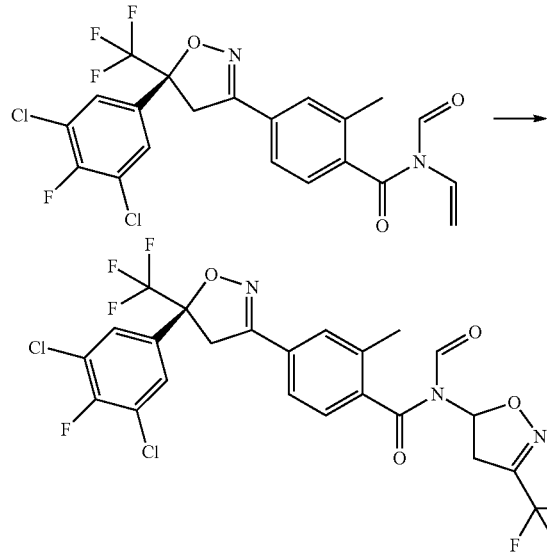

To a solution of 4-[(5S)-5-(3,5-dichloro-4-fluoro-phenyl)-5-(trifluoromethyl)-4H-isoxazol-3-yl]-N-formyl-2-methyl-N-vinyl-benzamide (200 mg) in Ethylacetate (4.1 mL) was added sodium hydrogencarbonate (150 mg). After 5 minutes at room temperature, a solution of 2,2,2-trifluoro-N-hydroxyacetimidoyl bromide (ca 391 mmol, prepared as described in the literature: WO2010014257) in diethyl ether was added. The reaction mixture was stirred at ambient temperature for 22 hours then was warmed to 60 C for 3 h30. The reaction mixture was then cooled to ambient temperature and stirred over 72 hours. It was then extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 100:0) as a solvent. Thus, 126 mg of 4-[(5S)-5-(3,5-dichloro-4-fluoro-phenyl)-5-(trifluoromethyl)-4H-isoxazol-3-yl]-N-formyl-2-methyl-N-[3-(trifluoromethyl)-4,5-dihydroisoxazol-5-yl]benzamide was obtained.

1H-NMR (CDCl3, 400 MHz, δ in ppm): 2.41 (s, 3H) 3.50 (d, J=7.3 Hz, 2H) 3.70 (d, J=17.2 Hz, 1H) 4.10 (d, J=16.9 Hz, 1H) 7.06 (dd, J=9.3, 6.8 Hz, 1H) 7.40 (d, J=7.7 Hz, 1H) 7.53-7.70 (m, 4H) 8.65 (s, 1H)

Example 2c: ethyl 5-[[4-[(5S)-5-(3,5-dichloro-4-fluoro-phenyl)-5-(trifluoromethyl)-4H-isoxazol-3-yl]-2-methyl-benzoyl]-formyl-amino]-4,5-dihydroisoxazole-3-carboxylate (Compound A006 in Table A)

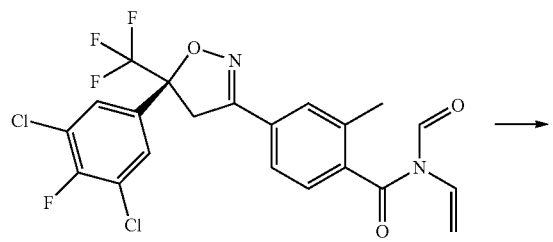

-continued

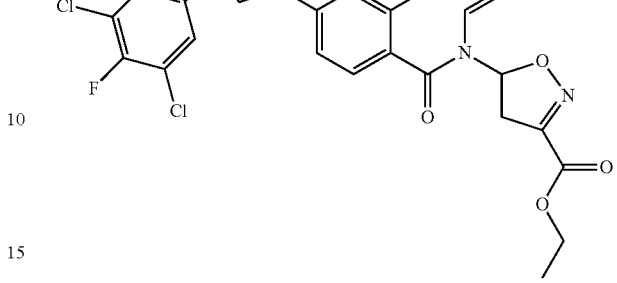

To a solution of 4-[(5S)-5-(3,5-dichloro-4-fluoro-phenyl)-5-(trifluoromethyl)-4H-isoxazol-3-yl]-N-formyl-2-methyl-N-vinyl-benzamide (430 mg) in Ethylacetate (7 mL) was added ethyl (2E)-2-chloro-2-hydroxyimino-acetate (200 mg). To this mixture was added Sodium hydrogencarbonate (330 mg) and the resulting mixture was stirred at ambient temperature for 19 hours. Then additional amount of ethyl (2E)-2-chloro-2-hydroxyimino-acetate (200 mg) was added and the mixture was warmed to 60 C for 8 hours. The reaction mixture was then cooled to ambient temperature it was extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 30:70) as a solvent. The isolate compound was then suspended in 5 ml of pentane and the suspension was stirred for 20 minutes. It was then filtered and the solid was dried under vacuo to give 412 mg of ethyl 5-[[4-[(5S)-5-(3,5-dichloro-4-fluoro-phenyl)-5-(trifluoromethyl)-4H-isoxazol-3-yl]-2-methyl-benzoyl]-formyl-amino]-4,5-dihydroisoxazole-3-carboxylate. 1H-NMR (CDCl3, 400 MHz, δ in ppm): 1.39-1.42 (m, 3H) 2.41 (s, 3H) 3.42-3.60 (m, 2H) 3.70 (d, J=17.6 Hz, 1H) 4.10 (d, J=17.2 Hz, 1H) 4.40 (q, J=7.1 Hz, 2H) 6.94-7.05 (m, 1H) 7.40 (d, J=8.1 Hz, 1H) 7.53-7.69 (m, 4H) 8.64 (s, 1H)

Example 2d: N-(3-chloro-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide (Compound A011 in Table A)

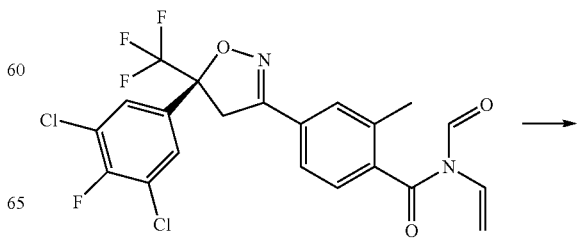

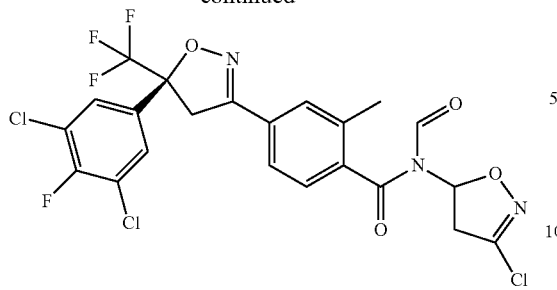

To a solution of 4-[(5S)-5-(3,5-dichloro-4-fluoro-phenyl)-5-(trifluoromethyl)-4H-isoxazol-3-yl]-N-formyl-2-methyl-N-vinyl-benzamide (500 mg) in Ethylacetate (5 mL) was added a saturated solution of sodium hydrogencarbonate (5 mL). After 5 minutes of stirring at room temperature, a solution of dichloroformaldoxime (1 mL, 0.91 mol/L in dimethoxyethane, prepared as described in the literature: Chemical Communications, 2010, p. 8475-8477) was added in 2 portions over 30 min. The reaction mixture was stirred at ambient temperature for 7 hours then more sodium hydrogencarbonate (700 mg) was added, followed by a solution of dichloroformaldoxime (1 mL, 0.91 mol/L in dimethoxyethane, prepared as described in the literature: Chemical Communications, 2010, p. 8475-8477) was added in 2 portions in 5 hours. The reaction mixture was stirred at ambient temperature for 2 hours then it was extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 50:50) as a solvent. Thus, 428 mg of N-(3-chloro-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide was obtained.

1H-NMR (CDCl3, 400 MHz, δ in ppm): 2.41 (s, 3H) 3.39-3.59 (m, 2H) 3.70 (d, J=17.2 Hz, 1H) 4.10 (d, J=17.2 Hz, 1H) 6.91-6.95 (dd, J=5.5 Hz, 1H) 7.40 (d, J=7.7 Hz, 1H) 7.53-7.69 (m, 4H) 8.66 (s, 1H)

Using a similar procedure, N-(3-chloro-4,5-dihydroisoxazol-5-yl)-N-formyl-2-methyl-4-[(5S)-5-(3,4,5-trichloro-phenyl)-5-(trifluoromethyl)-4H-isoxazol-3-yl]benzamide was prepared (compound A010 in table A):

1H-NMR (CDCl3, 400 MHz, δ in ppm): 2.41 (s, 3H) 3.40-3.59 (m, 2H) 3.70 (d, J=17.2 Hz, 1H) 4.04-4.14 (m, 1H) 6.85-6.97 (m, 1H) 7.40 (d, J=8.1 Hz, 1H) 7.60-7.67 (m, 4H) 8.66 (s, 1H)

Example 2e: 4-[(5S)-5-(3,5-dichloro-4-fluoro-phenyl)-5-(trifluoromethyl)-4H-isoxazol-3-yl]-N-formyl-2-methyl-N-(3-methyl-4,5-dihydroisoxazol-5-yl)benzamide (Compound A008 in Table A) and 4-[(5S)-5-(3,5-dichloro-4-fluoro-phenyl)-5-(trifluoromethyl)-4H-isoxazol-3-yl]-2-methyl-N-(3-methyl-4,5-dihydroisoxazol-5-yl)benzamide (Compound A009 in Table A)

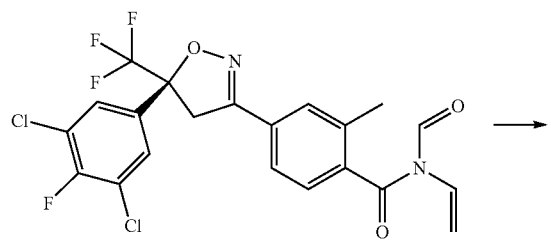

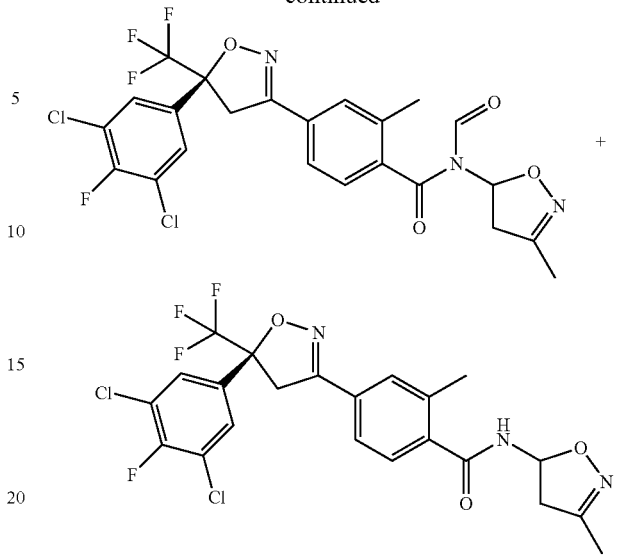

To a solution of N-Chlorosuccinimide (0.55 g) in N,N-Dimethylformamide (12 mL) was added Acetaldyde oxime (240 mg) and the solution was stirred at ambient temperature for 3 h. Then a solution of 4-[(5S)-5-(3,5-dichloro-4-fluoro-phenyl)-5-(trifluoromethyl)-4H-isoxazol-3-yl]-N-formyl-2-methyl-N-vinyl-benzamide (0.40 g) and Triethylamine (0.58 mL) in N,N-Dimethylformamide (2.0 mL) were added dropwise. The reaction was further stirred at ambient temperature for 24 hours. The reaction was then warmed to 60° C. for 4 hours. A solution of N-Chlorosuccinimide (0.55 g) dissolved in N,N-Dimethylformamide (12 mL) with acetaldyde oxime (0.24 g) was stirred at ambient temperature for 3 h in a separate vessel and then 2 mL of this solution was added to the reaction mixture. It was further stirred at 60° C. for 3 hours and then stirred at ambient temperature for 16 hours. The reaction mixture was then extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 100:0) as a solvent to give two compounds separately: 138 mg of 4-[(5S)-5-(3,5-dichloro-4-fluoro-phenyl)-5-(trifluoromethyl)-4H-isoxazol-3-yl]-N-formyl-2-methyl-N-(3-methyl-4,5-dihydroisoxazol-5-yl) benzamide were obtained along with 219 mg of 4-[(5S)-5-(3,5-dichloro-4-fluoro-phenyl)-5-(trifluoromethyl)-4H-isoxazol-3-yl]-2-methyl-N-(3-methyl-4,5-dihydroisoxazol-5-yl)benzamide. 4-[(5S)-5-(3,5-dichloro-4-fluoro-phenyl)-5-(trifluoromethyl)-4H-isoxazol-3-yl]-N-formyl-2-methyl-N-(3-methyl-4,5-dihydroisoxazol-5-yl)benzamide:

1H-NMR (CDCl3, 400 MHz, δ in ppm): 2.12 (s, 3H) 2.41 (s, 3H) 3.28 (d, J=7.7 Hz, 2H) 3.70 (d, J=17.2 Hz, 1H) 4.10 (d, J=17.2 Hz, 1H) 6.72-6.87 (m, 1H) 7.40 (d, J=7.7 Hz, 1H) 7.51-7.69 (m, 4H) 8.66 (s, 1H)

4-[(5S)-5-(3,5-dichloro-4-fluoro-phenyl)-5-(trifluoromethyl)-4H-isoxazol-3-yl]-2-methyl-N-(3-methyl-4,5-dihydroisoxazol-5-yl)benzamide: 1H-NMR (CDCl3, 400 MHz, δ in ppm): 2.08 (s, 3H) 2.49 (s, 3H) 2.84-2.92 (m, 1H) 3.39 (dd, J=18.2, 7.9 Hz, 1H) 3.69 (d, J=17.2 Hz, 1H) 4.09 (d, J=17.2 Hz, 1H) 6.38-6.46 (m, 2H) 7.42-7.44 (m, 1H) 7.49-7.55 (m, 2H) 7.59 (d, J=5.9 Hz, 2H)

Using a similar procedure, N-formyl-2-methyl-N-(3-methyl-4,5-dihydroisoxazol-5-yl)-4-[(5S)-5-(3,4,5-trichlorophenyl)-5-(trifluoromethyl)-4H-isoxazol-3-yl]benzamide (compound A023 in table A) could be obtained. 1H-NMR (CDCl3, 400 MHz, δ in ppm): 2.12 (s, 3H) 2.41 (s, 3H) 3.28 (d, J=7.7 Hz, 2H) 3.70 (d, J=17.2 Hz, 1H) 4.10 (d, J=17.2 Hz, 1H) 6.77 (t, J=7.5 Hz, 1H) 7.39 (d, J=7.7 Hz, 1H) 7.59-7.67 (m, 4H) 8.66 (s, 1H)

Using a similar procedure, 2-chloro-N-formyl-N-(3-methyl-4,5-dihydroisoxazol-5-yl)-4-[(5S)-5-(3,4,5-trichlorophenyl)-5-(trifluoromethyl)-4H-isoxazol-3-yl]benzamide (compound A024 in table A) and 2-chloro-N-(3-methyl-4,5-dihydroisoxazol-5-yl)-4-[(5S)-5-(3,4,5-trichlorophenyl)-5-(trifluoromethyl)-4H-isoxazol-3-yl]benzamide (compound A025 in table A) could be obtained.

2-chloro-N-formyl-N-(3-methyl-4,5-dihydroisoxazol-5-yl)-4-[(5S)-5-(3,4,5-trichlorophenyl)-5-(trifluoromethyl)-4H-isoxazol-3-yl]benzamide (compound A024 in table A). 1H-NMR (CDCl3, 400 MHz, δ in ppm): 2.13 (s, 3H) 3.11-3.35 (m, 2H) 3.69 (d, J=17.2 Hz, 1H) 3.98-4.16 (m, 2H) 6.78 (dd, J=9.5, 5.5 Hz, 1H) 7.54 (d, J=8.1 Hz, 1H) 7.64 (s, 2H) 7.71 (dt, J=8.1, 1.8 Hz, 1H) 7.80 (t, J=1.8 Hz, 1H) 8.63 (s, 1H)

2-chloro-N-(3-methyl-4,5-dihydroisoxazol-5-yl)-4-[(5S)-5-(3,4,5-trichlorophenyl)-5-(trifluoromethyl)-4H-isoxazol-3-yl]benzamide (compound A025 in table A). 1H-NMR (CDCl3, 400 MHz, δ in ppm): 2.09 (s, 3H) 2.85-2.98 (m, 1H) 3.40 (ddd, J=17.9, 9.1, 1.3 Hz, 1H) 3.69 (d, J=17.2 Hz, 1H) 4.02-4.13 (m, 1H) 6.42 (ddd, J=8.9, 7.9, 3.3 Hz, 1H) 6.85 (d, J=7.7 Hz, 1H) 7.58-7.67 (m, 3H) 7.69-7.83 (m, 2H)

Using a similar procedure, 4-[(5S)-5-[3-chloro-5-(trifluoromethyl)phenyl]-5-(trifluoromethyl)-4H-isoxazol-3-yl]-N-formyl-2-methyl-N-(3-methyl-4,5-dihydroisoxazol-5-yl)benzamide (compound A039 in table A) could be obtained. 1H-NMR (CDCl3, 400 MHz, δ 2.12 (s, 3H) 2.41 (s, 3H) 3.28 (d, J=7.3 Hz, 2H) 3.73 (d, J=17.2 Hz, 1H) 4.15 (d, J=17.2 Hz, 1H) 6.77 (t, J=7.2 Hz, 1H) 7.40 (d, J=7.7 Hz, 1H) 7.53-7.66 (m, 2H) 7.71 (s, J=4.57 Hz, 1H) 7.76 (s, 1H) 7.83 (s, 1H) 8.66 (s, 1H)

Using a similar procedure, 4-[(5S)-5-[3-bromo-5-(trifluoromethyl)phenyl]-5-(trifluoromethyl)-4H-isoxazol-3-yl]-N-formyl-2-methyl-N-(3-methyl-4,5-dihydroisoxazol-5-yl)benzamide (compound A040 in table A) could be obtained. 1H-NMR (CDCl3, 400 MHz, δ ppm 2.12 (s, 3H) 2.41 (s, 3H) 3.28 (d, J=7.3 Hz, 2H) 3.73 (d, J=17.6 Hz, 1H) 4.15 (d, J=17.2 Hz, 1H) 6.78 (t, J=7.2 Hz, 1H) 7.40 (d, J=8.1 Hz, 1H) 7.53-7.71 (m, 2H) 7.81 (s, 1H) 7.86 (s, 1H) 7.97 (s, 1H) 8.66 (s, 1H)

Using a similar procedure, 2-chloro-4-[(5S)-5-(3,5-dichloro-4-fluoro-phenyl)-5-(trifluoromethyl)-4H-isoxazol-3-yl]-N-formyl-N-(3-methyl-4,5-dihydroisoxazol-5-yl)benzamide (compound A033 in table A) could be obtained. 1H-NMR (CDCl3, 400 MHz, δ ppm 2.13 (s, 3H) 3.16-3.36 (m, 2H) 3.69 (d, J=17.2 Hz, 1H) 4.08 (d, J=17.2 Hz, 1H) 6.78 (dd, J=9.2, 5.1 Hz, 1H) 7.49-7.65 (m, 3H) 7.71 (d, J=7.7 Hz, 1H) 7.80 (s, 1H) 8.63 (s, 1H)

Using a similar procedure, 2-bromo-4-[(5S)-5-(3,5-dichloro-4-fluoro-phenyl)-5-(trifluoromethyl)-4H-isoxazol-3-yl]-N-formyl-N-(3-methyl-4,5-dihydroisoxazol-5-yl)benzamide (compound A034 in table A) and 2-bromo-4-[(5S)-5-(3,5-dichloro-4-fluoro-phenyl)-5-(trifluoromethyl)-4H-isoxazol-3-yl]-N-(3-methyl-4,5-dihydroisoxazol-5-yl)benzamide (compound A036 in table A) could be obtained.

2-bromo-4-[(5S)-5-(3,5-dichloro-4-fluoro-phenyl)-5-(trifluoromethyl)-4H-isoxazol-3-yl]-N-formyl-N-(3-methyl-4,5-dihydroisoxazol-5-yl)benzamide (compound 0A34 in table A). 1H-NMR (CDCl3, 400 MHz, δ in ppm): 2.13 (s, 3H) 3.14-3.39 (m, 2H) 3.69 (d, J=17.2 Hz, 1H) 4.08 (d, J=17.2 Hz, 1H) 6.78 (t, J=7.1 Hz, 1H) 7.50 (d, J=8.1 Hz, 1H) 7.58 (d, J=6.2 Hz, 2H) 7.76 (dt, J=8.1, 1.8 Hz, 1H) 7.88-7.99 (m, 1H) 8.63 (s, 1H).

2-bromo-4-[(5S)-5-(3,5-dichloro-4-fluoro-phenyl)-5-(trifluoromethyl)-4H-isoxazol-3-yl]-N-(3-methyl-4,5-dihydroisoxazol-5-yl)benzamide (compound A036 in table A). 1H-NMR (CDCl3, 400 MHz, δ in ppm): 2.09 (s, 3H) 2.94 (dd, J=17.9, 2.6 Hz, 1H) 3.39 (ddd, J=17.9, 9.1, 0.9 Hz, 1H) 3.68 (d, J=17.2 Hz, 1H) 4.07 (d, J=17.2 Hz, 1H) 6.36-6.45 (m, 1H) 6.65 (d, J=7.7 Hz, 1H) 7.58 (d, J=5.9 Hz, 2H) 7.61-7.65 (m, 1H) 7.65-7.69 (m, 1H) 7.86-7.91 (m, 1H)

Using a similar procedure, 2-bromo-N-formyl-N-(3-methyl-4,5-dihydroisoxazol-5-yl)-4-[(5S)-5-(3,4,5-trichlorophenyl)-5-(trifluoromethyl)-4H-isoxazol-3-yl]benzamide (compound A035 in table A) and 2-bromo-N-(3-methyl-4,5-dihydroisoxazol-5-yl)-4-[(5S)-5-(3,4,5-trichlorophenyl)-5-(trifluoromethyl)-4H-isoxazol-3-yl]benzamide (compound A037 in table A) could be obtained.

2-bromo-N-formyl-N-(3-methyl-4,5-dihydroisoxazol-5-yl)-4-[(5S)-5-(3,4,5-trichlorophenyl)-5-(trifluoromethyl)-4H-isoxazol-3-yl]benzamide (compound A035 in table A). 1H-NMR (CDCl3, 400 MHz, δ in ppm): 2.13 (s, 3H) 3.22-3.35 (m, 2H) 3.69 (d, J=17.2 Hz, 2H) 4.08 (d, J=17.2 Hz, 1H) 6.70-6.90 (m, 1H) 7.50 (d, J=7.7 Hz, 1H) 7.64 (s, 2H) 7.76 (dt, J=8.1, 1.8 Hz, 1H) 7.88-8.08 (m, 1H) 8.63 (s, 1H).

2-bromo-N-(3-methyl-4,5-dihydroisoxazol-5-yl)-4-[(5S)-5-(3,4,5-trichlorophenyl)-5-(trifluoromethyl)-4H-isoxazol-3-yl]benzamide (compound A037 in table A). 1H-NMR (CDCl3, 400 MHz, δ in ppm): 2.08 (s, 3H) 2.94 (dd, J=17.9, 2.9 Hz, 1H) 3.39 (ddd, J=17.9, 9.2, 1.1 Hz, 1H) 3.68 (d, J=17.2 Hz, 1H) 4.07 (d, J=17.2 Hz, 1H) 6.36-6.44 (m, 1H) 6.65 (d, J=7.7 Hz, 1H) 7.61-7.69 (m, 4H) 7.89 (s, 1H)

Example 2f: 4-[(5S)-5-(3,5-dichloro-4-fluoro-phenyl)-5-(trifluoromethyl)-4H-isoxazol-3-yl]-N-(3-ethyl-4,5-dihydroisoxazol-5-yl)-N-formyl-2-methyl-benzamide (Compound A022 in Table A)

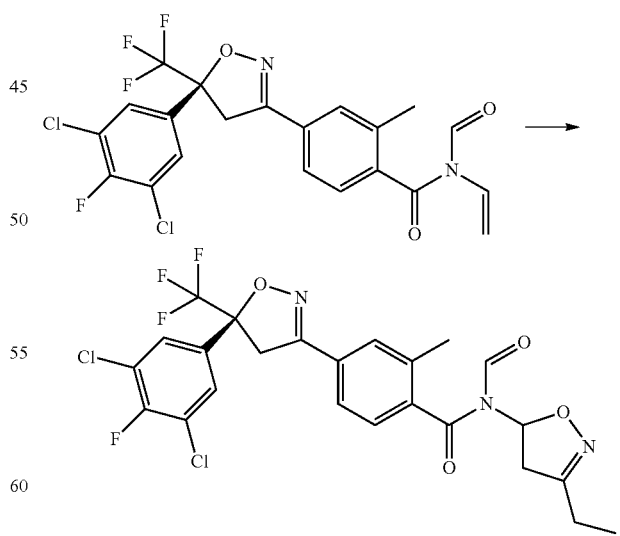

To a solution of N-Chlorosuccinimide (0.48 g) in N,N-Dimethylformamide (11 mL) was added Propionaldehyde oxime (260 mg) and the solution was stirred at ambient temperature for 3 h. Then a solution of 4-[(5S)-5-(3,5- dichloro-4-fluoro-phenyl)-5-(trifluoromethyl)-4H-isoxazol-3-yl]-N-formyl-2-methyl-N-vinyl-benzamide (0.35 g) and Triethylamine (0.5 mL) in N,N-Dimethylformamide (1.8 mL) were added dropwise. The reaction was further stirred at ambient temperature for 15 minutes then was warmed to 60° C. for 3 hours. The reaction mixture was cooled to ambient temperature and stored in the fridge for 18 hours, it was then extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 60:40) as a solvent to give 360 mg of 4-[(5S)-5-(3,5-dichloro-4-fluoro-phenyl)-5-(trifluoromethyl)-4H-isoxazol-3-yl]-N-(3-ethyl-4,5-dihydroisoxazol-5-yl)-N-formyl-2-methyl-benzamide: 1H-NMR (CDCl3, 400 MHz, δ in ppm):

1.26 (t, 3H) 2.41 (s, 3H) 2.50 (q, J=7.3 Hz, 2H) 3.29 (d, J=6.9 Hz, 2H) 3.70 (d, J=17.2 Hz, 1H) 4.07-4.12 (m, 1H) 6.77 (dd, J=8.2, 6.8 Hz, 1H) 7.40 (d, J=7.7 Hz, 1H) 7.53-7.68 (m, 4H) 8.66 (s, 1H)

Example 2g: N-(3-acetyl-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide (Compound A015 in Table A) and N-(3-acetyl-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide (Compound A014 in Table A)

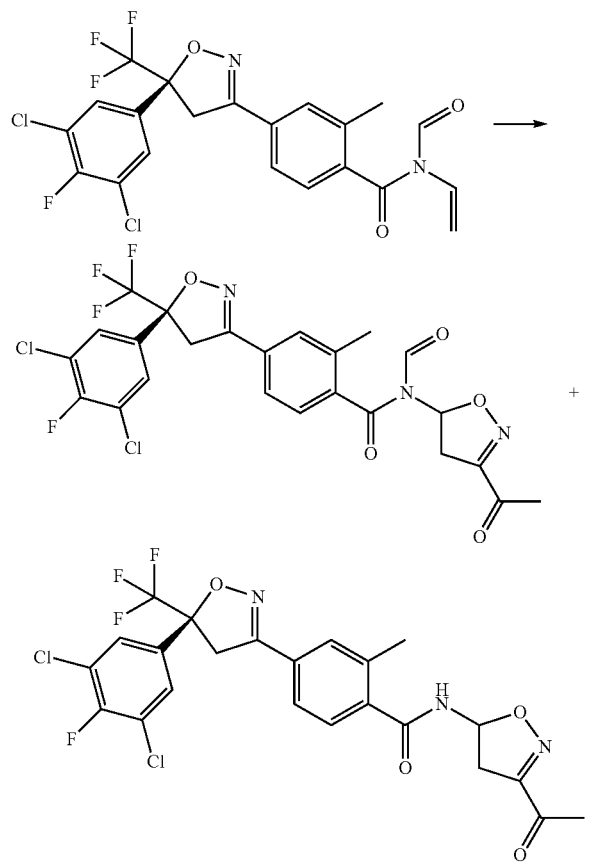

To a solution of 4-[(5S)-5-(3,5-dichloro-4-fluoro-phenyl)-5-(trifluoromethyl)-4H-isoxazol-3-yl]-N-formyl-2-methyl-N-vinyl-benzamide (0.50 g) in Ethylacetate (5 mL) was added a saturated solution of sodium hydrogencarbonate (5 mL). After 5 minutes of stirring at room temperature, sodium hydrogencarbonate (690 mg) and 3-chloro-N-hydroxy-2-oxopropanimidoyl chloride (250 mg, prepared as described in the literature: WO2011085170) was added. The reaction mixture was stirred at ambient temperature for 4 hours then more 3-chloro-N-hydroxy-2-oxopropanimidoyl chloride (250 mg) were added. The reaction was stirred at ambient temperature for another 18 hours then more 3-chloro-N-hydroxy-2-oxopropanimidoyl chloride (250 mg) were added. The reaction mixture was stirred at ambient temperature for 5 hours then was warmed to 60 C and stirred at this temperature for 1.5 hours. The reaction mixture was then cooled to room temperature and was extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 10:90) as a solvent to give two compounds separately that were repurified using a second column chromatography on silica gel using using ethyl acetate/dichloromethane (from 0:100 to 10:90) as a solvent, to give:

72 mg of N-(3-acetyl-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide. 1H-NMR (CDCl3, 400 MHz, δ in ppm): 2.41 (s, 3H) 2.58 (s, 3H) 3.31-3.56 (m, 2H) 3.70 (d, J=17.2 Hz, 1H) 4.10 (d, J=17.2 Hz, 1H) 6.97 (dd, J=11.00, 5.9 Hz, 1H) 7.40 (d, J=8.1 Hz, 1H) 7.53-7.70 (m, 4H) 8.63 (s, 1H)

31 mg of N-(3-acetyl-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide. 1H-NMR (CDCl3, 400 MHz, δ in ppm): 2.50 (s, 3H) 2.54 (s, 3H) 3.10 (dd, J=18.7, 4.4 Hz, 1H) 3.47 (dd, J=18.5, 10.1 Hz, 1H) 3.69 (d, J=17.2 Hz, 1H) 4.03-4.12 (m, 1H) 6.51 (dd, J=8.9, 3.9 Hz, 1H) 6.63 (td, J=9.6, 4.6 Hz, 1H) 7.38-7.48 (m, 1H) 7.49-7.55 (m, 2H) 7.59 (d, J=6.2 Hz, 2H)

Using similar conditions, the following compounds could also be obtained:

N-(3-chloro-4,5-dihydroisoxazol-5-yl)-4-[(5S)-5-[3-chloro-5-(trifluoromethyl)phenyl]-5-(trifluoromethyl)-4H-isoxazol-3-yl]-2-methyl-benzamide (compound A016 in table A) and N-(3-chloro-4,5-dihydroisoxazol-5-yl)-4-[(5S)-5-[3-chloro-5-(trifluoromethyl)phenyl]-5-(trifluoromethyl)-4H-isoxazol-3-yl]-N-formyl-2-methyl-benzamide (compound A012 in table A).

N-(3-chloro-4,5-dihydroisoxazol-5-yl)-4-[(5S)-5-[3-chloro-5-(trifluoromethyl)phenyl]-5-(trifluoromethyl)-4H-isoxazol-3-yl]-2-methyl-benzamide (compound A016 in table A) 1H-NMR (CDCl3, 400 MHz, δ in ppm): 2.49 (s, 3H) 3.09 (dd, J=17.6, 3.7 Hz, 1H) 3.63 (dd, J=17.9, 9.2 Hz, 1H) 3.73 (d, J=17.2 Hz, 1H) 4.15 (d, J=17.2 Hz, 1H) 6.52-6.79 (m, 2H) 7.40-7.49 (m, 1H) 7.51-7.57 (m, 2H) 7.70 (s, 1H) 7.77 (s, 1H) 7.83 (s, 1H)

N-(3-chloro-4,5-dihydroisoxazol-5-yl)-4-[(5S)-5-[3-chloro-5-(trifluoromethyl)phenyl]-5-(trifluoromethyl)-4H-isoxazol-3-yl]-N-formyl-2-methyl-benzamide (compound A012 in table A). 1H-NMR (CDCl3, 400 MHz, δ in ppm): 2.42 (s, 3H) 3.42-3.58 (m, 2H) 3.74 (d, J=17.2 Hz, 1H) 4.15 (d, J=17.2 Hz, 1H) 6.93 (dd, J=10.4, 5.7 Hz, 1H) 7.41 (d, J=8.1 Hz, 1H) 7.59-7.67 (m, 2H) 7.71 (s, 1H) 7.76 (s, 1H) 7.83 (s, 1H) 8.66 (s, 1H)

Using similar conditions, the following compounds could also be obtained:

2-chloro-N-(3-chloro-4,5-dihydroisoxazol-5-yl)-N-formyl-4-[(5S)-5-(3,4,5-trichlorophenyl)-5-(trifluoromethyl)-4H-isoxazol-3-yl]benzamide (compound A017 in table A) and 2-chloro-N-(3-chloro-4,5-dihydroisoxazol-5-yl)-4-[(5S)-5-(3,4,5-trichlorophenyl)-5-(trifluoromethyl)-4H-isoxazol-3-yl]benzamide (compound A018 in table A).

2-chloro-N-(3-chloro-4,5-dihydroisoxazol-5-yl)-N-formyl-4-[(5S)-5-(3,4,5-trichlorophenyl)-5-(trifluoromethyl)-4H-isoxazol-3-yl]benzamide (compound A017 in table A): 1H-NMR (CDCl3, 400 MHz, δ in ppm): 3.39-3.60 (m, 2H) 3.70 (d, J=17.2 Hz, 1H) 4.09 (d, J=17.2 Hz, 1H) 6.93 (dd, J=10.6, 5.5 Hz, 1H) 7.56 (d, J=8.1 Hz, 1H) 7.64 (s, 2H) 7.74 (dt, J=7.7, 2.0 Hz, 1H) 7.78-7.95 (m, 1H) 8.63 (s, 1H).

2-chloro-N-(3-chloro-4,5-dihydroisoxazol-5-yl)-4-[(5S)-5-(3,4,5-trichlorophenyl)-5-(trifluoromethyl)-4H-isoxazol-3-yl]benzamide (compound A018 in table A). 1H-NMR (CDCl3, 400 MHz, δ in ppm): 3.13 (dd, J=18.2, 4.2 Hz, 1H) 3.58-3.66 (m, 1H) 3.66-3.75 (m, 1H) 4.08 (d, J=17.6 Hz, 1H) 6.56 (ddd, J=9.4, 8.3, 4.2 Hz, 1H) 7.07 (d, J=8.1 Hz, 1H) 7.61-7.66 (m, 3H) 7.69-7.86 (m, 2H)

Using similar conditions, the 4-[(5S)-5-[3-bromo-5-(trifluoromethyl)phenyl]-5-(trifluoromethyl)-4H-isoxazol-3-yl]-N-(3-chloro-4,5-dihydroisoxazol-5-yl)-N-formyl-2-methyl-benzamide (compound A21 in table A) could also be obtained. 1H-NMR (CDCl3, 400 MHz, δ in ppm): 2.42 (s, 3H) 3.40-3.58 (m, 2H) 3.74 (d, J=17.6 Hz, 1H) 4.13-4.26 (m, 1H) 6.93 (dd, J=10.3, 5.9 Hz, 1H) 7.41 (d, J=8.1 Hz, 1H) 7.53-7.71 (m, 2H) 7.81 (s, 1H) 7.86 (s, 1H) 7.97 (s, 1H) 8.66 (s, 1H)

Example 2h: N-(3-cyclopropyl-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide (Compound A031 in Table A)

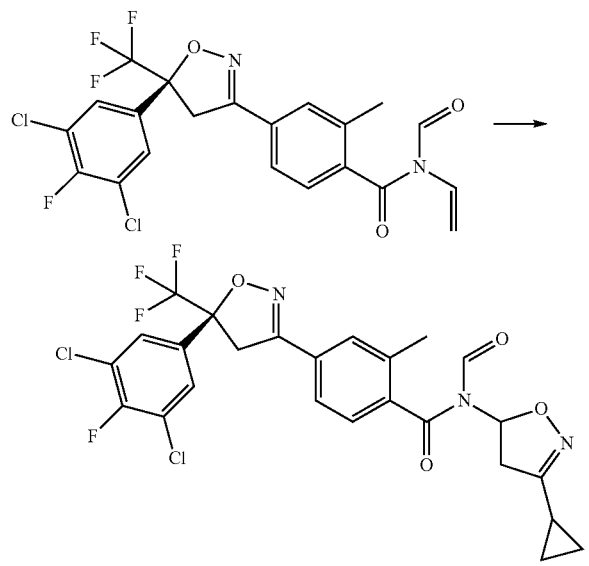

To a solution of N-Chlorosuccinimide (0.55 g) in N,N-Dimethylformamide (12 mL) was added cyclopropylaldehyde oxime (350 mg) and the solution was stirred at ambient temperature for 2 h. Then a solution of 4-[(5S)-5-(3,5-dichloro-4-fluoro-phenyl)-5-(trifluoromethyl)-4H-isoxazol-3-yl]-N-formyl-2-methyl-N-vinyl-benzamide (0.40 g) and Triethylamine (0.58 mL) in N,N-Dimethylformamide (2 mL) were added dropwise. The reaction was further stirred at ambient temperature for 10 minutes then was warmed to 60° C. for 4 hours. The reaction mixture was cooled to ambient temperature and stored in the fridge for 18 hours, it was then extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 50:50) as a solvent to give 223 mg of N-(3-cyclopropyl-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide: 1H-NMR (CDCl3, 400 MHz, δ in ppm): 0.84-1.00 (m, 4H) 1.80-1.84 (m, 1H) 2.40 (s, 3H) 3.10-3.24 (m, 2H) 3.70 (d, J=17.2 Hz, 1H) 4.07-4.11 (m, 1H) 6.76 (dd, J=9.2, 5.9 Hz, 1H) 7.39 (d, J=7.7 Hz, 1H) 7.52-7.68 (m, 4H) 8.65 (s, 1H)

Example 3: N-(3-bromo-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide (Compound A001 in Table A)

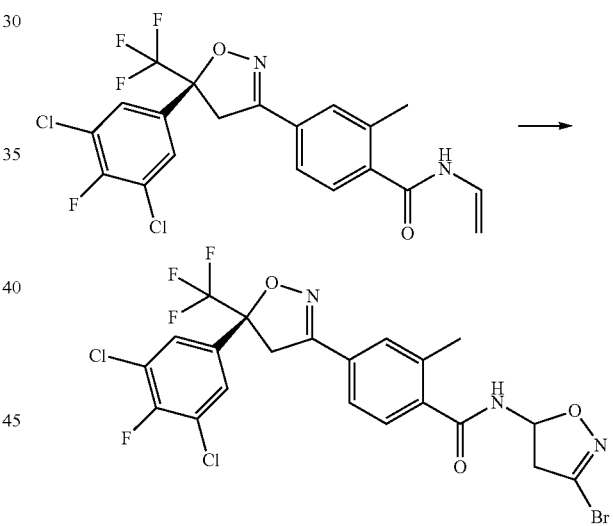

To a solution of 4-[(5S)-5-(3,5-dichloro-4-fluoro-phenyl)-5-(trifluoromethyl)-4H-isoxazol-3-yl]-2-methyl-N-vinyl-benzamide (500 mg) in Ethylacetate (13 mL) was added sodium hydrogencarbonate (410 mg). After 5 minutes at room temperature, 260 mg of Dibromoformaldoxime (prepared as described in the literature: Chemical Communications, 2010, p. 8475-8477). The reaction mixture was stirred at ambient temperature for 18 hours then it was extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 100:0) as a solvent. Thus, 287 mg of N-(3-bromo-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide was obtained.

1H-NMR (CDCl3, 400 MHz, δ in ppm): 2.49 (s, 3H) 3.13 (dd, J=17.97, 3.67 Hz, 1H) 3.61-3.74 (m, 2H) 3.94-4.16 (m, 1H) 6.47-6.67 (m, 2H) 7.39-7.49 (m, 1H) 7.50-7.56 (m, 2H) 7.59 (d, J=5.87 Hz, 2H)

Example 4: N-(3-chloro-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide (Compound A003 in Table A)

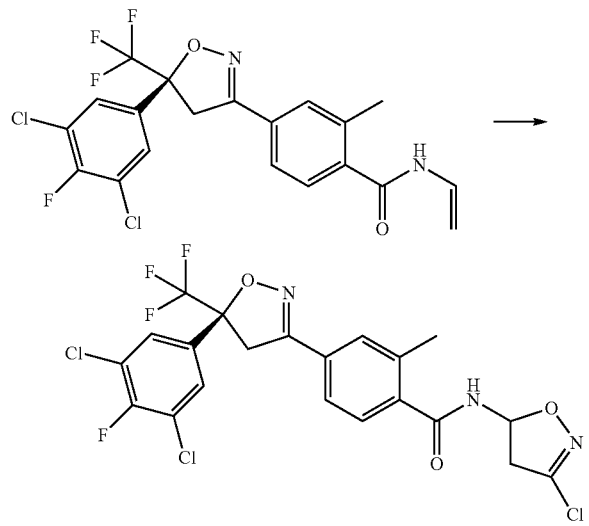

To a solution of 4-[(5S)-5-(3,5-dichloro-4-fluoro-phenyl)-5-(trifluoromethyl)-4H-isoxazol-3-yl]-2-methyl-N-vinyl-benzamide (500 mg) in toluene (22 mL) was added potassium carbonate (300 mg) and Triethylamine (0.15 mL). After 20 minutes at room temperature, a solution of dichloroformaldoxime (1 mL, 1.4 mol/L in dimethoxyethane, prepared as described in the literature: Chemical Communications, 2010, p. 8475-8477) was added by portions over 50 minutes. The reaction mixture was stirred at ambient temperature for 18 hours. To this suspension was then added a saturated solution of sodium hydrogenocarbonate (20 ml) and Ethylacetate (20 mL). The reaction mixture was stirred at ambient temperature for 1 hour then a solution of dichloroformaldoxime (1 mL, 1.4 mol/L in dimethoxyethane) was added by portions over 3 h40 minutes, along with ca 240 mg of sodium hydrogenocarbonate. The reaction mixture was stirred at ambient temperature for 18 hours then it was extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 60:0) as a solvent. Thus, 196 mg of N-(3-chloro-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide was obtained.

1H-NMR (CDCl3, 400 MHz, δ in ppm): 2.49 (s, 3H) 3.06-3.13 (m, 1H) 3.63 (dd, J=18.2, 9.0 Hz, 1H) 3.70 (d, J=17.2 Hz, 1H) 4.09 (d, J=17.2 Hz, 1H) 6.50-6.66 (m, 2H) 7.44 (d, J=7.32 Hz, 1H) 7.52 (d, J=5.36 Hz, 2H) 7.59 (d, J=6.24 Hz, 2H)

Example 5: 4-[(5S)-5-(3,5-dichloro-4-fluoro-phenyl)-5-(trifluoromethyl)-4H-isoxazol-3-yl]-2-methyl-N-(3-methyl-4,5-dihydroisoxazol-5-yl)benzamide (Compound A009 in Table A)

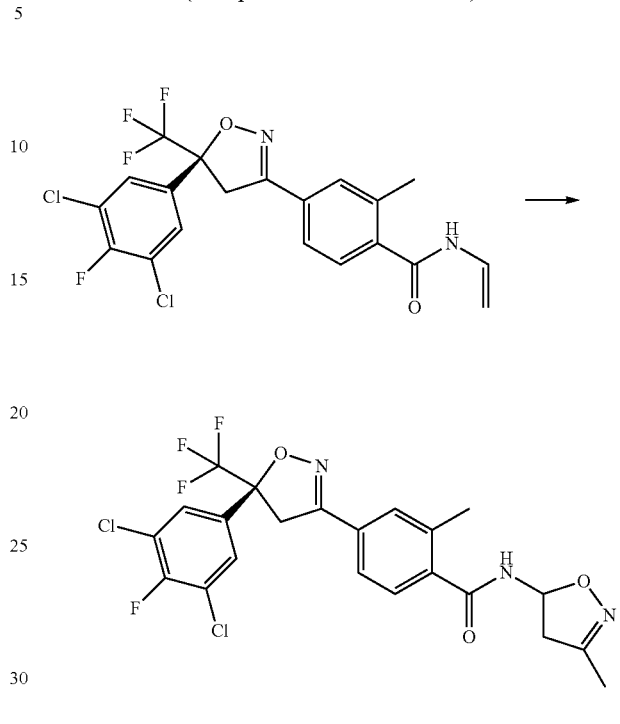

To a solution of 4-[(5S)-5-(3,5-dichloro-4-fluoro-phenyl)-5-(trifluoromethyl)-4H-isoxazol-3-yl]-2-methyl-N-vinyl-benzamide (100 mg) in Ethylacetate (2 mL) and water (0.11 mL) was added potassium carbonate (91 mg). After 15 minutes at room temperature, a solution of the N-hydroxyethanimidoyl chloride (61 mg, prepared as described in the literature: WO2013052394) in Ethylacetate (0.3 mL) was added by portions over 15 minutes. The reaction mixture was stirred at ambient temperature for 1 hour. To this suspension was then added a saturated solution of sodium hydrogenocarbonate (5 ml) and followed by some more of the N-hydroxyethanimidoyl chloride (61 mg). The reaction mixture was stirred at ambient temperature for 5 hour then some more of the N-hydroxyethanimidoyl chloride (61 mg) was added. The reaction mixture was stirred at ambient temperature for 21 hours. An additional amount of the N-hydroxyethanimidoyl chloride (61 mg) was added and the reaction mixture was stirred at ambient temperature for 2 hour then some more of the N-hydroxyethanimidoyl chloride (61 mg) was added. The reaction mixture was stirred at ambient temperature for 20 hours then it was extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 70:0) as a solvent. It was then further repurified by preparative HPLC to give 6.8 mg of 4-[(5S)-5-(3,5-dichloro-4-fluoro-phenyl)-5-(trifluoromethyl)-4H-isoxazol-3-yl]-2-methyl-N-(3-methyl-4,5-dihydroisoxazol-5-yl)benzamide. 1H-NMR (CDCl3, 400 MHz, δ in ppm): 2.08 (s, 3H) 2.49 (s, 3H) 2.84-2.92 (m, 1H) 3.39 (dd, J=18.2, 7.9 Hz, 1H) 3.69 (d, J=17.2 Hz, 1H) 4.09 (d, J=17.2 Hz, 1H) 6.38-6.46 (m, 2H) 7.42-7.44 (m, 1H) 7.49-7.55 (m, 2H) 7.59 (d, J=5.9 Hz, 2H)

Example 6a: 4-[(5S)-5-(3,5-dichloro-4-fluoro-phenyl)-5-(trifluoromethyl)-4H-isoxazol-3-yl]-2-methyl-N-vinyl-benzamide

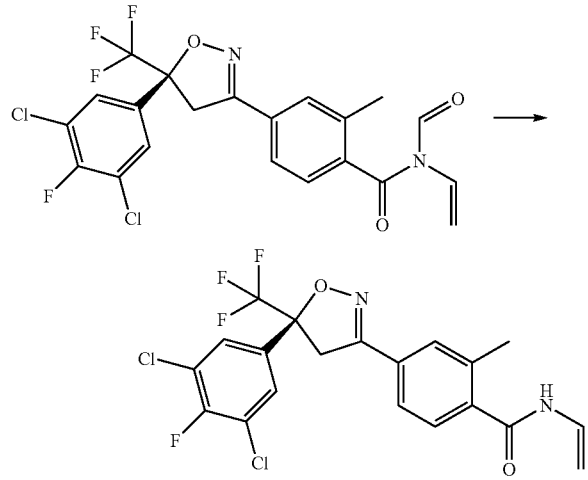 [SMILES: C=CN(C=O)C(=O)c1ccc(C2=NO[C@@](c3cc(Cl)c(F)c(Cl)c3)(C(F)(F)F)C2)cc1C ; C=CNC(=O)c1ccc(C2=NO[C@@](c3cc(Cl)c(F)c(Cl)c3)(C(F)(F)F)C2)cc1C]

To a solution of 4-[(5S)-5-(3,5-dichloro-4-fluoro-phenyl)-5-(trifluoromethyl)-4H-isoxazol-3-yl]-N-formyl-2-methyl-N-vinyl-benzamide (1.75 g) in Tetrahydrofuran (17.5 mL) was added sodium hydroxide aq. 2M (2.15 mL). After 3 hours of stirring at room temperature, the reaction was extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 60:40) as a solvent. It was then repurified by column chromatography on silica gel using using ethyl acetate/dichloromethane (from 0:100 to 10:90) as a solvent to give 830 mg of 4-[(5S)-5-(3,5-dichloro-4-fluoro-phenyl)-5-(trifluoromethyl)-4H-isoxazol-3-yl]-2-methyl-N-vinyl-benzamide.

1H-NMR (CDCl3, 400 MHz, δ in ppm): 2.51 (s, 3H) 3.70 (d, J=17.2 Hz, 1H) 4.10 (d, J=17.2 Hz, 1H) 4.58 (d, J=8.8 Hz, 1H) 4.75 (d, J=15.8, 1 H) 7.13-7.20 (m, 1H) 7.35-7.38 (m, 1H) 7.44-7.51 (m, 1H) 7.51-7.65 (m, 4H)

Example 6b: 4-[(5S)-5-(3,5-dichloro-4-fluoro-phenyl)-5-(trifluoromethyl)-4H-isoxazol-3-yl]-2-methyl-N-[3-(trifluoromethyl)-4,5-dihydroisoxazol-5-yl]benzamide (Compound A005 in Table A)

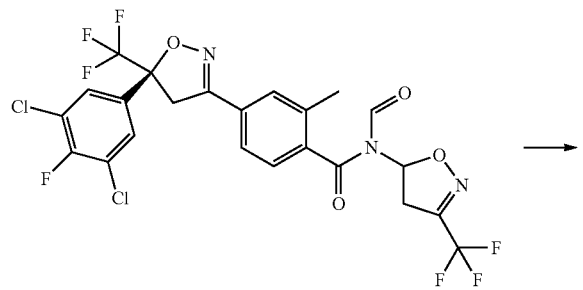

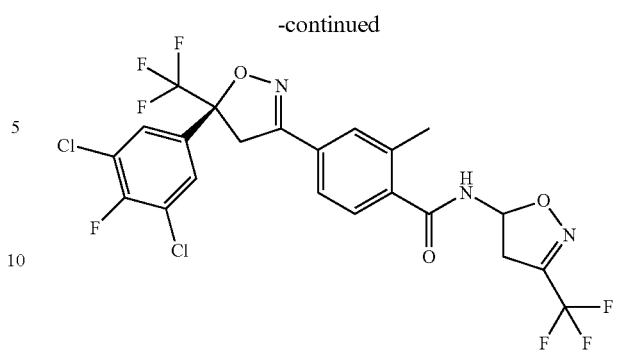

To a solution of 4-[(5S)-5-(3,5-dichloro-4-fluoro-phenyl)-5-(trifluoromethyl)-4H-isoxazol-3-yl]-N-formyl-2-methyl-N-[3-(trifluoromethyl)-4,5-dihydroisoxazol-5-yl]benzamide (60 mg) in Tetrahydrofuran (0.6 mL) was added sodium hydroxide aq. 2M (0.06 mL). After 2.5 hours of stirring at room temperature, the reaction was extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 30:70) as a solvent. Thus, 52 mg of 4-[(5S)-5-(3,5-dichloro-4-fluoro-phenyl)-5-(trifluoromethyl)-4H-isoxazol-3-yl]-2-methyl-N-[3-(trifluoromethyl)-4,5-dihydroisoxazol-5-yl]benzamide was obtained.

1H-NMR (CDCl3, 400 MHz, δ in ppm): 2.49 (s, 3H) 3.14 (dd, J=18.2, 4.2 Hz, 1H) 3.58 (dd, J=18.3, 8.4 Hz, 1H) 3.70 (d, J=17.2 Hz, 1H) 4.03-4.13 (m, 1H) 6.48-6.72 (m, 2H) 7.39-7.49 (m, 1H) 7.53 (m, 2H) 7.59 (d, J=5.9 Hz, 2H)

Example 6c: 4-[(5S)-5-(3,5-dichloro-4-fluoro-phenyl)-5-(trifluoromethyl)-4H-isoxazol-3-yl]-N-(3-ethyl-4,5-dihydroisoxazol-5-yl)-2-methyl-benzamide (Compound A026 in Table A)

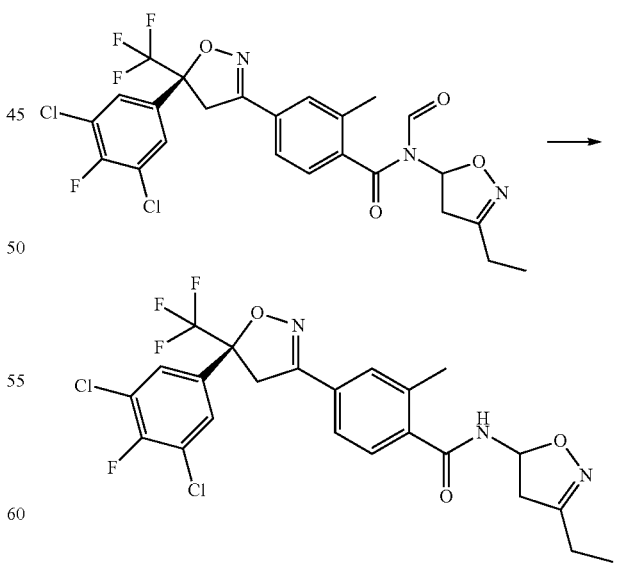

Using similar conditions than in example 6b, 4-[(5S)-5-(3,5-dichloro-4-fluoro-phenyl)-5-(trifluoromethyl)-4H-isoxazol-3-yl]-N-(3-ethyl-4,5-dihydroisoxazol-5-yl)-2-methyl-benzamide could be obtained from 4-[(5S)-5-(3,5- dichloro-4-fluoro-phenyl)-5-(trifluoromethyl)-4H-isoxazol-3-yl]-N-(3-ethyl-4,5-dihydroisoxazol-5-yl)-N-formyl-2-methyl-benzamide.

4-[(5S)-5-(3,5-dichloro-4-fluoro-phenyl)-5-(trifluoromethyl)-4H-isoxazol-3-yl]-N-(3-ethyl-4,5-dihydroisoxazol-5-yl)-2-methyl-benzamide: 1H-NMR (CDCl3, 400 MHz, δ in ppm): 1.13-1.27 (m, 3H) 2.40-2.45 (m, 2H) 2.45-2.52 (m, 3H) 2.88 (dd, J=18.2, 3.1 Hz, 1H) 3.39 (dd, J=17.9, 8.4 Hz, 1H) 3.69 (d, J=17.2 Hz, 1H) 4.09 (d, J=17.2 Hz, 1H) 6.32-6.49 (m, 2H) 7.39-7.47 (m, 1H) 7.49-7.54 (m, 2H) 7.59 (d, J=5.87 Hz, 2H)

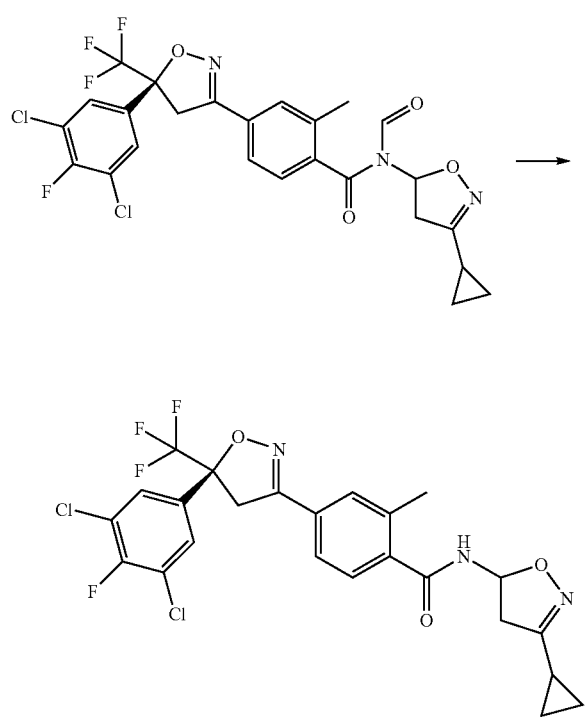

Using similar conditions than in example 6b, N-(3-cyclopropyl-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide could be obtained from N-(3-cyclopropyl-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide.

N-(3-cyclopropyl-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide: 1H-NMR (CDCl3, 400 MHz, δ in ppm): 0.70-0.91 (m, 2H) 0.92-1.12 (m, 2H) 1.82 (td, J=8.8, 4.4 Hz, 1H) 2.49 (s, 3H) 2.72 (dd, J=17.6, 2.9 Hz, 1H) 3.26 (dd, J=17.6, 8.4 Hz, 1H) 3.69 (d, J=17.2 Hz, 1H) 4.02-4.13 (m, 1H) 6.29-6.54 (m, 2H) 7.39-7.47 (m, 1H) 7.48-7.55 (m, 2H) 7.59 (d, J=5.9 Hz, 2H).

Using similar conditions than in example 6b, 4-[(5S)-5-[3-bromo-5-(trifluoromethyl)phenyl]-5-(trifluoromethyl)-4H-isoxazol-3-yl]-N-(3-chloro-4,5-dihydroisoxazol-5-yl)-2-methyl-benzamide (compound A021 in table A): could be obtained. 1H-NMR (CDCl3, 400 MHz, δ in ppm): 2.49 (s, 3H) 3.09 (dd, J=18.2, 4.2 Hz, 1H) 3.63 (dd, J=17.9, 9.2 Hz, 1H) 3.73 (d, J=17.2 Hz, 1H) 4.14 (d, J=17.2 Hz, 1H) 6.52-6.71 (m, 2H) 7.40-7.49 (m, 1H) 7.53-7.54 (m, J=6.2 Hz, 2H) 7.81 (s, 1H) 7.85 (s, 1H) 7.98 (s, 1H)

Example 6d: ethyl 5-[[4-[(5S)-5-(3,5-dichloro-4-fluoro-phenyl)-5-(trifluoromethyl)-4H-isoxazol-3-yl]-2-methyl-benzoyl]amino]-4,5-dihydroisoxazole-3-carboxylate (Compound A007 in Table A)

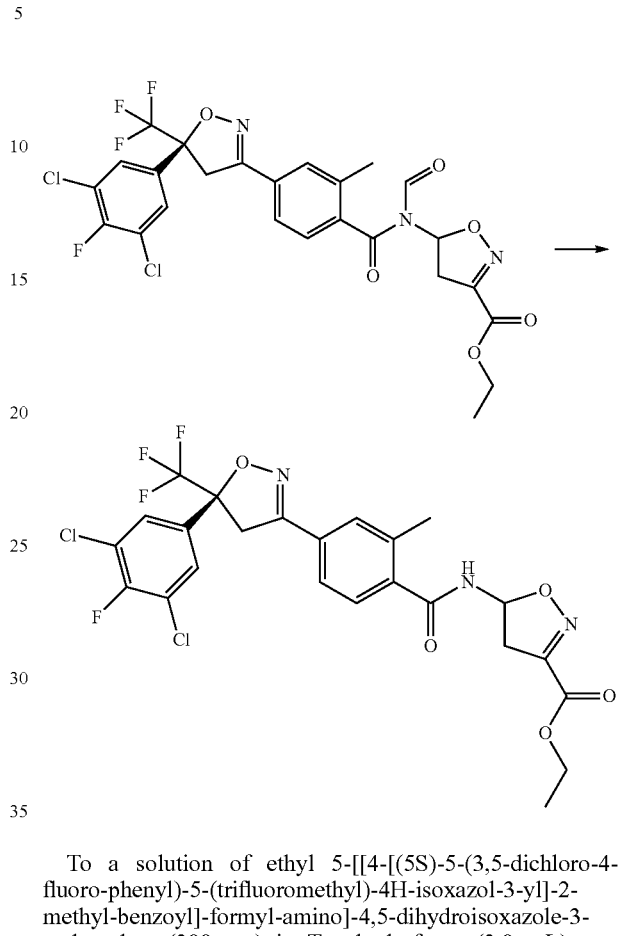

To a solution of ethyl 5-[[4-[(5S)-5-(3,5-dichloro-4-fluoro-phenyl)-5-(trifluoromethyl)-4H-isoxazol-3-yl]-2-methyl-benzoyl]-formyl-amino]-4,5-dihydroisoxazole-3-carboxylate (200 mg) in Tetrahydrofuran (2.0 mL) was added sodium hydroxide aq. 2M (0.20 mL) and the reaction was stirred at 0 C for 1.5 hours. The reaction was then extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 50:50) as a solvent. Thus, 73 mg of ethyl 5-[[4-[(5S)-5-(3,5-dichloro-4-fluoro-phenyl)-5-(trifluoromethyl)-4H-isoxazol-3-yl]-2-methyl-benzoyl]amino]-4,5-dihydroisoxazole-3-carboxylate was obtained.

1H-NMR (CDCl3, 400 MHz, δ in ppm): 1.38 (t, J=7.1 Hz, 3H) 2.49 (s, 3H) 3.16 (dd, J=18.7, 3.7 Hz, 1H) 3.58 (dd, J=18.7, 9.5 Hz, 1H) 3.69 (d, J=17.2 Hz, 1H) 4.09 (d, J=17.2 Hz, 1H) 4.37 (q, J=6.7 Hz, 2H) 6.54-6.73 (m, 2H) 7.39-7.48 (m, 1H) 7.49-7.55 (m, 2H) 7.59 (d, J=5.87 Hz, 2H)

Using a similar procedure, N-(3-chloro-4,5-dihydroisoxazol-5-yl)-2-methyl-4-[(5S)-5-(3,4,5-trichlorophenyl)-5-(trifluoromethyl)-4H-isoxazol-3-yl]benzamide (compound A013 in table A) could be obtained. 1H-NMR (CDCl3, 400 MHz, δ in ppm): 2.49 (s, 3H) 2.98-3.18 (m, 1H) 3.62 (dd, J=17.9, 9.5 Hz, 1H) 3.70 (d, J=17.2 Hz, 1H) 4.09 (d, J=17.6 Hz, 1H) 6.51-6.78 (m, 2H) 7.40-7.48 (m, 1H) 7.52 (m, 2H) 7.65 (s, 2H)

Using a similar procedure, 2-methyl-N-(3-methyl-4,5-dihydroisoxazol-5-yl)-4-[(5S)-5-(3,4,5-trichlorophenyl)-5-(trifluoromethyl)-4H-isoxazol-3-yl]benzamide (compound A027 in table A) could be obtained: 1H-NMR (CDCl3, 400 MHz, δ in ppm 2.08 (s, 3H) 2.49 (s, 3H) 2.68-2.93 (m, 1H) 3.39 (dd, J=17.9, 7.7 Hz, 1H) 3.69 (d, J=17.2 Hz, 1H) 4.05-4.12 (m, 1H) 6.29-6.54 (m, 2H) 7.39-7.47 (m, 1H) 7.49-7.55 (m, 2H) 7.65 (s, 2H)

Using a similar procedure, 4-[(5S)-5-[3-chloro-5-(trifluoromethyl)phenyl]-5-(trifluoromethyl)-4H-isoxazol-3-yl]-2-methyl-N-(3-methyl-4,5-dihydroisoxazol-5-yl)benzamide (compound A028 in table A) could be obtained: 1H-NMR (CDCl3, 400 MHz, δ in ppm 2.08 (s, 3H) 2.50 (s, 3H) 2.69-2.95 (m, 1H) 3.39 (dd, J=17.9, 7.7 Hz, 1H) 3.73 (d, J=17.2 Hz, 1H) 4.02-4.23 (m, 1H) 6.33-6.50 (m, 2H) 7.44 (d, J=8.4 Hz, 1H) 7.50-7.57 (m, 2H) 7.70 (s, 1H) 7.77 (s, 1H) 7.83 (s, 1H).

Using a similar procedure, 4-[(5S)-5-[3-bromo-5-(trifluoromethyl)phenyl]-5-(trifluoromethyl)-4H-isoxazol-3-yl]-2-methyl-N-(3-methyl-4,5-dihydroisoxazol-5-yl)benzamide (compound A029 in table A) could be obtained: 1H-NMR (CDCl3, 400 MHz, δ in ppm): 2.08 (s, 3H) 2.50 (s, 3H) 2.87 (dd, J=17.9, 2.6 Hz, 1H) 3.39 (dd, J=17.9, 7.7 Hz, 1H) 3.72 (d, J=17.2 Hz, 1H) 4.12-4.18 (m, 1H) 6.29-6.53 (m, 2H) 7.42-7.44 (m, 1H) 7.45 (s, 1H) 7.49-7.59 (m, 2H) 7.81 (s, 1H) 7.85 (s, 1H) 7.98 (s, 1H).

Using a similar procedure, 2-chloro-4-[(5S)-5-(3,5-dichloro-4-fluoro-phenyl)-5-(trifluoromethyl)-4H-isoxazol-3-yl]-N-(3-methyl-4,5-dihydroisoxazol-5-yl)benzamide (compound A038 in table A) could be obtained: 1H-NMR (CDCl3, 400 MHz, δ in ppm): 2.09 (s, 3H) 2.93 (dd, J=18.3, 2.9 Hz, 1H) 3.39 (ddd, J=17.9, 8.8, 1.1 Hz, 1H) 3.62-3.73 (m, 1H) 4.07 (d, J=17.2 Hz, 1H) 6.36-6.46 (m, 1H) 6.87 (d, J=7.7 Hz, 1H) 7.51-7.67 (m, 3H) 7.67-7.82 (m, 2H)

Example 8: Preparation of 4-[(5S)-5-(3,5-dichloro-4-methylsulfanyl-phenyl)-5-(trifluoromethyl)-4H-isoxazol-3-yl]-2-methyl-N-(3-methylsulfanyl-4,5-dihydroisoxazol-5-yl)benzamide (Compound A020 in Table A)

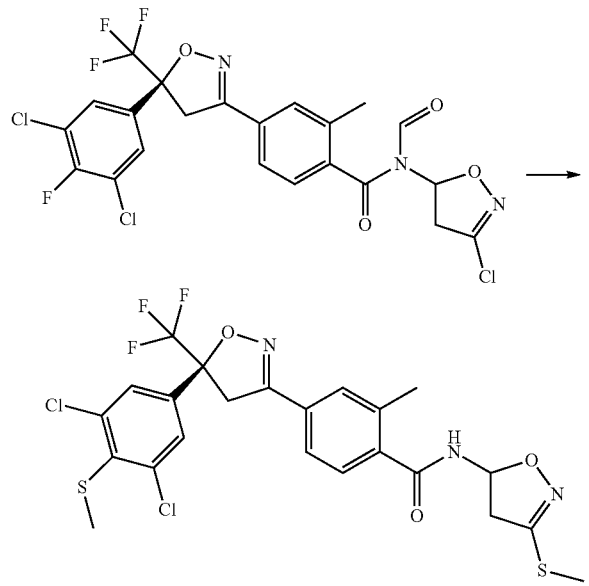

To as solution of N-(3-chloro-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide (100 mg) in N,N-Dimethylformamide (2.0 mL) at room temperature was added Sodium thiomethoxide (22 mg) and the reaction mixture was stirred for 5 hours. The reaction was then extracted between ethyl acetate and water. The combined organic layers were dried over anhydrous magnesium sulfate, filtered and evaporated to give a crude residue, which was then purified by column chromatography on silica gel using using ethyl acetate/Cyclohexane (from 0:100 to 50:50) as a solvent. Thus, 32 mg of 4-[(5S)-5-(3,5-dichloro-4-methylsulfanyl-phenyl)-5-(trifluoromethyl)-4H-isoxazol-3-yl]-2-methyl-N-(3-methylsulfanyl-4,5-dihydroisoxazol-5-yl)benzamide was obtained.

1H-NMR (CDCl3, 400 MHz, δ in ppm): 2.47 (s, 3H) 2.49 (s, 3H) 2.53 (s, 3H) 2.96 (dd, J=17.4, 2.7 Hz, 1H) 3.51 (dd, J=17.2, 8.4 Hz, 1H) 3.70 (d, J=17.2 Hz, 1H) 4.08 (d, J=17.2 Hz, 1H) 6.42-6.62 (m, 2H) 7.43 (d, J=8.44 Hz, 1H) 7.49-7.54 (m, 2H) 7.63 (s, 2H)

Example 8a: Preparation of N-(3-cyano-4,5-dihydroisoxazol-5-yl)-2-methyl-4-[(5S)-5-(3,4,5-trichlorophenyl)-5-(trifluoromethyl)-4H-isoxazol-3-yl]benzamide (Compound A145 in Table A)

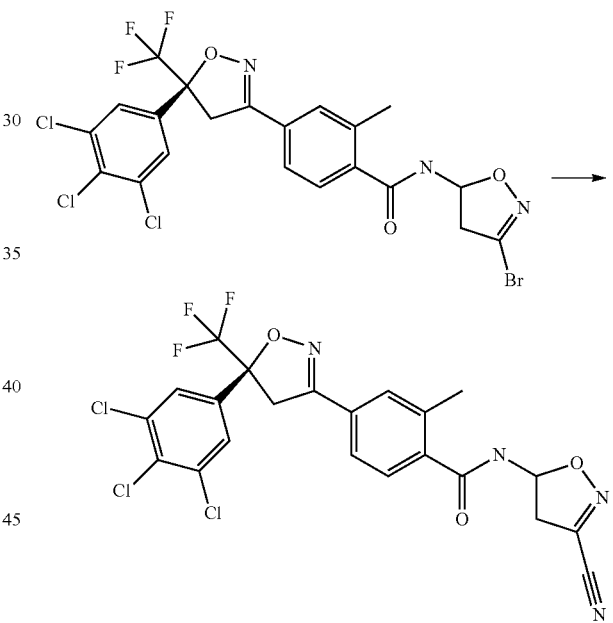

To a solution of N-(3-bromo-4,5-dihydroisoxazol-5-yl)-2-methyl-4-[(5S)-5-(3,4,5-trichlorophenyl)-5-(trifluoromethyl)-4H-isoxazol-3-yl]benzamide (0.50 g) in Pyridine (8.3 mL) was added coppercyanide (0.15 g). The resulting yellow suspension was heated twice under microwave conditions for 20 min at 120° C. The reaction was then extracted between ethyl acetate and water. The combined organic layers were dried over anhydrous magnesium sulfate, filtered and evaporated to give a crude residue, which was then purified by chromatography on silica gel, using ethyl acetate/cyclohexane (gradient from 0:10 to 10:0) as a solvent. The fractions containing the desired compound were further purified by preparative HPLC. Thus, 101 mg of N-(3-cyano-4,5-dihydroisoxazol-5-yl)-2-methyl-4-[(5S)-5-(3,4,5-trichlorophenyl)-5-(trifluoromethyl)-4H-isoxazol-3-yl]benzamide were obtained. 1H NMR (400 MHz, DMSO-d6) δ ppm 2.39 (s, 3H) 3.19 (dd, J=17.6, 3.7 Hz, 1H) 3.65

(dd, J=17.9, 9.9 Hz, 1H) 4.20-4.50 (m, 2H) 6.54 (td, J=9.4, 3.7 Hz, 1H) 7.50 (d, J=8.4 Hz, 1H) 7.58-7.74 (m, 2H) 7.84 (s, 2H) 9.58 (d, J=9.2 Hz, 1H)

Example 9: Preparation of 4-[(5S)-5-(3,5-dichloro-4-fluoro-phenyl)-5-(trifluoromethyl)-4H-isoxazol-3-yl]-N-(3-methoxy-4,5-dihydroisoxazol-5-yl)-2-methyl-benzamide (Compound A030 in Table A)

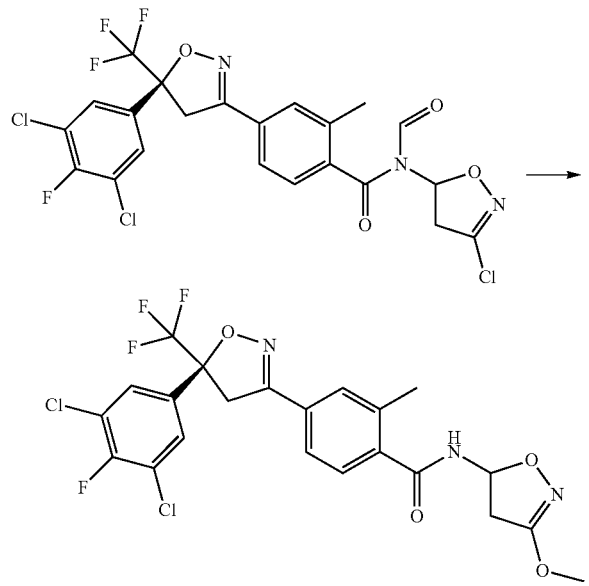

To as solution of N-(3-chloro-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide (100 mg) dissolved in Methanol (2.0 mL) was added sodium methylate approx. 5.4M in Methanol (0.049 mL) and the solution was stirred for 22 hours. The reaction was then extracted between ethyl acetate and water. The combined organic layers were dried over anhydrous magnesium sulfate, filtered and evaporated to give a crude residue, which was then purified by preparative HPLC. Thus, 39 mg of 4-[(5S)-5-(3,5-dichloro-4-fluoro-phenyl)-5-(trifluoromethyl)-4H-isoxazol-3-yl]-N-(3-methoxy-4,5-dihydroisoxazol-5-yl)-2-methyl-benzamide was obtained. 1H-NMR (CDCl3, 400 MHz, δ in ppm): 2.50 (s, 3H) 2.86 (dd, J=17.2, 3.7 Hz, 1H) 3.47 (dd, J=17.2, 8.8 Hz, 1H) 3.69 (d, J=17.2 Hz, 1H) 3.90 (s, 3H) 4.09 (d, J=17.2 Hz, 1H) 6.43 (td, J=8.4, 3.7 Hz, 1H) 6.54 (d, J=8.4 Hz, 1H) 7.44-7.56 (m, 3H) 7.59 (d, J=6.2 Hz, 2H)

Example 10: tert-butyl N-[4-[(5S)-5-(3,5-dichloro-4-fluoro-phenyl)-5-(trifluoromethyl)-4H-isoxazol-3-yl]-2-methyl-benzoyl]-N-vinyl-carbamate

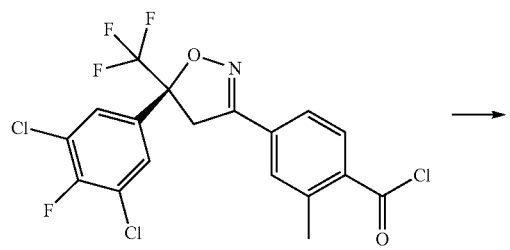

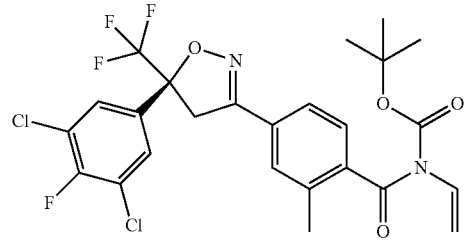

To a solution of 13.72 g tert-butyl N-vinylcarbamate, 23.2 g triethylamine and 1.14 g N,N-dimethylpyridin-4-amine in 200 ml of 1,2-dichloroethane was added a solution of 41.5 g 4-[(5S)-5-(3,5-dichloro-4-fluoro-phenyl)-5-(trifluoromethyl)-4H-isoxazol-3-yl]-2-methyl-benzoyl chloride (obtained as described in Example 1, step 1) in 165 ml of 1,2-dichloroethane at 40-50° C. The mixture was heated on reflux for 18 hours, then allowed to cool to ambient temperature, 75 ml of water and 75 ml of aqueous saturated sodium bicarbonate solution were added, the organic layer was isolated and the aqueous layer was extracted with ethyl acetate. The combined organic layers were dried over anhydrous sodium sulfate, filtered and the solvent evaporated. The residue was purified by chromatography on silica gel, using ethyl acetate/cyclohexane (gradient from 1:19 to 1:5) as a solvent. Thus, 38.09 g of tert-butyl N-[4-[(5S)-5-(3,5-dichloro-4-fluoro-phenyl)-5-(trifluoromethyl)-4H-isoxazol-3-yl]-2-methyl-benzoyl]-N-vinyl-carbamate was obtained as a gum. 1H-NMR (CDCl3, 400 MHz, δ in ppm): 7.59 (d, 2H), 7.48 (s, 1H), 7.36 (d, 1H), 6.82 (dd, 1H), 5.29 (d, 1H), 4.95 (d, 1H), 4.08 (d, 1H), 3.68 (d, 1H), 2.46 (s, 3H), 1.16 (s, 9H).

Example 11: tert-butyl N-(3-chloro-4,5-dihydroisoxazol-5-yl)-N-[4-[(5S)-5-(3,5-dichloro-4-fluoro-phenyl)-5-(trifluoromethyl)-4H-isoxazol-3-yl]-2-methyl-benzoyl]carbamate (Compound A67 in Table A)

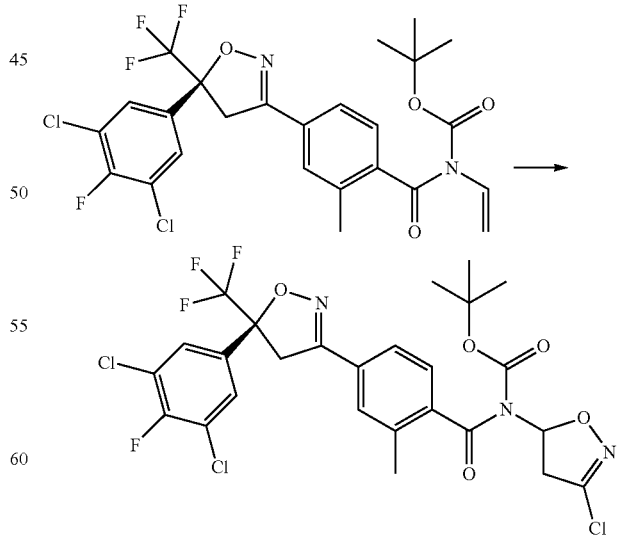

To a mixture of 26.0 g tert-butyl N-[4-[(5S)-5-(3,5-dichloro-4-fluoro-phenyl)-5-(trifluoromethyl)-4H-isoxazol-3-yl]-2-methyl-benzoyl]-N-vinyl-carbamate (Example 10), 19.7 g sodium bicarbonate, 260 ml aqueous saturated sodium bicarbonate and 260 ml ethyl acetate was added 72 ml of a solution of dichloroformaldoxime in dimethoxyethane (0.97 N, prepared as described in the literature: Chemical Communications, 2010, p. 8475-8477) over 15 minutes at ambient temperature. The resulting yellow suspension was stirred at ambient temperature for 18 hours. An additional portion of 70 ml of dichloroformaldoxime in dimethoxyethane (0.97 N) was added and stirring was continued for 3 days. Then the mixture was extracted with water and ethyl acetate, the organic layer was washed with brine, dried over anhydrous sodium sulfate and the solvent evaporated. The residue was purified by chromatography on silica gel, using ethyl acetate/cyclohexane (gradient from 19:1 to 1:5) as a solvent. Thus, 24.04 g of tert-butyl N-(3-chloro-4,5-dihydroisoxazol-5-yl)-N-[4-[(5S)-5-(3,5-dichloro-4-fluoro-phenyl)-5-(trifluoromethyl)-4H-isoxazol-3-yl]-2-methyl-benzoyl]carbamate was obtained as a white amorphous solid. $^{1}$H-NMR (CDCl3, 400 MHz, δ in ppm): 7.58 (d, 2H), 7.53 (s, 1H), 7.48 (d, 1H), 7.33 (d, 1H), 6.89 (t, 1H), 4.07 (d, 1H), 3.66 (d, 1H), 3.47 (d, 2H), 2.42 (s, 3H), 1.16 (s, 9H).

Example 12: N-(3-chloro-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide (Compound A003 in Table A)

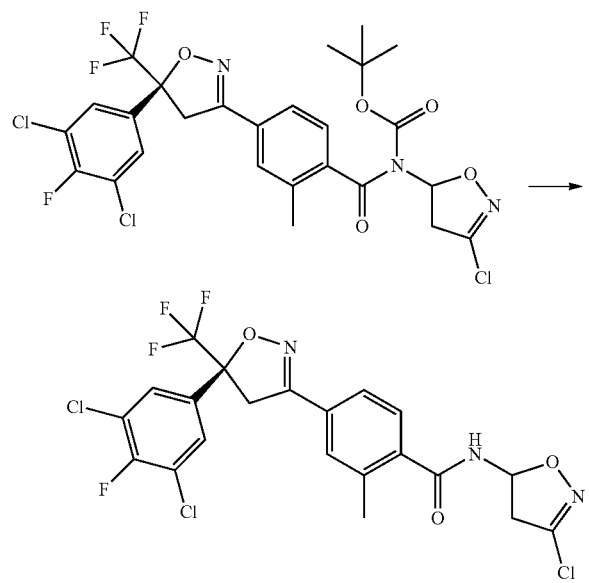

A solution of 10 g tert-butyl N-(3-chloro-4,5-dihydroisoxazol-5-yl)-N-[4-[(5S)-5-(3,5-dichloro-4-fluoro-phenyl)-5-(trifluoromethyl)-4H-isoxazol-3-yl]-2-methyl-benzoyl]carbamate (Example 11) in 100 ml acetic acid was heated in an oil bath at 100° C. After 1 hour, the mixture was concentrated. The residue was dissolved in ethyl acetate. The solution was successively washed with water, aqueous sodium bicarbonate and brine, dried over anhydrous sodium sulfate, and the solvent evaporated. The residue was purified by flash chromatography, using ethyl acetate/cyclohexane as a solvent. Thus, 6.95 g N-(3-chloro-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide was obtained as a colorless resin which crystallized on standing. Analytical data of the sample so obtained were found identical to those listed for Example 4. Recrystallization from ether yielded 5.4 g of the product as colorless crystals which decomposed on melting at 190-192° C.

Preparation of the single isomers N-[(5R)-3-bromo-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide (Example A146 in Table A) and N-[(5S)-3-bromo-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide (Example A147 in Table A

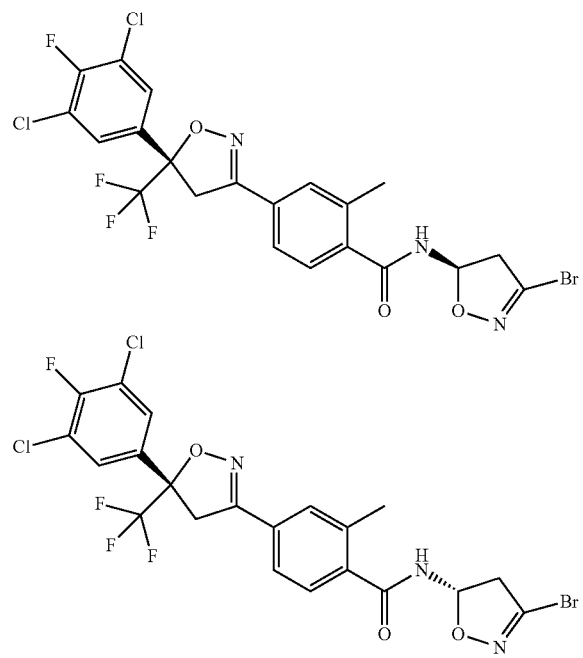

The mixture of isomers, N-(3-bromo-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide was submitted to chiral resolution by preparative HPLC chromatography using the conditions outlined hereafter.
Analytical HPLC Method:
Analytical HPLC method:
HPLC: Waters UPLC-HClass, DAD Detector Waters UPLC
Column: Daicel CHIRALPAK® IA, 3 μm, 0.46 cm×10 cm
Mobile phase: Hept/EtOAc 80/20
Flow rate: 1.0 ml/min
Detection: 265 nm
Sample concentration: 1 mg/mL in DCM/iPrOH 50/50
Injection: 2 μl
Preparative HPLC Method:
Autopurification System from Waters: 2767 sample Manager, 2489 UV/Visible Detector, 2545
Quaternary Gradient Module.
Column: Daicel CHIRALPAK® IA, 5 μm, 1.0 cm×25 cm
Mobile phase: Hept/EtOAc 80/20
Flow rate: 10 ml/min
Detection: UV 260 nm
Sample concentration: 66 mg/mL in (Heptane/EtOAc 1/1)
Injection: 75 μl-450 μl Results:

| First eluting enantiomer | Second eluting enantiomer |
| --- | --- |
| Retention time (min)~9.13 | Retention time (min)~19.23 |
| Chemical purity (area % at 265 nm) 96 | Chemical purity (area % at 265 nm) 96 |
| Enantiomeric excess (%) >99 | Enantiomeric excess (%) >99 |

The compound with the elution time of 9.13 min is N-[(5S)-3-bromo-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide.

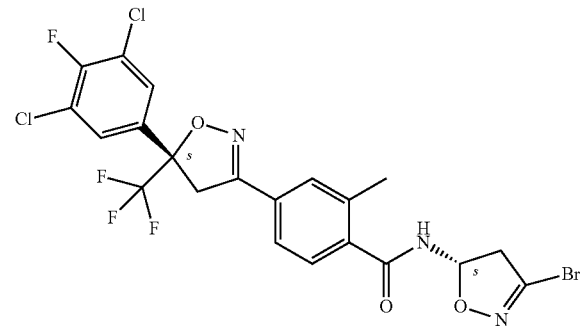

while the compound with the elution time of 19.23 min is N-[(5R)-3-bromo-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide.

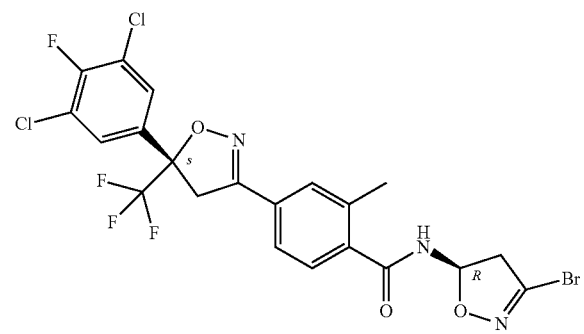

Preparation of the single isomers N-[(5S)-3-methoxy-4,5-dihydroisoxazol-5-yl]-2-methyl-4-[(5S)-5-(3,4,5-trichlorophenyl)-5-(trifluoromethyl)-4H-isoxazol-3-yl]benzamide (Example A148 in Table A) and N-[(5R)-3-methoxy-4,5-dihydroisoxazol-5-yl]-2-methyl-4-[(5S)-5-(3,4,5-trichlorophenyl)-5-(trifluoromethyl)-4H-isoxazol-3-yl]benzamide (Example A149 in Table A

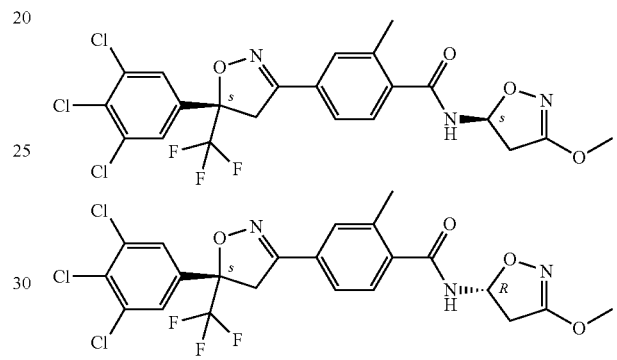

The mixture of isomers, N-[3-methoxy-4,5-dihydroisoxazol-5-yl]-2-methyl-4-[(5S)-5-(3,4,5-trichlorophenyl)-5-(trifluoromethyl)-4H-isoxazol-3-yl]benzamide was submitted to chiral resolution by preparative HPLC chromatography using the conditions outlined hereafter.

Analytical HPLC Method:
HPLC: Waters UPLC-HClass, DAD Detector Waters UPLC
Column: Daicel CHIRALPAK® IA, 3 µm, 0.46 cm×10 cm
Mobile phase: Hept/EtOAc 70/30
Flow rate: 1.0 ml/min
Detection: 265 nm
Sample concentration: 1 mg/mL in DCM/iPrOH 50/50
Injection: 2 µl
Preparative HPLC Method:
Autopurification System from Waters: 2767 sample Manager, 2489 UV/Visible Detector, 2545 Quaternary Gradient Module.
Column: Daicel CHIRALPAK® IA, 5 µm, 1.0 cm×25 cm
Mobile phase: Hept/EtOAc 70/30
Flow rate: 10 ml/min
Detection: UV 2365 nm
Sample concentration: 100 mg/mL in EtOAc
Injection: 200 µl-300 µl
Results:

| First eluting enantiomer | Second eluting enantiomer |
| --- | --- |
| Retention time (min)~6.52 | Retention time (min)~11.93 |
| Chemical purity (area % at 265 nm) 99 | Chemical purity (area % at 265 nm) 99 |
| Enantiomeric excess (%) >99 | Enantiomeric excess (%) >99 |

The compound with the elution time of 6.52 min is N-[(5S)-3-methoxy-4,5-dihydroisoxazol-5-yl]-2-methyl-4-[(5S)-5-(3,4,5-trichlorophenyl)-5-(trifluoromethyl)-4H-isoxazol-3-yl]benzamide.

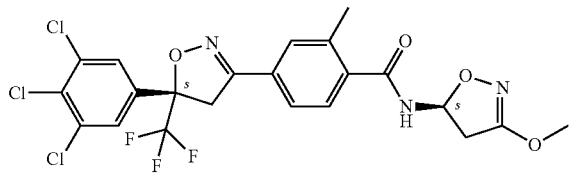 [SMILES: COC1=NO[C@H](NC(=O)c2ccc(C3=NO[C@@](c4cc(Cl)c(Cl)c(Cl)c4)(C(F)(F)F)C3)cc2C)C1]

while the compound with the elution time of 11.93 min is N-[(5R)-3-methoxy-4,5-dihydroisoxazol-5-yl]-2-methyl-4-[(5S)-5-(3,4,5-trichlorophenyl)-5-(trifluoromethyl)-4H-isoxazol-3-yl]benzamide.

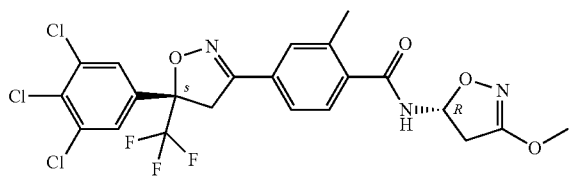

Preparation of the single isomers 4-[(5S)-5-(3,5-dichloro-4-fluoro-phenyl)-5-(trifluoromethyl)-4H-isoxazol-3-yl]-N-[(5S)-3-methoxy-4,5-dihydroisoxazol-5-yl]-2-methyl-benzamide (Example A150 in Table A) and 4-[(5S)-5-(3,5-dichloro-4-fluoro-phenyl)-5-(trifluoromethyl)-4H-isoxazol-3-yl]-N-[(5R)-3-methoxy-4,5-dihydroisoxazol-5-yl]-2-methyl-benzamide (Example A151 in Table A

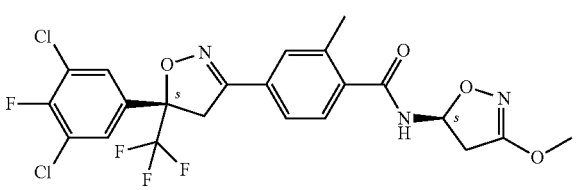 [SMILES: COC1=NO[C@H](NC(=O)c2ccc(C3=NO[C@@](c4cc(Cl)c(F)c(Cl)c4)(C(F)(F)F)C3)cc2C)C1]

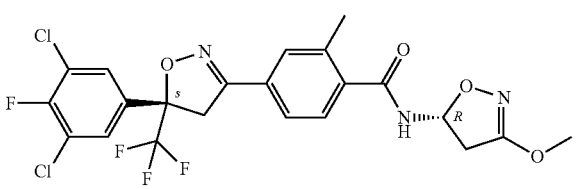 [SMILES: COC1=NO[C@@H](NC(=O)c2ccc(C3=NO[C@@](c4cc(Cl)c(F)c(Cl)c4)(C(F)(F)F)C3)cc2C)C1]

The mixture of isomers, 4-[(5S)-5-(3,5-dichloro-4-fluoro-phenyl)-5-(trifluoromethyl)-4H-isoxazol-3-yl]-N-[3-methoxy-4,5-dihydroisoxazol-5-yl]-2-methyl-benzamide was submitted to chiral resolution by preparative HPLC chromatography using the conditions outlined hereafter.

Analytical HPLC Method:
HPLC: Waters UPLC-HClass, DAD Detector Waters UPLC
Column: Daicel CHIRALPAK® IC, 3 µm, 0.46 cm×10 cm
Mobile phase: Hept/EtOAc 70/30
Flow rate: 1.0 ml/min
Detection: 265 nm
Sample concentration: 1 mg/mL in DCM/iPrOH 50/50
Injection: 2 µl
Preparative HPLC Method:
Autopurification System from Waters: 2767 sample Manager, 2489 UV/Visible Detector, 2545 Quaternary Gradient Module
Column: Daicel CHIRALPAK® IC, 5 µm, 1.0 cm×25 cm
Mobile phase: Hept/EtOAc 70/30
Flow rate: 10 ml/min
Detection: UV 265 nm
Sample concentration: 100 mg/mL in EtOAc
Injection: 50 µl-250 µl
Results:

| First eluting enantiomer | Second eluting enantiomer |
| --- | --- |
| Retention time (min)~7.02 | Retention time (min)~10.18 |
| Chemical purity (area % at 265 nm) 99 | Chemical purity (area % at 265 nm) 99 |
| Enantiomeric excess (%) >99 | Enantiomeric excess (%) > 99 |

The compound with the elution time of 7.02 min is 4-[(5S)-5-(3,5-dichloro-4-fluoro-phenyl)-5-(trifluoromethyl)-4H-isoxazol-3-yl]-N-[(5S)-3-methoxy-4,5-dihydroisoxazol-5-yl]-2-methyl-benzamide.

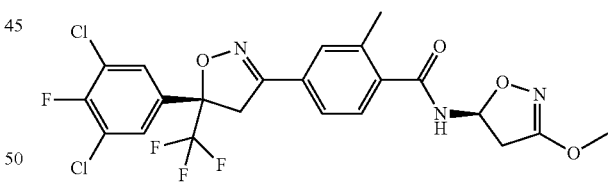

while the compound with the elution time of 10.18 min is 4-[(5S)-5-(3,5-dichloro-4-fluoro-phenyl)-5-(trifluoromethyl)-4H-isoxazol-3-yl]-N-[(5R)-3-methoxy-4,5-dihydroisoxazol-5-yl]-2-methyl-benzamide.

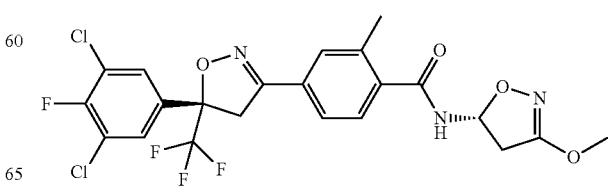

Preparation of the single isomers tert-butyl N-[(5S)-3-methoxy-4,5-dihydroisoxazol-5-yl]-N-[2-methyl-4-[(5S)-5-(3,4,5-trichlorophenyl)-5-(trifluoromethyl)-4H-isoxazol-3-yl]benzoyl]carbamate and tert-butyl N-[(5R)-3-methoxy-4,5-dihydroisoxazol-5-yl]-N-[2-methyl-4-[(5S)-5-(3,4,5-trichlorophenyl)-5-(trifluoromethyl)-4H-isoxazol-3-yl]benzoyl]carbamate (Examples A152 and A153 in Table A Preparation of the single isomers 4-[(5S)-5-(3,5-dichlorophenyl)-5-(trifluoromethyl)-4H-isoxazol-3-yl]-2-methyl-N-[(5S)-3-(trifluoromethyl)-4,5-dihydroisoxazol-5-yl]benzamide and 4-[(5S)-5-(3,5-dichlorophenyl)-5-(trifluoromethyl)-4H-isoxazol-3-yl]-2-methyl-N-[(5R)-3-(trifluoromethyl)-4,5-dihydroisoxazol-5-yl]benzamide (Respectively Examples A154 and A155 in Table A

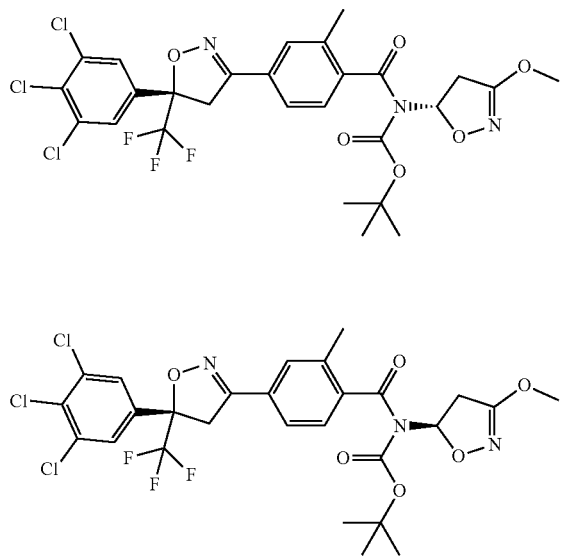

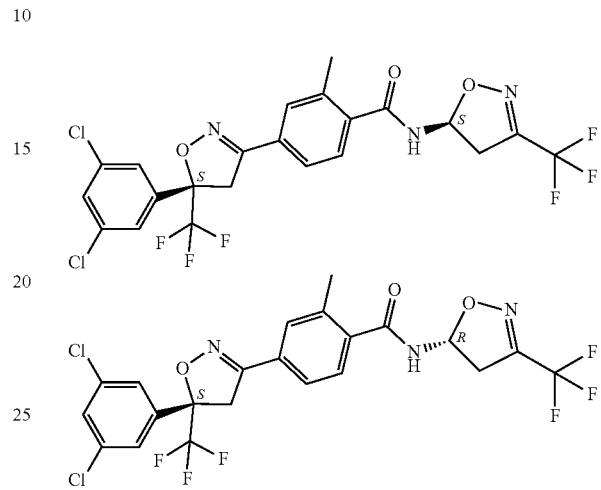

The mixture of isomers, tert-butyl N-[3-methoxy-4,5-dihydroisoxazol-5-yl]-N-[2-methyl-4-[(5S)-5-(3,4,5-trichlorophenyl)-5-(trifluoromethyl)-4H-isoxazol-3-yl]benzoyl]carbamate was submitted to chiral resolution by preparative HPLC chromatography using the conditions outlined hereafter.
Analytical HPLC Method:
HPLC: Waters UPLC-HClass, DAD Detector Waters UPLC
Column: Daicel CHIRALPAK® IB, 3 μm, 0.46 cm×10 cm
Mobile phase: Hept/EtOH 90/10
Flow rate: 1.0 ml/min
Detection: 265 nm
Sample concentration: 1 mg/mL in MeOH
Injection: 2 μl
Preparative HPLC Method:
Autopurification System from Waters: 2767 sample Manager, 2489 UV/Visible Detector, 2545 Quaternary Gradient Module.
Column: Daicel CHIRALPAK® IA, 5 μm, 1.0 cm×25 cm
Mobile phase: Hept/iPr 80/20
Flow rate: 10 ml/min
Detection: UV 265 nm
Sample concentration: 27 mg/mL in DCM/iPr
Injection: 300 μl-400 μl
Results:

The mixture of isomers, 4-[(5S)-5-(3,5-dichlorophenyl)-5-(trifluoromethyl)-4H-isoxazol-3-yl]-2-methyl-N-[3-(trifluoromethyl)-4,5-dihydroisoxazol-5-yl]benzamide was submitted to chiral resolution by preparative HPLC chromatography using the conditions outlined hereafter.
Analytical HPLC Method:
SFC: Waters Acquity UPC$^2$/QDa
PDA Detector Waters Acquity UPC$^2$
Column: Daicel SFC CHIRALPAK® IA, 3 μm, 0.3 cm×10 cm, 40° C.
Mobile phase: A: CO2 B: EMI
gradient: 10% B in 4.8 min
ABPR: 1800 psi
Flow rate: 2.0 ml/min
Detection: 265 nm
Sample concentration: 1 mg/mL in Hept/iPr 50/50
Injection: 1 μL
Preparative HPLC Method:
Autopurification System from Waters: 2767 sample Manager, 2489 UV/Visible Detector, 2545 Quaternary Gradient Module.
Column: Daicel CHIRALPAK® IC, 5 μm, 1.0 cm×25 cm
Mobile phase: Hept/iPr 90/10
Flow rate: 10 ml/min
Detection: UV 220 nm
Sample concentration: 140 mg/mL in DCM/EE 1/2
Injection: 70 μL

| First eluting enantiomer: compound A152 | Second eluting enantiomer: compound A153 |
|---|---|
| Retention time (min)~9.22 | Retention time (min)~7.64 |
| Chemical purity (area % at 265 nm) 99 | Chemical purity (area % at 265 nm) 99 |
| Enantiomeric excess (%) >99 | Enantiomeric excess (%) >99 |

Results:

| First eluting enantiomer: compound A154 | Second eluting enantiomer: compound A155 |
|---|---|
| Retention time (min)~2.22 | Retention time (min)~3.20 |
| Chemical purity (area % at 265 nm) 95 | Chemical purity (area % at 265 nm) 99 |
| Enantiomeric excess (%) >91 | Enantiomeric excess (%) >99 |

Preparation of the single isomers 4-[(5S)-5-(3,5-dichlorophenyl)-5-(trifluoromethyl)-4H-isoxazol-3-yl]-2-methyl-N-[(5S)-3-(2,2,2-trifluoroethoxy)-4,5-dihydroisoxazol-5-yl]benzamide and 4-[(5S)-5-(3,5-dichlorophenyl)-5-(trifluoromethyl)-4H-isoxazol-3-yl]-2-methyl-N-[(5R)-3-(2,2,2-trifluoroethoxy)-4,5-dihydroisoxazol-5-yl]benzamide (Respectively Examples A156 and A157 in Table A Mobile phase: A: CO2 B: EMI gradient: 10% B in 4.8 min
ABPR: 1800 psi
Flow rate: 2.0 ml/min
Detection: 265 nm
Sample concentration: 1 mg/mL in Hept/iPr 50/50
Injection: 1 µL
Preparative HPLC Method:
Autopurification System from Waters: 2767 sample Manager, 2489 UV/Visible Detector, 2545 Quaternary Gradient Module.
Column: Daicel CHIRALPAK® IC, 5 µm, 1.0 cm×25 cm
Mobile phase: Hept/iPr 90/10
Flow rate: 10 ml/min
Detection: UV 220 nm
Sample concentration: 140 mg/mL in DCM/EE 1/2
Injection: 70 µl
Results:

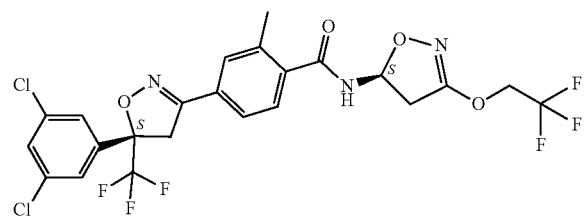

| First eluting enantiomer: compound A156 | Second eluting enantiomer: compound A157 |
|---|---|
| Retention time (min)~3.56 | Retention time (min)~4.96 |
| Chemical purity (area % at 265 nm) 95 | Chemical purity (area % at 265 nm) 95 |
| Enantiomeric excess (%) >93 | Enantiomeric excess (%) >93 |

-continued

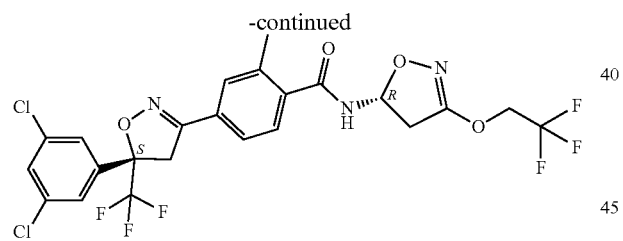

Preparation of the single isomers 4-[(5S)-5-(3,5-dichlorophenyl)-5-(trifluoromethyl)-4H-isoxazol-3-yl]-N-[(5S)-3-ethoxy-4,5-dihydroisoxazol-5-yl]-2-methyl-benzamide and 4-[(5S)-5-(3,5-dichlorophenyl)-5-(trifluoromethyl)-4H-isoxazol-3-yl]-N-[(5R)-3-ethoxy-4,5-dihydroisoxazol-5-yl]-2-methyl-benzamide (Respectively Examples A158 and A159 in Table A The mixture of isomers, 4-[(5S)-5-(3,5-dichlorophenyl)-5-(trifluoromethyl)-4H-isoxazol-3-yl]-2-methyl-N-[3-(2,2,2-trifluoroethoxy)-4,5-dihydroisoxazol-5-yl]benzamide was submitted to chiral resolution by preparative HPLC chromatography using the conditions outlined hereafter.
Analytical HPLC Method:
SFC: Waters Acquity UPC²/QDa
PDA Detector Waters Acquity UPC²
Column: Daicel SFC CHIRALPAK® IA, 3 µm, 0.3 cm×10 cm, 40° C.

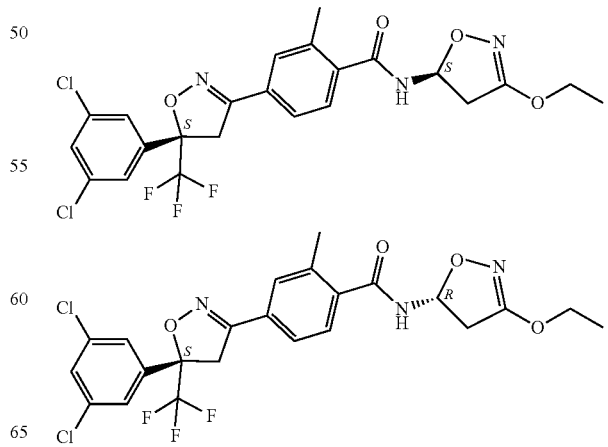

The mixture of isomers, 4-[(5S)-5-(3,5-dichlorophenyl)-5-(trifluoromethyl)-4H-isoxazol-3-yl]-N-[3-ethoxy-4,5-dihydroisoxazol-5-yl]-2-methyl-benzamide was submitted to chiral resolution by preparative HPLC chromatography using the conditions outlined hereafter.

Analytical HPLC Method:
Column: Daicel CHIRALPAK® IC, 5 μm, 0.46 cm×25 cm
Mobile phase: Hept/EtOH/Diethylamine 90/10
Flow rate: 1.0 ml/min
Detection: DAD 270 nm
Sample dissolved in EtOH
Temperature: 25 C Preparative HPLC Method:
Column: Daicel CHIRALPAK® IC, 5 μm, 3 cm×25 cm
Mobile phase: Carbon Dioxide/Methanol 60/40
Flow rate: 120 ml/min
Temperature: 25 C
Outlet pressure: 130 bar
Results:

| First eluting enantiomer: compound A158 | Second eluting enantiomer: compound A159 |
|---|---|
| Retention time (min)~7.3 | Retention time (min)~12.2 |
| Chemical purity (area % at 265 nm) 91.6 | Chemical purity (area % at 265 nm) 93.0 |
| Enantiomeric excess (%) >99.5 | Enantiomeric excess (%) >99.5 |

Preparation of N-(3-bromo-4,5-dihydroisoxazol-5-yl)formamide

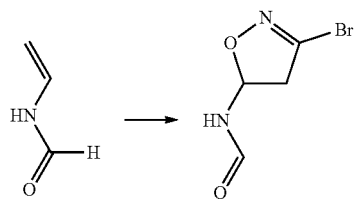

To a cooled (0-5° C.) solution of N-vinylformamide (13.0 g) in Ethyl acetate (366 mL), was added a solution of sodium bicarbonate (77.6 g) in water (183 mL). After 15 min, to this bi-phasic suspension was added a solution of dibromomethanone oxime (40.8 g) in Ethyl acetate (50 mL), while maintaining the temperature between 5-10° C. (a slow gas evolution was observed). After completion of the the addition, the reaction was further stirred at room temperature (rt) for 3.5 hours. The mixture was then extracted twice between ethyl acetate and water. The combined organic layers were dried (MgSO4), filtered and evaporated under vacuo to give 32.6 g of a cloudy brown oil, which corresponds to the desired N-(3-bromo-4,5-dihydroisoxazol-5-yl)formamide and could be used as such in the next steps.

1H-NMR (CDCl3, 400 MHz, δ in ppm): 3.02-3.19 (m, 1H) 3.49-3.66 (m, 1H) 5.86-6.43 (m, 1H) 6.84-7.25 (m, 1H) 8.16-8.31 (m, 1H)

Preparation of tert-butyl N-(3-bromo-4,5-dihydroisoxazol-5-yl)carbamate

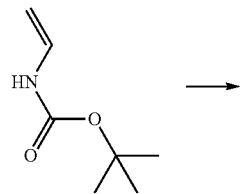

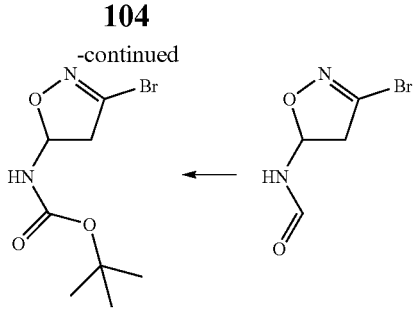

Method 1: from tert-butyl N-vinylcarbamate

A suspension of tert-butyl N-vinylcarbamate (25.0 g) and Potassium carbonate (49.2 g) in Tetrahydrofuran (262 mL) was cooled to 0-5° C. To this mixture was then added a solution of dibromomethanone oxime (39.0 g) in tetrahydrofuran (89.0 mL) at 0-5° C. and was stirred for one hour.

The reaction mixture was then stirred at rt for 3 hours. The mixture was then extracted twice between ethyl acetate and water. The combined organic layers were dried (MgSO4), filtered and evaporated under vacuo to give a 46.1 g of a crude compound.

30 g of this crude were stirred with 50 ml of diethylether for 2 hours. The resulting beige suspension was filtered, washed with 2×20 ml of diethylether and 2×50 ml of pentane then was dried under vacuo to give 26.54 g of a white solid corresponding to the desired tert-butyl N-(3-bromo-4,5-dihydroisoxazol-5-yl)carbamate. 1H-NMR (CDCl3, 400 MHz, δ in ppm): 1.47 (s, 9H) 2.95 (dd, J=18, 4.8 Hz, 1H) 3.49 (dd, J=18, 9.7 Hz, 1H) 5.42 (br. s., 1H) 6.15 (br. s., 1H)

Method 2: from N-(3-bromo-4,5-dihydroisoxazol-5-yl)formamide

In a round bottom flask, N-(3-bromo-4,5-dihydroisoxazol-5-yl)formamide (200 mg) was dissolved in tetrahydrofuran (2 mL) then 4-(dimethylamino)pyridine (DMAP, 190 mg) was added at rt. The reaction mixture was cooled and the mixture was kept between 5° C. and 10° C. then a solution of tert-butoxycarbonyl tert-butyl carbonate (250 mg) in THF (2 mL) was added dropwise over a period of 5 min. The resulting mixture was stirred for 4 hr at rt. Then a solution of NaOH (5.18 mL, 1N) was added at rt and the mixture was then stirred for one hour. The mixture was diluted with ethyl acetate then washed with water and brine. The combined organic phases were dried (MgSO4), filtered and evaporated under vacuo to give a crude mixture, which was then purified by using a Rf Combiflash apparatus, using silica gel and eluted with cyclohexane/EtOAc (100/0 to 70/30). Thus, 185 mg of tert-butyl N-(3-bromo-4,5-dihydroisoxazol-5-yl)carbamate was obtained. 1H-NMR (DMSO-d6, 400 MHz, δ in ppm): 1.40 (s, 9H) 2.94 (dd, J=17.8, 4.6 Hz, 1H) 3.53 (dd, J=17.8, 9.7 Hz, 1H) 5.91 (td, J=9.6, 4.4 Hz, 1H) 8.29 (d, J=9.6 Hz, 1H)

Preparation of tert-butyl N-(3-methoxy-4,5-dihydroisoxazol-5-yl)carbamate

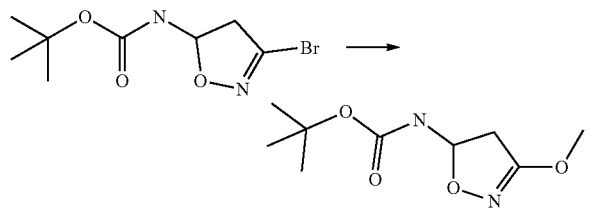

To a suspension of tert-butyl N-(3-bromo-4,5-dihydroisoxazol-5-yl)carbamate (21.3 g) in methanol (256 mL), was added sodium methanolate (30% in methanol, 22 mL) at ambient temperature and the solution was stirred for 24 h. Then the mixture was extracted with brine and ethyl acetate, the organic layer was washed with brine, dried over anhydrous sodium sulfate and the solvent evaporated. The residue was suspended in ~70 ml of diethylether and stirred for 2 hours. The resulting suspension was filtered and the solid was washed with ~25 ml diethylethe and then with 3×40 ml of pentane. The solid was dried under vacuo to give 12.18 g of tert-butyl N-(3-methoxy-4,5-dihydroisoxazol-5-yl)carbamate as a white solid. $^1$H NMR (400 MHz, CDCl3) δ ppm 1.46 (s, 9H) 2.68 (dd, J=17.2, 4.0 Hz, 1H) 3.29 (br dd, J=17.2, 8.8 Hz, 1H) 3.87 (s, 3H) 5.34-5.53 (m, 1H) 5.97-6.17 (m, 1H).

Using a similar procedure, using tert-butyl N-(3-bromo-4,5-dihydroisoxazol-5-yl)carbamate and Sodium ethoxide, the compound tert-butyl N-(3-ethoxy-4,5-dihydroisoxazol-5-yl)carbamate could be prepared. $^1$H NMR (400 MHz, CDCl3) δ ppm 1.35 (t, J=6.9 Hz, 3H) 1.46 (s, 9H) 2.67 (dd, J=17.1, 4.2 Hz, 1H) 3.29 (dd, J=17.1, 8.9 Hz, 1H) 4.21 (q, J=7.1 Hz, 2H) 5.29-5.54 (m, 1H) 5.92-6.16 (m, 1H) Using a similar procedure, using N-(3-bromo-4,5-dihydroisoxazol-5-yl)acetamide and Sodium methoxide, the compound N-(3-methoxy-4,5-dihydroisoxazol-5-yl)acetamide could be prepared. $^1$H NMR (400 MHz, CDCl3) δ ppm 2.02 (s, 3H) 2.74 (dd, J=17.2, 3.7 Hz, 1H) 3.34 (dd, J=17.2, 8.8 Hz, 1H) 3.88 (s, 3H) 6.26 (td, J=8.6, 4.0 Hz, 1H) 6.34-6.58 (m, 1H)

Preparation of benzyl N-(3-bromo-4,5-dihydroisoxazol-5-yl)-N-formyl-carbamate

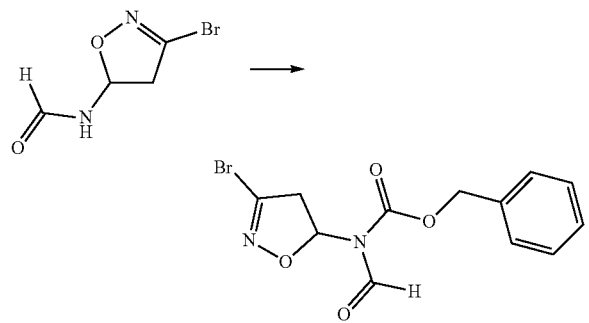

To a cold mixture of N-(3-bromo-4,5-dihydroisoxazol-5-yl)formamide (0.567 g) in THF (16 ml), kept between 5° C. to 10° C., sodium hydride (60% in mineral oil, 0.074 g) was added and the reaction mixture was stirred for additional 20 min at ambient temperature. To this mixture was then added benzyl chloroformate (0.5 g) and the reaction was stirred for 2 days at r.t. Then some additional sodium hydride (60% in mineral oil, 0.075 g) and benzyl chloroformate (B, 0.5 g) were added at 0° C. and the mixture was stirred for another 20 min. To this mixture was then added a saturated solution of NH4Cl (20 ml). Then EtOAc (30 ml) was added and the water phase was extracted with EtOAc (2×30 ml). The combined organic phases were dried (MgSO4), filtered and evaporated under vacuo to give a crude mixture, which was then purified by using a Rf Combiflash apparatus, using silica gel and eluted with cyclohexane/EtOAc (100/0 to 50/50). Thus 507 mg of benzyl N-(3-bromo-4,5-dihydroisoxazol-5-yl)-N-formyl-carbamate was obtained. 1H-NMR (CDCl3, 400 MHz, δ in ppm): 3.26-3.52 (m, 2H) 5.25-5.41 (m, 2H) 6.70-6.81 (m, 1H) 7.32-7.49 (m, 5H) 9.21 (s, 1H)

Preparation of N-(3-bromo-4,5-dihydroisoxazol-5-yl)-N-formyl-acetamide

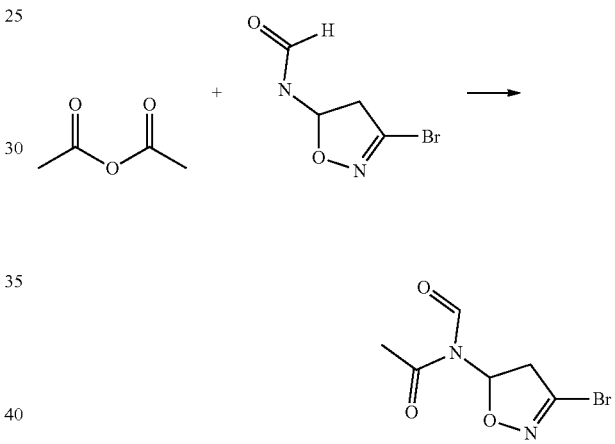

To a mixture of N-(3-bromo-4,5-dihydroisoxazol-5-yl)formamide (1 g) in THF (25 ml), was added DMAP at ambient temperature then reaction mixture was cooled and the mixture was kept between 5° C. and 10° C. To this mixture, acetic anhydride (0.55 ml) was added dropwise over a period of 5 min and the resulting mixture was stirred at ambient temperature for 20 hours. Then EtOAc and water were added and the water phase was extracted with EtOAc. The combined organic phases were dried over anhydrous magnesium sulfate, filtered and evaporated under vacuo to give a solid (950 mg), which contained N-(3-bromo-4,5-dihydroisoxazol-5-yl)-N-formyl-acetamide, that could be used as such in the next step. 1H-NMR (CDCl3, 400 MHz, δ in ppm): 2.47 (s, 3H) 3.26-3.40 (m, 1H) 3.40-3.54 (m, 1H) 6.66-6.88 (m, 1H) 9.09 (s, 1H)

N-(3-bromo-4,5-dihydroisoxazol-5-yl)acetamide could also be isolated from the same reaction however by performing a basic work up (Sodium hydroxide solution). 1H-NMR (CDCl3, 400 MHz, δ in ppm): 2.03 (s, 3H) 2.93-3.10 (m, 1H) 3.46-3.62 (m, 1H) 6.34 (td, J=9.2, 4.0 Hz, 1H) 6.40-6.60 (m, 1H)

Preparation of benzyl N-(3-methoxy-4,5-dihydroisoxazol-5-yl)carbamate

Step 1: Preparation of benzyl N-formyl-N-vinyl-carbamate

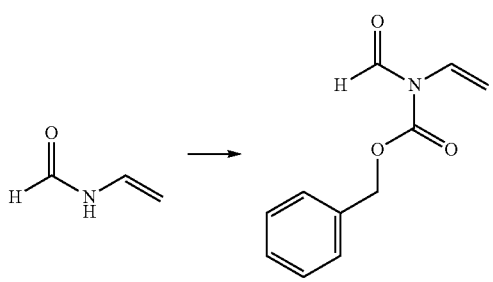

To the cold suspension of sodium hydride (60% in mineral oil, 1.98 g) in THF (110 mL) was added dropwise N-vinyl-formamide (1.7 g) and the mixture was stirred for 10 min at 0° C. To this reaction mixture was then added benzyl chloroformate (4 g) portion wise. The reaction mixture was stirred at r.t. for 7 h. To this mixture was then added a saturated solution of NH$_4$Cl (50 ml). Then the water phase was extracted with EtOAc (2×50 ml). The combined organic phases were dried (Na2SO$_4$), filtered and evaporated under vacuo to give a crude mixture, which was then purified by using a Rf Combiflash apparatus, using silica gel and eluted with cyclohexane/EtOAc (100/0 to 50/50). Thus 2 g of benzyl N-formyl-N-vinyl-carbamate was obtained. 1H-NMR (CDCl3, 400 MHz, δ in ppm): 5.13 (d, J=9.5 Hz, 1H) 5.35 (s, 2H) 5.71 (d, J=16.1 Hz, 1H) 6.62 (dd, J=16.1, 9.5 Hz, 1H) 7.31-7.45 (m, 5H) 9.33 (s, 1H).

Step 2: Preparation of benzyl N-(3-bromo-4,5-dihydroisoxazol-5-yl)-N-formyl-carbamate

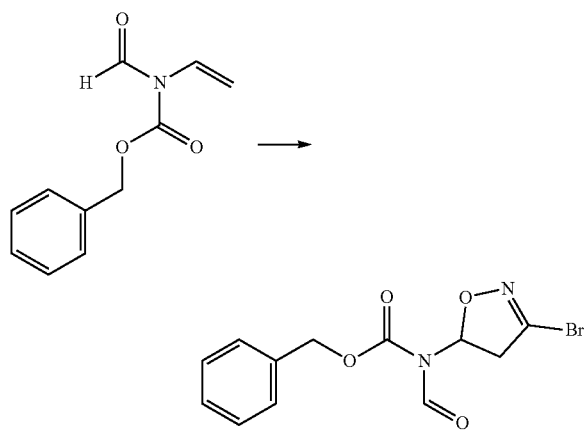

To a solution of benzyl N-formyl-N-vinyl-carbamate (1.2 g) dissolved in ethyl acetate (29 ml), was added a solution of saturated sodium hydrogencarbonate (29 ml) and sodium hydrogencarbonate (2.53 g). To this reaction mixture, dibromomethanone oxime (2.42 g) was added and the reaction was stirred for 18 h. To this mixture was then added a saturated solution of NH$_4$Cl (30 ml). Then the water phase was extracted with EtOAc (3×50 ml). The combined organic phases were dried (MgSO4), filtered and evaporated under vacuo to give a crude mixture, which was then purified by using a Rf Combiflash apparatus, using silica gel and eluted with cyclohexane/EtOAc (100/0 to 50/50). Thus, 1.39 g of benzyl N-(3-bromo-4,5-dihydroisoxazol-5-yl)-N-formyl-carbamate was obtained. 1H-NMR (CDCl3, 400 MHz, δ in ppm): 3.25-3.49 (m, 2H) 5.23-5.40 (m, 2H) 6.76 (dd, J=11.0, 5.5 Hz, 1H) 7.32-7.48 (m, 5H) 9.21 (s, 1H)

Step 3: Preparation of benzyl N-(3-methoxy-4,5-dihydroisoxazol-5-yl)carbamate

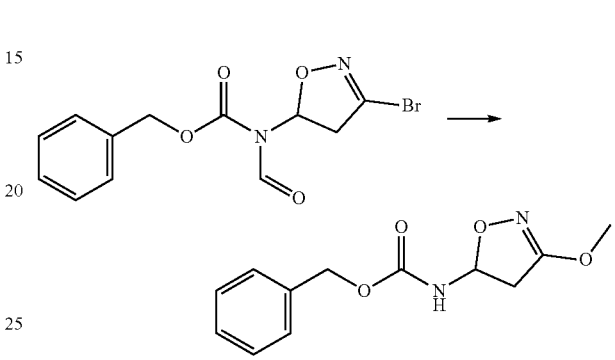

To a solution of benzyl N-(3-bromo-4,5-dihydroisoxazol-5-yl)-N-formyl-carbamate 1.67 g in methanol (51 ml) was added at rt, Cs2CO3 (1.68 g) and the reaction mixture was stirred at r.t. for 18 h. To the obtained mixture was added EtOAc (30 ml) then organic phase was washed with Brine (2×30 ml). The combined organic phases were dried (Na2SO4), filtered and evaporated under vacuo to give a crude mixture, which was then purified by using a Rf Combiflash apparatus, using silica gel and eluted with cyclohexane/EtOAc (100/0 to 50/50). Thus, 0.377 g of of benzyl N-(3-methoxy-4,5-dihydroisoxazol-5-yl)carbamate was obtained. 1H-NMR (CDCl3, 400 MHz, δ in ppm): 2.73 (d, J=14 Hz, 1H) 3.24-3.42 (m, 1H) 3.88 (s, 3H) 5.04-5.27 (m, 2H) 5.64 (br. s., 1H) 6.09 (br. s., 1H) 7.29-7.44 (m, 5H).

Preparation of 4-acetyl-N-formyl-2-methyl-N-vinyl-benzamide and 4-acetyl-2-methyl-N-vinyl-benzamide

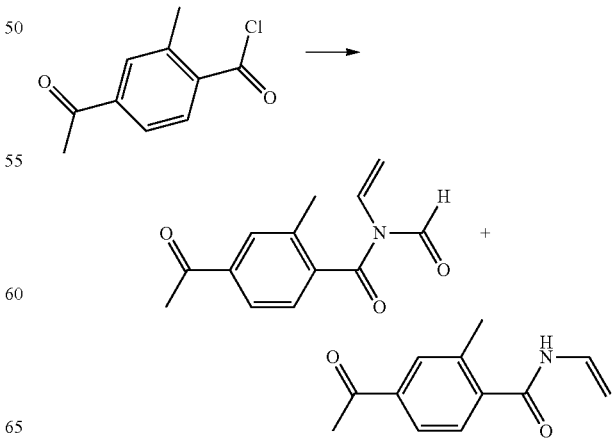

N-Vinylformamide (6.69 g), Triethylamine (17.7 mL) and 4-(Dimethylamino)pyridine (1.04 g) were dissolved in dichloromethane (99.0 mL) and this solution was cooled to 0-5 C. To this solution, a solution of 4-acetyl-2-methyl-benzoyl chloride (16.5 g) in dichloromethane (66.0 mL) was added dropwise. The dark brown mixture obtained was stirred at rt for 3 hours. The mixture was then extracted twice between Dichloromethane and water. The combined organic layers were dried (MgSO4), filtered and evaporated to give a crude residue. This crude product was absorbed on isolute and purified by chromatography with 0-100% EtOAc/Cyclohexane (using the Rf Combiflash apparatus) to give 2 compounds. Thus, 10.16 g of 4-acetyl-N-formyl-2-methyl-N-vinyl-benzamide was obtained and 5.72 g of 4-acetyl-2-methyl-N-vinyl-benzamide was obtained. 4-acetyl-N-formyl-2-methyl-N-vinyl-benzamide: 1H-NMR (CDCl3, 400 MHz, δ in ppm): 2.43 (s, 3H) 2.64 (s, 3H) 5.23 (d, J=9.5 Hz, 1H) 5.72 (d, J=16.1 Hz, 1H) 6.73 (ddd, J=16.3, 9.5, 0.9 Hz, 1H) 7.42 (d, J=8.1 Hz, 1H) 7.78-7.92 (m, 2H) 8.94 (s, 1H).

4-acetyl-2-methyl-N-vinyl-benzamide: 1H-NMR (CDCl3, 400 MHz, δ in ppm): 2.52 (s, 3H) 2.61 (s, 3H) 4.54-4.62 (m, 1H) 4.76 (dd, J=15.8, 0.7 Hz, 1H) 7.16 (ddd, J=15.8, 11.00, 8.8 Hz, 1H) 7.43-7.57 (m, 2H) 7.73-7.87 (m, 2H)

Preparation of 4-acetyl-N-(3-bromo-4,5-dihydroisoxazol-5-yl)-2-methyl-benzamide

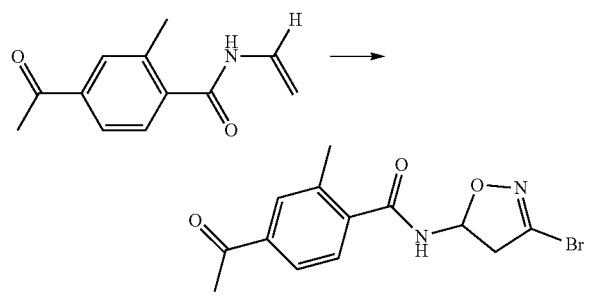

4-acetyl-2-methyl-N-vinyl-benzamide (4.50 g) was dissolved in Ethyl acetate (40.5 mL) and to this solution, a saturated solution of sodium hydrogencarbonate (40.5 mL) and sodium hydrogencarbonate (9.39 g) were added at rt. To this suspension, dibromomethanone oxime (5.84 g) was slowly added (a slight gas evolution was observed) and the reaction mixture was stirred at rt for 18 h. An additional amount of dibromomethanone oxime (1.80 g) was added and the reaction mixture was stirred for 4 hours. The mixture was then extracted twice between ethyl acetate and NaHCO3 sat. The combined organic layers were dried (MgSO4), filtered and evaporated to give a crude residue. This crude product was suspended in 40 ml Diisopropylether and stirred at RT for 30 minutes. The resulting solid was filtered, washed with 2×15 ml DIPE and 2×20 ml Pentane. The solid was dried under vacuo to give 6.67 g of 4-acetyl-N-(3-bromo-4,5-dihydroisoxazol-5-yl)-2-methyl-benzamide. 1H-NMR (CDCl3, 400 MHz, δ in ppm): 2.50 (s, 3H) 2.61 (s, 3H) 3.15 (dd, J=18.2, 4.2 Hz, 1H) 3.66 (dd, J=18.0, 9.5 Hz, 1H) 6.53 (td, J=9.2, 4.0 Hz, 1H) 6.74 (d, J=8.8 Hz, 1H) 7.45 (d, J=8.1 Hz, 1H) 7.75 (d, J=7.70 Hz, 1H) 7.79 (s, 1H).

Preparation of 4-acetyl-N-(3-bromo-4,5-dihydroisoxazol-5-yl)-N-formyl-2-methyl-benzamide

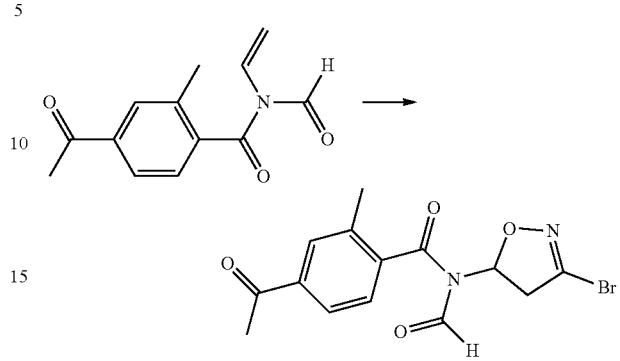

4-acetyl-N-formyl-2-methyl-N-vinyl-benzamide (8.41 g) was dissolved in Ethyl acetate (84.1 mL) and a saturated solution of sodium hydrogencarbonate (84.1 mL) and sodium hydrogencarbonate (15.4 g) were added at rt. To this suspension, dibromomethanone oxime (9.59 g) was slowly added (a slight gas evolution was observed) and the reaction mixture was stirred at rt for 18 h. An additional amount of dibromomethanone oxime (2.95 g) was added and the reaction mixture was stirred for 4 hours. The mixture was then extracted twice between ethyl acetate and NaHCO3 sat. The combined organic layers were dried (MgSO4), filtered and evaporated to give a crude residue. This crude product was absorbed on isolute and purified by chromatography with 0-100% EtOAc/Cyclohexane (using the Rf Combiflash apparatus) to give 9.87 g of 4-acetyl-N-(3-bromo-4,5-dihydroisoxazol-5-yl)-N-formyl-2-methyl-benzamide. 1H-NMR (CDCl3, 400 MHz, δ in ppm): 2.43 (s, 3H) 2.64 (s, 3H) 3.43-3.63 (m, 2H) 6.88 (dd, J=10.3, 5.9 Hz, 1H) 7.35-7.49 (m, 1H) 7.84-7.95 (m, 2H) 8.65 (s, 1H).

Preparation of 4-acetyl-N-(3-methoxy-4,5-dihydroisoxazol-5-yl)-2-methyl-benzamide

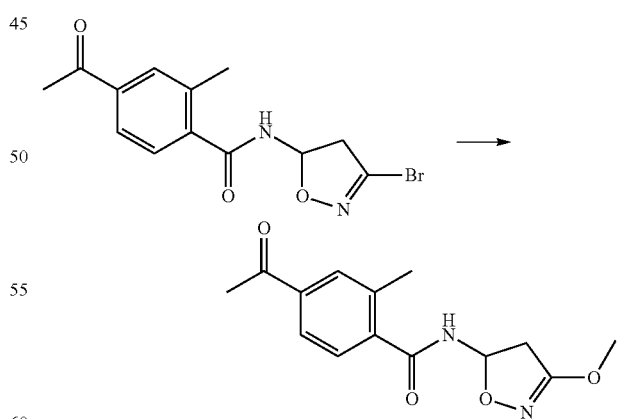

To a solution of 4-acetyl-N-(3-bromo-4,5-dihydroisoxazol-5-yl)-2-methyl-benzamide (1.65 g) suspended in Methanol (16.5 mL) was added a sodium methylate solution (30% in Methanol, 1.74 mL) at rt. The reaction mixture was stirred at rt for 21 hours then the reaction mixture was concentrated under vacuo. The residue was extracted twice between ethyl acetate and water. The combined organic layers were dried (MgSO4), filtered and evaporated uncer vacuo to give a crude residue. The crude residue was suspended in 40 mL Diisopropylether and stirred for 1 hour at rt. The suspension was filtered, the solid was washed with 2×10 mL of Diisopropylether and 2×20 mL of Pentane. The solid was dried under vauco to give 1.18 g of 4-acetyl-N-(3-methoxy-4,5-dihydroisoxazol-5-yl)-2-methyl-benzamide. 1H-NMR (CDCl3, 400 MHz, δ in ppm): 2.51 (s, 3H) 2.61 (s, 3H) 2.86 (dd, J=17.2, 3.7 Hz, 1H) 3.39-3.53 (m, 1H) 3.90 (s, 3H) 6.45 (td, J=8.6, 3.7 Hz, 1H) 6.64 (d, J=8.4 Hz, 1H) 7.47 (d, J=8.1 Hz, 1H) 7.73-7.86 (m, 2H).

Preparation of 4-acetyl-N-(3-ethoxy-4,5-dihydroisoxazol-5-yl)-2-methyl-benzamide

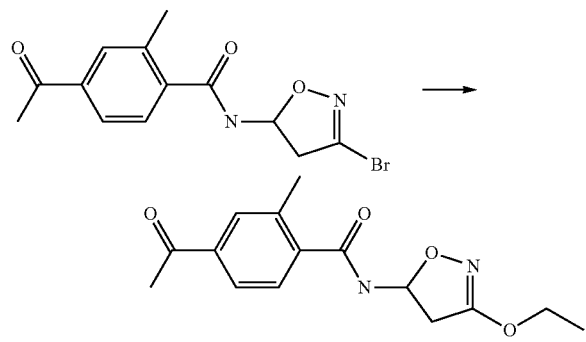

A mixture of 4-acetyl-N-(3-bromo-4,5-dihydroisoxazol-5-yl)-2-methyl-benzamide (3.50 g) suspended in ethanol (10 mL) was cooled at 0° C. with ice/H2O bath. Sodium ethylate solution (21% in Methanol, 7.3 mL) was added dropwise over 1 hour. The reaction mixture was allowed to warm up to rt and stirred at rt for 1.5 hour. After addition of H2O to the reaction mixture, some solid was formed. It was filtered and washed with H2O; it was dissolved in DCM, dried (Na₂SO₄), filtered and evaporated to give 1.15 g of 4-acetyl-N-(3-ethoxy-4,5-dihydroisoxazol-5-yl)-2-methyl-benzamide.

The mother liquor from reaction mixture was extracted three times with AcOEt. The combined organic layers were dried (Na₂SO₄), filtered and evaporated to give a crude residue. This crude product was purified by silica gel column (cyclohexane—AcOEt 7:3) to give 300 mg of 4-acetyl-N-(3-ethoxy-4,5-dihydroisoxazol-5-yl)-2-methyl-benzamide. 1H-NMR (DMSO, 400 MHz, δ in ppm): 1.28 (t, J=7.1 Hz, 3H) 2.40 (s, 3H) 2.59 (s, 3H) 2.86 (dd, J=16.9, 4.4 Hz, 1H) 3.35-3.41 (m, 1H) 4.12 (q, J=7.0 Hz, 2H) 6.17-6.23 (m, 1H) 7.47 (d, J=7.7 Hz, 1H) 7.81-7.84 (m, 2H) 9.5 (bd, J=8.8 Hz, 1H).

Preparation of 4-acetyl-N-(3-Chloro-4,5-dihydroisoxazol-5-yl)-2-methyl-benzamide

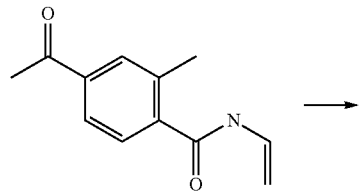

-continued

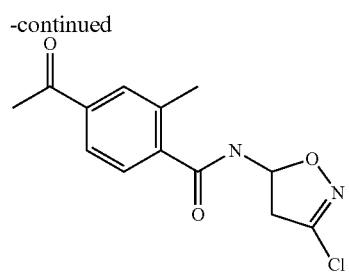

4-acetyl-2-methyl-N-vinyl-benzamide (12.47 g) was dissolved in ethyl acetate (49 mL) and to this solution a saturated solution of sodium hydrogencarbonate (63 mL) and solid sodium hydrogencarbonate (14.48 g) were added at rt. To this suspension, dichloromethanone oxime (55 ml, 0.94M in DME) was slowly added at 0° C. and the reaction mixture was allowed to warm up to rt. An additional amount of dichloromethanone oxime (50 ml, 0.94M in DME) was added during 3 h30 and then the reaction mixture was stirred for 18 hours at rt. The mixture was then extracted twice between ethyl acetate and H2O. The combined organic layers were dried (Na₂SO₄), filtered and evaporated to give a crude residue. This crude product was suspended in 20 ml of mixture AcOEt and Et2O (1:1) and stirred at RT for 30 minutes. The resulting solid was filtered and dried in vacuum to give 5.2 g of 4-acetyl-N-(3-chloro-4,5-dihydroisoxazol-5-yl)-2-methyl-benzamide. ¹H-NMR (DMSO, 400 MHz, δ in ppm): 2.40 (s, 3H) 2.59 (s, 3H) 3.10 (dd, J=18.0, 4.0 Hz, 1H) 3.66 (dd, J=17.8, 9.7 Hz, 1H) 6.53 (bs, 1H) 7.5 (d, J=8.0 Hz, 1H) 7.82 (m, 2H) 7.79 (bd, J=7.3 Hz, 1H).

Preparation of 4-[3-(3,5-dichloro-4-fluoro-phenyl)-4,4,4-trifluoro-3-hydroxy-butanoyl]-N-(3-methoxy-4,5-dihydroisoxazol-5-yl)-2-methyl-benzamide

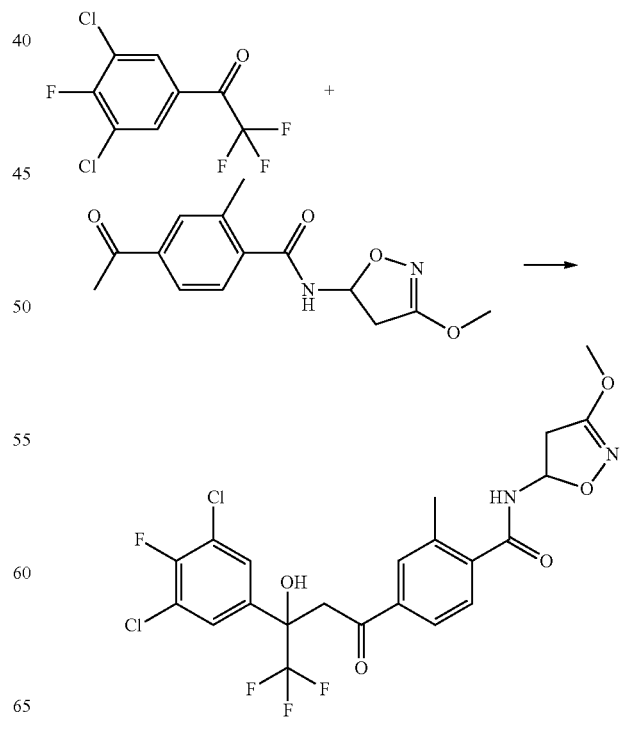

A solution of 4-acetyl-N-(3-methoxy-4,5-dihydroisoxazol-5-yl)-2-methyl-benzamide (0.5 g) was suspended in Toluene (5.0 mL) then 1-(3,5-dichloro-4-fluoro-phenyl)-2,2,2-trifluoro-ethanone (0.71 g) was added with Triethylamine (0.25 mL). The suspension was stirred and heated at 40° C. for 6 hours. Then an additional amount of triethylamine (0.25 mL) was added and the reaction mixture was stirred at 80° C. for 2 hours. The reaction mixture was allowed to stand at rt for 17 hours then the mixture was heated to 120° C. for 8.5 hours. The reaction mixture was allowed to stand at rt for ca 65 hours then it was extracted twice between ethyl acetate and water. The combined organic layers were dried (MgSO$_4$), filtered, and evaporated under vacuo to give a crude residue. This crude product was absorbed on isolute and purified by chromatography with 0-100% EtOAc/Cyclohexane (using the Rf Combiflash apparatus) to give 343 mg of 4-[3-(3,5-dichloro-4-fluoro-phenyl)-4,4,4-trifluoro-3-hydroxy-butanoyl]-N-(3-methoxy-4,5-dihydroisoxazol-5-yl)-2-methyl-benzamide. 1H-NMR (CDCl3, 400 MHz, δ in ppm):

2.53 (s, 3H) 2.86 (dd, J=17.2, 3.7 Hz, 1H) 3.48 (dd, J=17.2, 8.8 Hz, 1H) 3.63-3.74 (m, 1H) 3.77-3.88 (m, 1H) 3.90 (s, 3H) 6.44 (td, J=8.7, 3.7 Hz, 1H) 6.57 (d, J=8.1 Hz, 1H) 7.50-7.54 (m, 1H) 7.57 (d, J=6.2 Hz, 2H) 7.72-7.82 (m, 2H)

In a similar type of reaction, 4-[3-(3,5-dichlorophenyl)-4,4,4-trifluoro-3-hydroxy-butanoyl]-N-(3-ethoxy-4,5-dihydroisoxazol-5-yl)-2-methyl-benzamide was prepared: To a suspension of 4-acetyl-N-(3-ethoxy-4,5-dihydroisoxazol-5-yl)-2-methyl-benzamide (11 g) in dry 1,4-dioxane (55 mL), 1-(3,5-dichlorophenyl)-2,2,2-trifluoro-ethanone (14 g) was added dropwise at 23° C., followed by triethylamine (12.4 mL). The suspension was stirred and heated at 60° C. for 4 hours. Then an additional amount of 1-(3,5-dichlorophenyl)-2,2,2-trifluoro-ethanone (0.8575 g) was added to reaction mixture at 60° C. and stirring continued for another 2 hours. The reaction mixture was allowed to cool at 23° C. for 1 hour, then it was extracted twice between ethyl acetate and water. The combined organic layers were dried (Na2SO4), filtered, and evaporated under vacuo to give a crude residue. This crude product was suspended in TBME/cyclohexane (1:2) and stirred for 1 h and the solid formed was filtered. Thus, 16 g of 4-[3-(3,5-dichlorophenyl)-4,4,4-trifluoro-3-hydroxy-butanoyl]-N-(3-ethoxy-4,5-dihydroisoxazol-5-yl)-2-methyl-benzamide could be obtained. 1H-NMR (DMSO-d6, 400 MHz, δ in ppm): 1.29 (t, J=7.1 Hz, 3H), 2.41 (s, 3H), 2.81-2.89 (m, 1H), 3.40 (dd, J=16.8, 9.2 Hz, 1H), 3.85-3.94 (m, 1H), 4.12 (q, J=7.0 Hz, 2H), 4.44 (d, J=18.0 Hz, 1H), 6.21 (td, J=8.9, 4.1 Hz, 1H), 7.03 (s, 1H), 7.47 (d, J=7.9 Hz, 1H), 7.58 (s, 1H), 7.70 (s, 2H), 7.80 (d, J=7.9 Hz, 1H), 7.85 (s, 1H), 9.51 (d, J=8.7 Hz, 1H).

Preparation of N-(3-bromo-4,5-dihydroisoxazol-5-yl)-4-[3-(3,5-dichloro-4-fluoro-phenyl)-4,4,4-trifluoro-3-hydroxy-butanoyl]-N-formyl-2-methyl-benzamide and N-(3-bromo-4,5-dihydroisoxazol-5-yl)-4-[3-(3,5-dichloro-4-fluoro-phenyl)-4,4,4-trifluoro-3-hydroxy-butanoyl]-2-methyl-benzamide

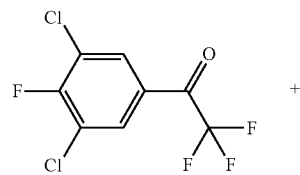

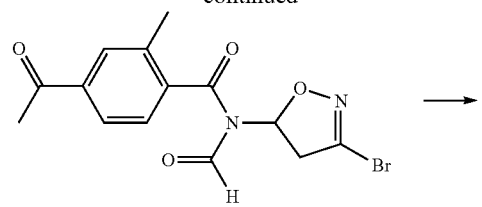

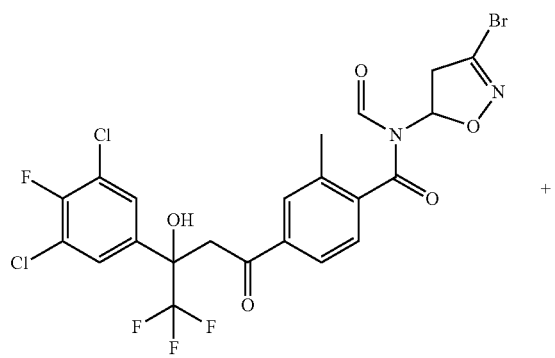

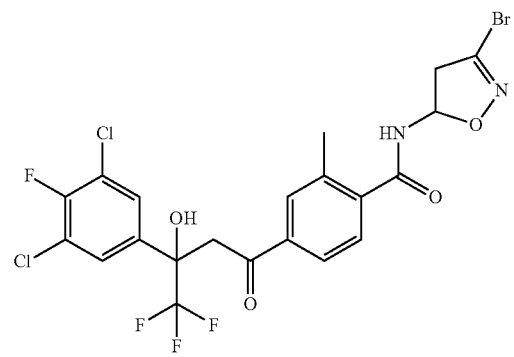

Using a similar procedure than the one just described, the following compounds could be prepared: N-(3-bromo-4,5-dihydroisoxazol-5-yl)-4-[3-(3,5-dichloro-4-fluoro-phenyl)-4,4,4-trifluoro-3-hydroxy-butanoyl]-N-formyl-2-methyl-benzamide: 1H-NMR (CDCl3, 400 MHz, □ in ppm): 2.46 (s, 3H) 3.44-3.63 (m, 2H) 3.67-3.77 (m, 1H) 3.77-3.89 (m, 1H) 5.48-5.58 (m, 1H) 6.80-6.92 (m, 1H) 7.49 (d, J=8.1 Hz, 1H) 7.53-7.60 (m, 2H) 7.80-7.93 (m, 2H) 8.64 (s, 1H) N-(3-bromo-4,5-dihydroisoxazol-5-yl)-4-[3-(3,5-dichloro-4-fluoro-phenyl)-4,4,4-trifluoro-3-hydroxy-butanoyl]-2-methyl-benzamide: 1H-NMR (CDCl3, 400 MHz, δ in ppm): 2.53 (s, 3H) 3.13 (dd, J=18.0, 4.0 Hz, 1H) 3.60-3.74 (m, 2H) 3.79-3.88 (m, 1H) 5.65 (s, 1H) 6.53 (dd, J=9.2, 4.0 Hz, 1H) 6.56-6.66 (m, 1H) 7.51 (d, J=8.4 Hz, 1H) 7.56 (d, J=6.2 Hz, 2H) 7.73-7.83 (m, 2H)

Preparation of 4-[(E)-3-(3,5-dichloro-4-fluoro-phenyl)-4,4,4-trifluoro-but-2-enoyl]-N-(3-methoxy-4,5-dihydroisoxazol-5-yl)-2-methyl-benzamide

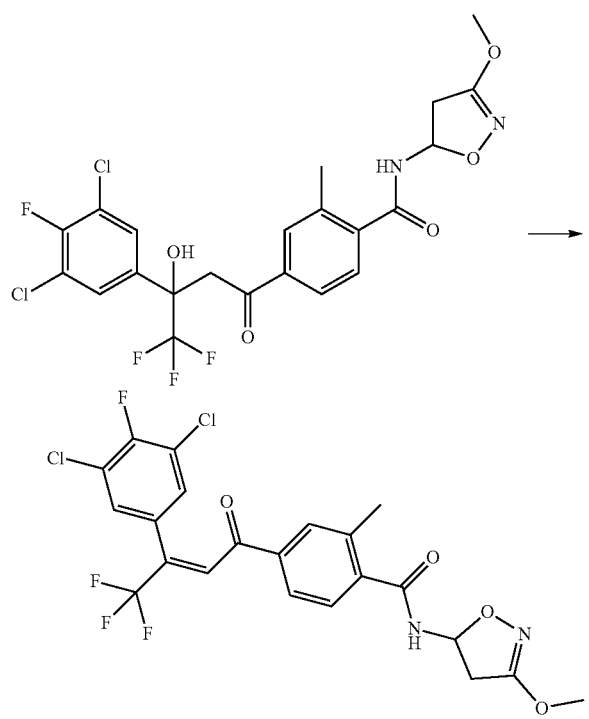

To a solution of 4-[3-(3,5-dichloro-4-fluoro-phenyl)-4,4,4-trifluoro-3-hydroxy-butanoyl]-N-(3-methoxy-4,5-dihydroisoxazol-5-yl)-2-methyl-benzamide (0.340 g) in Pyridine (1.27 mL) was added 4-(Dimethylamino)pyridine (7 mg) and acetic anhydride (0.11 mL) and the reaction was stirred at rt for 3.5 hours. The reaction mixture was extracted twice between ethyl acetate and a saturated solution of ammonium chloride. The combined organic layers were dried (MgSO$_4$), filtered, and evaporated under vacuo to give a crude residue. This crude product was suspended in 4 ml of diisopropylether. The suspension was filtered, the solid was washed with 2×1 ml of diisopropylether and 2×2 ml of pentane. The solid was dried under vacuo to give 269 mg of 4-[(E)-3-(3,5-dichloro-4-fluoro-phenyl)-4,4,4-trifluoro-but-2-enoyl]-N-(3-methoxy-4,5-dihydroisoxazol-5-yl)-2-methyl-benzamide. 1H-NMR (CDCl3, 400 MHz, δ in ppm): 2.50 (s, 3H) 2.85 (dd, J=17.2, 3.3 Hz, 1H) 3.39-3.56 (m, 1H) 3.90 (s, 3H) 6.34-6.48 (m, 1H) 6.48-6.60 (m, 1H) 7.24 (d, J=6.2 Hz, 2H) 7.40 (d, J=1.5 Hz, 1H) 7.48 (d, J=7.7 Hz, 1H) 7.62-7.74 (m, 2H).

In a similar type of reaction, 4-[(E)-3-(3,5-dichlorophenyl)-4,4,4-trifluoro-but-2-enoyl]-N-(3-ethoxy-4,5-dihydroisoxazol-5-yl)-2-methyl-benzamide was prepared: To a solution of 4-[3-(3,5-dichlorophenyl)-4,4,4-trifluoro-3-hydroxy-butanoyl]-N-(3-ethoxy-4,5-dihydroisoxazol-5-yl)-2-methyl-benzamide (7.5 g) in 1,4-dioxane (38 mL) was added N,N-diethylethanamine (4.6 mL), 4-(Dimethylamino)pyridine (0.17 g) and acetic anhydride (2.3 mL). The reaction was stirred at 25° C. for 3.5 hours. The reaction mass was charged into cold water (150 ml, 10° C.), and the resulting precipitate was filtered out and dried to give a crude solid (6.86 g). This crude material was suspended into Ethanol/Water (5:1) and heated at 78° C. for 1 hour. The resulting suspension was cooled down to 23° C., filtered and dried to give 6.0 g of 4-[(E)-3-(3,5-dichlorophenyl)-4,4,4-trifluoro-but-2-enoyl]-N-(3-ethoxy-4,5-dihydroisoxazol-5-yl)-2-methyl-benzamide. 1H-NMR (DMSO-d6, 400 MHz, δ in ppm): 1.28 (t, J=7.0 Hz, 3H), 2.40 (s, 3H), 2.80-2.86 (m, 1H), 3.40 (dd, J=16.8, 9.3 Hz, 1H), 4.12 (q, J=7.0 Hz, 2H), 6.20 (td, J=8.9, 4.0 Hz, 1H), 7.37 (s, 2H), 7.48 (d, J=7.8 Hz, 1H), 7.68 (s, 1H), 7.76-7.84 (m, 2H), 7.90 (s, 1H), 9.55 (d, J=8.8 Hz, 1H).

Preparation of N-(3-bromo-4,5-dihydroisoxazol-5-yl)-4-[(E)-3-(3,5-dichloro-4-fluoro-phenyl)-4,4,4-trifluoro-but-2-enoyl]-2-methyl-benzamide and N-(3-bromo-4,5-dihydroisoxazol-5-yl)-4-[(E)-3-(3,5-dichloro-4-fluoro-phenyl)-4,4,4-trifluoro-but-2-enoyl]-N-formyl-2-methyl-benzamide

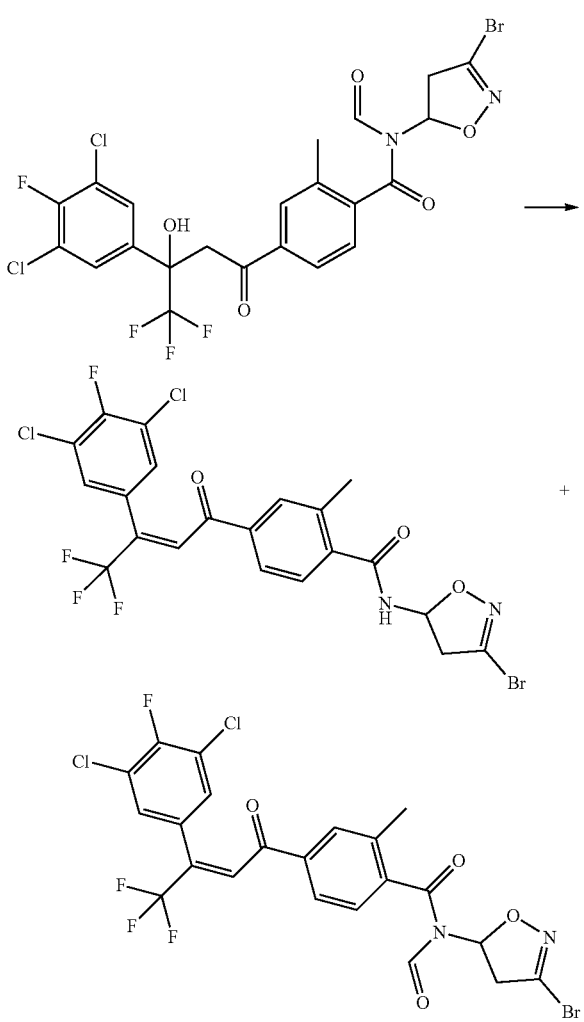

Using a similar procedure than the one just described, the following compounds could be prepared: N-(3-bromo-4,5-dihydroisoxazol-5-yl)-4-[(E)-3-(3,5-dichloro-4-fluoro-phenyl)-4,4,4-trifluoro-but-2-enoyl]-N-formyl-2-methyl-benzamide: 1H-NMR (CDCl3, 400 MHz, δ in ppm): 2.42 (s, 3H) 3.42-3.66 (m, 2H) 6.85 (dd, J=10.6, 5.5 Hz, 1H) 7.25 (d, J=6.2 Hz, 2H) 7.23-7.27 (m, 2H) 7.39-7.47 (m, 2H) 7.73-7.81 (m, 2H) 8.60 (s, 1H)

N-(3-bromo-4,5-dihydroisoxazol-5-yl)-4-[(E)-3-(3,5-dichloro-4-fluoro-phenyl)-4,4,4-trifluoro-but-2-enoyl]-2-methyl-benzamide: 1H-NMR (CDCl3, 400 MHz, δ in ppm): 2.50 (s, 3H) 3.06-3.20 (m, 1H) 3.60-3.76 (m, 1H) 6.52 (m, 2H) 7.23 (s, 1H) 7.25 (s, 1H) 7.40 (m, 1H) 7.47 (d, J=7.7 Hz, 1H) 7.64-7.73 (m, 2H)

Preparation of 4-[(5S)-5-(3,5-dichloro-4-fluoro-phenyl)-5-(trifluoromethyl)-4H-isoxazol-3-yl]-N-(3-methoxy-4,5-dihydroisoxazol-5-yl)-2-methyl-benzamide

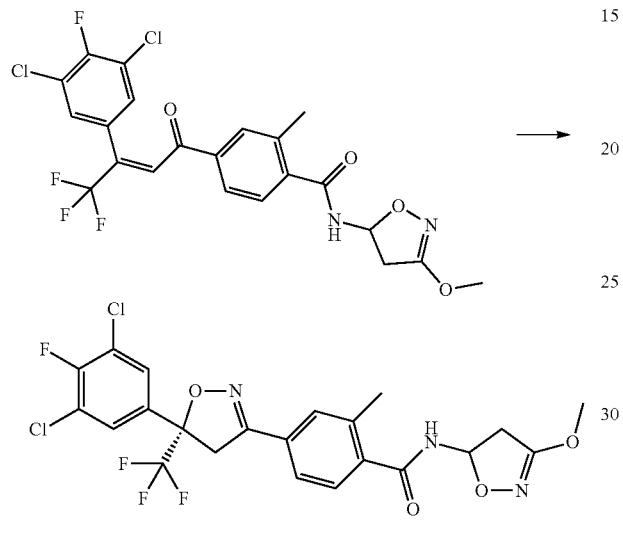

To a suspension of 4-[(E)-3-(3,5-dichloro-4-fluoro-phenyl)-4,4,4-trifluoro-but-2-enoyl]-N-(3-methoxy-4,5-dihydroisoxazol-5-yl)-2-methyl-benzamide (0.10 g) in 1,2-dichloroethane (0.96 mL) was added 2,3,4,5,6-pentafluorophenyl-methyl quininium bromide (0.011 g). The reaction mixture was cooled to −20° C., then hydroxylamine (50% aq., 0.026 mL) was added, followed by a solution of sodium hydroxide (2N, 0.015 mL). The reaction mixture was stirred at −20° C. for 24 h then a saturated solution of ammonium chloride was added. The mixture was extracted twice between ethyl acetate and water. The combined organic layers were dried (MgSO4), filtered, and evaporated under vacuo to give a crude residue. This crude product was absorbed on isolute and purified by chromatography with 0-100% EtOAc/Cyclohexane (using the Rf Combiflash apparatus) to give 73 mg of 4-[(5S)-5-(3,5-dichloro-4-fluoro-phenyl)-5-(trifluoromethyl)-4H-isoxazol-3-yl]-N-(3-methoxy-4,5-dihydroisoxazol-5-yl)-2-methyl-benzamide.
1H-NMR (CDCl3, 400 MHz, δ in ppm): 2.50 (s, 3H) 2.86 (dd, J=17.2, 3.7 Hz, 1H) 3.47 (dd, J=17.2, 8.8 Hz, 1H) 3.69 (d, J=17.2 Hz, 1H) 3.90 (s, 3H) 4.03-4.13 (m, 1H) 6.44 (td, J=8.6, 3.7 Hz, 1H) 6.54 (d, J=8.4 Hz, 1H) 7.40-7.48 (m, 1H) 7.52 (d, J=6.2 Hz, 2H) 7.59 (d, J=6.2 Hz, 2H)

Preparation of N-(3-bromo-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide

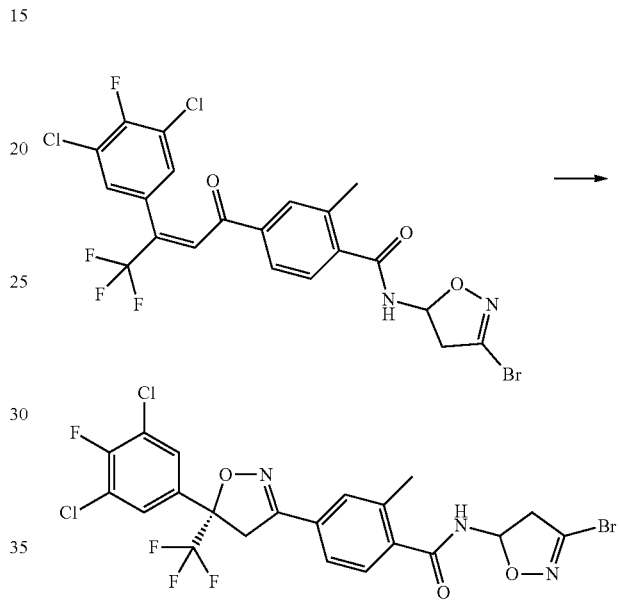

Using a similar procedure than the one just described, the following compound could be prepared: N-(3-bromo-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide: 1H-NMR (CDCl3, 400 MHz, δ in ppm): 2.47 (s, 3H) 3.13 (ddd, J=18.1, 4.1, 2.7 Hz, 1H) 3.58-3.77 (m, 2H) 4.09 (d, J=17.2 Hz, 1H) 6.50 (td, J=9.1, 3.8 Hz, 1H) 6.62-6.78 (m, 1H) 7.33-7.46 (m, 1H) 7.46-7.53 (m, 2H) 7.59 (d, J=6.2 Hz, 2H)

TABLE A

Compounds according to the invention

| Cpd No | chemical name | LC-MS Method | RT (min) | [M − H]⁻ | [M + H]⁺ |
|---|---|---|---|---|---|
| A001 | N-(3-bromo-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide | B | 1.18 | 580/582/584 | |
| A002 | N-(3-bromo-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide | B | 1.24 | 580/582/584 (M-CHO) | |
| A003 | N-(3-chloro-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide | B | 1.18 | 536/538/540 | |

TABLE A-continued

Compounds according to the invention

| Cpd No | chemical name | LC-MS Method | RT (min) | [M − H]⁻ | [M + H]⁺ |
|---|---|---|---|---|---|
| A004 | 4-[(5S)-5-(3,5-dichloro-4-fluoro-phenyl)-5-(trifluoromethyl)-4H-isoxazol-3-yl]-N-formyl-2-methyl-N-[3-(trifluoromethyl)-4,5-dihydroisoxazol-5-yl]benzamide | B | 1.26 | 570/572 (M-CHO) | |
| A005 | 4-[(5S)-5-(3,5-dichloro-4-fluoro-phenyl)-5-(trifluoromethyl)-4H-isoxazol-3-yl]-2-methyl-N-[3-(trifluoromethyl)-4,5-dihydroisoxazol-5-yl]benzamide | B | 1.22 | 570/572 | |
| A006 | ethyl 5-[[4-[(5S)-5-(3,5-dichloro-4-fluoro-phenyl)-5-(trifluoromethyl)-4H-isoxazol-3-yl]-2-methyl-benzoyl]-formyl-amino]-4,5-dihydroisoxazole-3-carboxylate | B | 1.23 | 574/576 (M-CHO) | |
| A007 | ethyl 5-[[4-[(5S)-5-(3,5-dichloro-4-fluoro-phenyl)-5-(trifluoromethyl)-4H-isoxazol-3-yl]-2-methyl-benzoyl]amino]-4,5-dihydroisoxazole-3-carboxylate | B | 1.18 | 574/576 | |
| A008 | 4-[(5S)-5-(3,5-dichloro-4-fluoro-phenyl)-5-(trifluoromethyl)-4H-isoxazol-3-yl]-N-formyl-2-methyl-N-(3-methyl-4,5-dihydroisoxazol-5-yl)benzamide | B | 1.19 | 544/546 | |
| A009 | 4-[(5S)-5-(3,5-dichloro-4-fluoro-phenyl)-5-(trifluoromethyl)-4H-isoxazol-3-yl]-2-methyl-N-(3-methyl-4,5-dihydroisoxazol-5-yl)benzamide | B | 1.13 | 516/518 | |
| A010 | N-(3-chloro-4,5-dihydroisoxazol-5-yl)-N-formyl-2-methyl-4-[(5S)-5-(3,4,5-trichlorophenyl)-5-(trifluoromethyl)-4H-isoxazol-3-yl]benzamide | B | 1.27 | 552/554/556 (M-CHO) | |
| A011 | N-(3-chloro-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide | B | 1.23 | 536/538/540 (M-CHO) | |
| A012 | N-(3-chloro-4,5-dihydroisoxazol-5-yl)-4-[(5S)-5-[3-chloro-5-(trifluoromethyl)phenyl]-5-(trifluoromethyl)-4H-isoxazol-3-yl]-N-formyl-2-methyl-benzamide | B | 1.23 | 552/554 (M-CHO) | |
| A013 | N-(3-chloro-4,5-dihydroisoxazol-5-yl)-2-methyl-4-[(5S)-5-(3,4,5-trichlorophenyl)-5-(trifluoromethyl)-4H-isoxazol-3-yl]benzamide | B | 1.22 | 552/554/556 | |
| A014 | N-(3-acetyl-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide | B | 1.22 | 572/574 | |
| A015 | N-(3-acetyl-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide | B | 1.17 | 544/546 | |
| A016 | N-(3-chloro-4,5-dihydroisoxazol-5-yl)-4-[(5S)-5-[3-chloro-5-(trifluoromethyl)phenyl]-5-(trifluoromethyl)-4H-isoxazol-3-yl]-2-methyl-benzamide | B | 1.18 | 552/554 | |
| A017 | 2-chloro-N-(3-chloro-4,5-dihydroisoxazol-5-yl)-N-formyl-4-[(5S)-5-(3,4,5-trichlorophenyl)-5-(trifluoromethyl)-4H-isoxazol-3-yl]benzamide | B | 1.28 | 600/602/604 | |
| A018 | 2-chloro-N-(3-chloro-4,5-dihydroisoxazol-5-yl)-4-[(5S)-5-(3,4,5-trichlorophenyl)-5-(trifluoromethyl)-4H-isoxazol-3-yl]benzamide | B | 1.22 | 572/574/576 | |
| A019 | 4-[(5S)-5-[3-bromo-5-(trifluoromethyl)phenyl]-5-(trifluoromethyl)-4H-isoxazol-3-yl]-N-(3-chloro-4,5-dihydroisoxazol-5-yl)-N-formyl-2-methyl-benzamide | B | 1.24 | 624/626/628 | |
| A020 | 4-[(5S)-5-(3,5-dichloro-4-methylsulfanyl-phenyl)-5-(trifluoromethyl)-4H-isoxazol-3-yl]-2-methyl-N-(3-methylsulfanyl-4,5-dihydroisoxazol-5-yl)benzamide | B | 1.19 | 576/578/580 | |
| A021 | 4-[(5S)-5-[3-bromo-5-(trifluoromethyl)phenyl]-5-(trifluoromethyl)-4H-isoxazol-3-yl]-N-(3-chloro-4,5-dihydroisoxazol-5-yl)-2-methyl-benzamide | B | 1.19 | 596/598/600 | |
| A022 | 4-[(5S)-5-(3,5-dichloro-4-fluoro-phenyl)-5-(trifluoromethyl)-4H-isoxazol-3-yl]-N-(3-ethyl-4,5-dihydroisoxazol-5-yl)-N-formyl-2-methyl-benzamide | B | 1.23 | 558/560/562 | |
| A023 | N-formyl-2-methyl-N-(3-methyl-4,5-dihydroisoxazol-5-yl)-4-[(5S)-5-(3,4,5-trichlorophenyl)-5-(trifluoromethyl)-4H-isoxazol-3-yl]benzamide | B | 1.23 | 560/562/564 | |

TABLE A-continued

Compounds according to the invention

| Cpd No | chemical name | LC-MS Method | RT (min) | [M − H]⁻ | [M + H]⁺ |
|---|---|---|---|---|---|
| A024 | 2-chloro-N-formyl-N-(3-methyl-4,5-dihydroisoxazol-5-yl)-4-[(5S)-5-(3,4,5-trichlorophenyl)-5-(trifluoromethyl)-4H-isoxazol-3-yl]benzamide | B | 1.24 | 580/582/584 | |
| A025 | 2-chloro-N-(3-methyl-4,5-dihydroisoxazol-5-yl)-4-[(5S)-5-(3,4,5-trichlorophenyl)-5-(trifluoromethyl)-4H-isoxazol-3-yl]benzamide | B | 1.18 | 552/554/556 | |
| A026 | 4-[(5S)-5-(3,5-dichloro-4-fluoro-phenyl)-5-(trifluoromethyl)-4H-isoxazol-3-yl]-N-(3-ethyl-4,5-dihydroisoxazol-5-yl)-2-methyl-benzamide | B | 1.16 | 530/532/534 | |
| A027 | 2-methyl-N-(3-methyl-4,5-dihydroisoxazol-5-yl)-4-[(5S)-5-(3,4,5-trichlorophenyl)-5-(trifluoromethyl)-4H-isoxazol-3-yl]benzamide | B | 1.17 | 532/534/536 | |
| A028 | 4-[(5S)-5-[3-chloro-5-(trifluoromethyl)phenyl]-5-(trifluoromethyl)-4H-isoxazol-3-yl]-2-methyl-N-(3-methyl-4,5-dihydroisoxazol-5-yl)benzamide | B | 1.13 | 532/534 | |
| A029 | 4-[(5S)-5-[3-bromo-5-(trifluoromethyl)phenyl]-5-(trifluoromethyl)-4H-isoxazol-3-yl]-2-methyl-N-(3-methyl-4,5-dihydroisoxazol-5-yl)benzamide | B | 1.14 | 576/578 | |
| A030 | 4-[(5S)-5-(3,5-dichloro-4-fluoro-phenyl)-5-(trifluoromethyl)-4H-isoxazol-3-yl]-N-(3-methoxy-4,5-dihydroisoxazol-5-yl)-2-methyl-benzamide | B | 1.14 | 532/534/536 | |
| A031 | N-(3-cyclopropyl-4,5-dihydroisoxazol-5-yl)-4-[(5S)-5-(3,5-dichloro-4-fluoro-phenyl)-5-(trifluoromethyl)-4H-isoxazol-3-yl]-N-formyl-2-methyl-benzamide | B | 1.22 | 570/572/574 | |
| A032 | N-(3-cyclopropyl-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide | B | 1.16 | 542/544/546 | |
| A033 | 2-chloro-4-[(5S)-5-(3,5-dichloro-4-fluoro-phenyl)-5-(trifluoromethyl)-4H-isoxazol-3-yl]-N-formyl-N-(3-methyl-4,5-dihydroisoxazol-5-yl)benzamide | B | 1.2 | 564/566/568 | |
| A034 | 2-bromo-4-[(5S)-5-(3,5-dichloro-4-fluoro-phenyl)-5-(trifluoromethyl)-4H-isoxazol-3-yl]-N-formyl-N-(3-methyl-4,5-dihydroisoxazol-5-yl)benzamide | B | 1.21 | 608/610/612 | |
| A035 | 2-bromo-N-formyl-N-(3-methyl-4,5-dihydroisoxazol-5-yl)-4-[(5S)-5-(3,4,5-trichlorophenyl)-5-(trifluoromethyl)-4H-isoxazol-3-yl]benzamide | B | 1.25 | 624/626/628 | |
| A036 | 2-bromo-4-[(5S)-5-(3,5-dichloro-4-fluoro-phenyl)-5-(trifluoromethyl)-4H-isoxazol-3-yl]-N-(3-methyl-4,5-dihydroisoxazol-5-yl)benzamide | B | 1.14 | 580/582/584 | |
| A037 | 2-bromo-N-(3-methyl-4,5-dihydroisoxazol-5-yl)-4-[(5S)-5-(3,4,5-trichlorophenyl)-5-(trifluoromethyl)-4H-isoxazol-3-yl]benzamide | B | 1.18 | 596/598/600 | |
| A038 | 2-chloro-4-[(5S)-5-(3,5-dichloro-4-fluoro-phenyl)-5-(trifluoromethyl)-4H-isoxazol-3-yl]-N-(3-methyl-4,5-dihydroisoxazol-5-yl)benzamide | B | 1.14 | 536/538/540 | |
| A039 | 4-[(5S)-5-[3-chloro-5-(trifluoromethyl)phenyl]-5-(trifluoromethyl)-4H-isoxazol-3-yl]-N-formyl-2-methyl-N-(3-methyl-4,5-dihydroisoxazol-5-yl)benzamide | * | * | * | * |
| A040 | 4-[(5S)-5-[3-bromo-5-(trifluoromethyl)phenyl]-5-(trifluoromethyl)-4H-isoxazol-3-yl]-N-formyl-2-methyl-N-(3-methyl-4,5-dihydroisoxazol-5-yl)benzamide | * | * | * | * |
| A041 | N-(3-methoxy-4,5-dihydroisoxazol-5-yl)-2-methyl-4-[(5S)-5-(3,4,5-trichlorophenyl)-5-(trifluoromethyl)-4H-isoxazol-3-yl]benzamide | B | 1.16 | 548/550/552 | |
| A042 | 4-[(5S)-5-[3-chloro-5-(trifluoromethyl)phenyl]-5-(trifluoromethyl)-4H-isoxazol-3-yl]-N-(3-methoxy-4,5-dihydroisoxazol-5-yl)-2-methyl-benzamide | B | 1.14 | 548/550 | |
| A043 | 2-chloro-N-(3-methoxy-4,5-dihydroisoxazol-5-yl)-4-[(5S)-5-(3,4,5-trichlorophenyl)-5-(trifluoromethyl)-4H-isoxazol-3-yl]benzamide | B | 1.19 | 568/570/572 | |
| A044 | 4-[(5S)-5-[3-bromo-5-(trifluoromethyl)phenyl]-5-(trifluoromethyl)-4H-isoxazol-3-yl]-N-(3-methoxy-4,5-dihydroisoxazol-5-yl)-2-methyl-benzamide | B | 1.15 | 592/594 | |

TABLE A-continued

Compounds according to the invention

| Cpd No | chemical name | LC-MS Method | RT (min) | [M − H]⁻ | [M + H]⁺ |
|---|---|---|---|---|---|
| A045 | 2-chloro-4-[(5S)-5-(3,5-dichloro-4-fluoro-phenyl)-5-(trifluoromethyl)-4H-isoxazol-3-yl]-N-(3-methoxy-4,5-dihydroisoxazol-5-yl)benzamide | B | 1.14 | 552/554/556 | |
| A046 | 4-[(5S)-5-(3,5-dichloro-4-fluoro-phenyl)-5-(trifluoromethyl)-4H-isoxazol-3-yl]-N-(3-ethoxy-4,5-dihydroisoxazol-5-yl)-2-methyl-benzamide | B | 1.17 | 546/548 | |
| A047 | 4-[(5S)-5-[3-chloro-5-(trifluoromethyl)phenyl]-5-(trifluoromethyl)-4H-isoxazol-3-yl]-N-(3-ethoxy-4,5-dihydroisoxazol-5-yl)-2-methyl-benzamide | B | 1.17 | 562 | |
| A048 | 4-[(5S)-5-(3,5-dichloro-4-methylsulfanyl-phenyl)-5-(trifluoromethyl)-4H-isoxazol-3-yl]-2-methyl-N-(3-methylsulfanyl-4,5-dihydroisoxazol-5-yl)benzamide | B | 1.21 | 564/566 | |
| A049 | 2-methyl-N-(3-methylsulfanyl-4,5-dihydroisoxazol-5-yl)-4-[(5S)-5-(3,4,5-trichlorophenyl)-5-(trifluoromethyl)-4H-isoxazol-3-yl]benzamide | B | 1.2 | 576/578 | |
| A050 | 4-[(5S)-5-[3-chloro-5-(trifluoromethyl)phenyl]-5-(trifluoromethyl)-4H-isoxazol-3-yl]-2-methyl-N-(3-methylsulfanyl-4,5-dihydroisoxazol-5-yl)benzamide | B | 1.17 | 564/566 | |
| A051 | 4-[(5S)-5-[3-chloro-5-(trifluoromethyl)phenyl]-5-(trifluoromethyl)-4H-isoxazol-3-yl]-N-(3-ethylsulfanyl-4,5-dihydroisoxazol-5-yl)-2-methyl-benzamide | B | 1.2 | 578/580 | |
| A052 | N-(3-ethylsulfanyl-4,5-dihydroisoxazol-5-yl)-2-methyl-4-[(5S)-5-(3,4,5-trichlorophenyl)-5-(trifluoromethyl)-4H-isoxazol-3-yl]benzamide | B | 1.24 | 578/580/582 | |
| A053 | N-(3-ethylsulfonyl-4,5-dihydroisoxazol-5-yl)-2-methyl-4-[(5S)-5-(3,4,5-trichlorophenyl)-5-(trifluoromethyl)-4H-isoxazol-3-yl]benzamide | B | 1.2 | 610/612/614 | |
| A054 | 4-[(5S)-5-(3,5-dichlorophenyl)-5-(trifluoromethyl)-4H-isoxazol-3-yl]-N-(3-methoxy-4,5-dihydroisoxazol-5-yl)-2-methyl-benzamide | B | 1.13 | 514/516 | |
| A055 | N-(3-bromo-4,5-dihydroisoxazol-5-yl)-4-[(5S)-5-(3,5-dichlorophenyl)-5-(trifluoromethyl)-4H-isoxazol-3-yl]-2-methyl-benzamide | B | 1.17 | 562/564/566 | |
| A056 | N-(3-bromo-4,5-dihydroisoxazol-5-yl)-4-[(5S)-5-(3,5-dichlorophenyl)-5-(trifluoromethyl)-4H-isoxazol-3-yl]-N-formyl-2-methyl-benzamide | B | 1.23 | 562/564/566 (M-CHO) | |
| A057 | N-(3-methoxy-4,5-dihydroisoxazol-5-yl)-2-methyl-4-[(5S)-5-(trifluoromethyl)-5-[3-(trifluoromethyl)phenyl]-4H-isoxazol-3-yl]benzamide | B | 1.06 | 514 | |
| A058 | N-(3-bromo-4,5-dihydroisoxazol-5-yl)-2-methyl-4-[(5S)-5-(trifluoromethyl)-5-[3-(trifluoromethyl)phenyl]-4H-isoxazol-3-yl]benzamide | B | 1.11 | 562/564 | |
| A059 | N-(3-ethoxy-4,5-dihydroisoxazol-5-yl)-2-methyl-4-[(5S)-5-(3,4,5-trichlorophenyl)-5-(trifluoromethyl)-4H-isoxazol-3-yl]benzamide | B | 1.21 | 562/564/566 | |
| A060 | 2-chloro-N-(3-ethoxy-4,5-dihydroisoxazol-5-yl)-4-[(5S)-5-(3,4,5-trichlorophenyl)-5-(trifluoromethyl)-4H-isoxazol-3-yl]benzamide | A | 1.24 | | 584/586/588/590 |
| A061 | 4-[(5S)-5-(3,5-dichlorophenyl)-5-(trifluoromethyl)-4H-isoxazol-3-yl]-N-(3-ethoxy-4,5-dihydroisoxazol-5-yl)-2-methyl-benzamide | C | 1.99 | | 530/532/534 |
| A062 | 2-chloro-4-[(5S)-5-(3,5-dichlorophenyl)-5-(trifluoromethyl)-4H-isoxazol-3-yl]-N-(3-methoxy-4,5-dihydroisoxazol-5-yl)benzamide | A | 1.14 | 534/536/538 | |
| A063 | 2-chloro-4-[(5S)-5-(3,5-dichlorophenyl)-5-(trifluoromethyl)-4H-isoxazol-3-yl]-N-(3-ethoxy-4,5-dihydroisoxazol-5-yl)benzamide | A | 1.18 | 548/550/552 | |
| A064 | 2-chloro-4-[(5S)-5-(3,5-dichloro-4-fluoro-phenyl)-5-(trifluoromethyl)-4H-isoxazol-3-yl]-N-(3-ethoxy-4,5-dihydroisoxazol-5-yl)benzamide | B | 1.16 | 566/568/570 | |
| A065 | 2-chloro-4-[(5S)-5-[3-chloro-5-(trifluoromethyl)phenyl]-5-(trifluoromethyl)-4H-isoxazol-3-yl]-N-(3-methoxy-4,5-dihydroisoxazol-5-yl)benzamide | B | 1.14 | 568/570/572 | |

TABLE A-continued

Compounds according to the invention

| Cpd No | chemical name | LC-MS Method | RT (min) | [M − H]⁻ | [M + H]⁺ |
|---|---|---|---|---|---|
| A066 | 2-chloro-4-[(5S)-5-[3-chloro-5-(trifluoromethyl)phenyl]-5-(trifluoromethyl)-4H-isoxazol-3-yl]-N-(3-ethoxy-4,5-dihydroisoxazol-5-yl)benzamide | B | 1.17 | 582/584/586 | |
| A067 | tert-butyl N-(3-chloro-4,5-dihydroisoxazol-5-yl)-N-[4-[(5S)-5-(3,5-dichloro-4-fluoro-phenyl)-5-(trifluoromethyl)-4H-isoxazol-3-yl]-2-methyl-benzoyl]carbamate | * | * | * | * |
| A068 | tert-butyl N-[4-[(5S)-5-(3,5-dichloro-4-fluoro-phenyl)-5-(trifluoromethyl)-4H-isoxazol-3-yl]-2-methyl-benzoyl]-N-[3-(tetrahydropyran-2-yloxymethyl)-4,5-dihydroisoxazol-5-yl]carbamate | A | 1.36 | | 718/720 |
| A069 | [5-[[4-[(5S)-5-(3,5-dichloro-4-fluoro-phenyl)-5-(trifluoromethyl)-4H-isoxazol-3-yl]-2-methyl-benzoyl]amino]-4,5-dihydroisoxazol-3-yl]methyl acetate | A | 1.15 | | 576/578 |
| A070 | 4-[(5S)-5-(3,5-dichloro-4-fluoro-phenyl)-5-(trifluoromethyl)-4H-isoxazol-3-yl]-2-methyl-N-(3-propoxy-4,5-dihydroisoxazol-5-yl)benzamide | A | 1.22 | | 562/564 |
| A071 | 4-[(5S)-5-(3,5-dichloro-4-fluoro-phenyl)-5-(trifluoromethyl)-4H-isoxazol-3-yl]-N-[3-(2,2-difluoroethoxy)-4,5-dihydroisoxazol-5-yl]-2-methyl-benzamide | A | 1.18 | | 584/586 |
| A072 | N-(3-allyloxy-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide | A | 1.2 | | 560/562 |
| A073 | 4-[(5S)-5-(3,5-dichloro-4-fluoro-phenyl)-5-(trifluoromethyl)-4H-isoxazol-3-yl]-N-(3-isobutoxy-4,5-dihydroisoxazol-5-yl)-2-methyl-benzamide | A | 1.25 | | 576/578 |
| A074 | 4-[(5S)-5-(3,5-dichloro-4-fluoro-phenyl)-5-(trifluoromethyl)-4H-isoxazol-3-yl]-2-methyl-N-(3-prop-2-ynoxy-4,5-dihydroisoxazol-5-yl)benzamide | A | 1.18 | | 558/560 |
| A075 | 4-[(5S)-5-(3,5-dichloro-4-fluoro-phenyl)-5-(trifluoromethyl)-4H-isoxazol-3-yl]-N-[3-(2,2,3,4,4,4-hexafluorobutoxy)-4,5-dihydroisoxazol-5-yl]-2-methyl-benzamide | A | 1.25 | | 684/686 |
| A076 | 4-[(5S)-5-(3,5-dichloro-4-fluoro-phenyl)-5-(trifluoromethyl)-4H-isoxazol-3-yl]-N-[3-(2-methoxyethoxy)-4,5-dihydroisoxazol-5-yl]-2-methyl-benzamide | A | 1.16 | | 578/580 |
| A077 | 4-[(5S)-5-(3,5-dichloro-4-fluoro-phenyl)-5-(trifluoromethyl)-4H-isoxazol-3-yl]-N-(3-isopropoxy-4,5-dihydroisoxazol-5-yl)-2-methyl-benzamide | A | 1.25 | | 562/564 |
| A078 | N-[3-(cyclopropoxy)-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide | C | 2.02 | | 560/562 |
| A079 | N-[3-(cyclobutoxy)-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide | C | 2.11 | | 574/576 |
| A080 | 4-[(5S)-5-(3,5-dichloro-4-fluoro-phenyl)-5-(trifluoromethyl)-4H-isoxazol-3-yl]-2-methyl-N-[3-(2-methylallyloxy)-4,5-dihydroisoxazol-5-yl]benzamide | C | 2.12 | | 574/576 |
| A081 | 4-[(5S)-5-(3,5-dichloro-4-fluoro-phenyl)-5-(trifluoromethyl)-4H-isoxazol-3-yl]-N-[3-(2-fluoroallyloxy)-4,5-dihydroisoxazol-5-yl]-2-methyl-benzamide | C | 2.06 | | 578/580 |
| A082 | 4-[(5S)-5-(3,5-dichloro-4-fluoro-phenyl)-5-(trifluoromethyl)-4H-isoxazol-3-yl]-2-methyl-N-[3-(oxetan-3-yloxy)-4,5-dihydroisoxazol-5-yl]benzamide | C | 1.91 | | 576/578 |
| A083 | N-[3-(cyclopropylmethoxy)-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide | C | 2.08 | | 574/576 |

TABLE A-continued

Compounds according to the invention

| Cpd No | chemical name | LC-MS Method | RT (min) | [M − H]⁻ | [M + H]⁺ |
|---|---|---|---|---|---|
| A084 | 4-[(5S)-5-(3,5-dichloro-4-fluoro-phenyl)-5-(trifluoromethyl)-4H-isoxazol-3-yl]-2-methyl-N-[3-[(E)-4,4,4-trifluorobut-2-enoxy]-4,5-dihydroisoxazol-5-yl]benzamide | C | 2.15 | | 628/630 |
| A085 | 4-[(5S)-5-(3,5-dichloro-4-fluoro-phenyl)-5-(trifluoromethyl)-4H-isoxazol-3-yl]-2-methyl-N-[3-(3-methylbut-2-enoxy)-4,5-dihydroisoxazol-5-yl]benzamide | C | 2.17 | | 588/590 |
| A086 | tert-butyl N-[4-[(5S)-5-(3,5-dichloro-4-fluoro-phenyl)-5-(trifluoromethyl)-4H-isoxazol-3-yl]-2-methyl-benzoyl]-N-(4,5-dihydroisoxazol-5-yl)carbamate | A | 1.29 | | 504/506 (M-Boc) |
| A087 | 4-[(5S)-5-(3,5-dichloro-4-fluoro-phenyl)-5-(trifluoromethyl)-4H-isoxazol-3-yl]-N-[3-(hydroxymethyl)-4,5-dihydroisoxazol-5-yl]-2-methyl-benzamide | A | 1.08 | | 534/536/538 |
| A088 | tert-butyl N-[4-[(5S)-5-(3,5-dichloro-4-fluoro-phenyl)-5-(trifluoromethyl)-4H-isoxazol-3-yl]-2-methyl-benzoyl]-N-[3-(methoxymethyl)-4,5-dihydroisoxazol-5-yl]carbamate | A | 1.3 | | 648/650 |
| A089 | [5-[[4-[(5S)-5-(3,5-dichloro-4-fluoro-phenyl)-5-(trifluoromethyl)-4H-isoxazol-3-yl]-2-methyl-benzoyl]amino]-4,5-dihydroisoxazol-3-yl]methyl formate | A | 1.14 | | 562/564 |
| A090 | 4-[(5S)-5-(3,5-dichloro-4-fluoro-phenyl)-5-(trifluoromethyl)-4H-isoxazol-3-yl]-N-[3-(methoxymethyl)-4,5-dihydroisoxazol-5-yl]-2-methyl-benzamide | A | 1.14 | | 548/550 |
| A091 | 4-[(5S)-5-(3,5-dichloro-4-fluoro-phenyl)-5-(trifluoromethyl)-4H-isoxazol-3-yl]-N-(4,5-dihydroisoxazol-5-yl)-2-methyl-benzamide | A | 1.12 | | 504/506 |
| A092 | tert-butyl N-[4-[(5S)-5-(3,5-dichloro-4-fluoro-phenyl)-5-(trifluoromethyl)-4H-isoxazol-3-yl]-2-methyl-benzoyl]-N-(3-methoxy-4,5-dihydroisoxazol-5-yl)carbamate | A | 1.34 | 648/650/652 | |
| A093 | N-(3-bromo-4,5-dihydroisoxazol-5-yl)-2-chloro-4-[(5S)-5-(3,5-dichlorophenyl)-5-(trifluoromethyl)-4H-isoxazol-3-yl]benzamide | A | 1.19 | 582/584/586 | |
| A094 | N-[3-bromo-4,5-dihydroisoxazol-5-yl]-4-[(5S)-5-(3,5-dichloro-4-fluoro-phenyl)-5-(trifluoromethyl)-4H-isoxazol-3-yl]-2-methyl-N-[(1S)-1-phenylethyl]benzamide (most apolar isomer) | B | 1.31 | 537/839/541 (M-C3H4BrNO) | |
| A095 | N-[3-bromo-4,5-dihydroisoxazol-5-yl]-4-[(5S)-5-(3,5-dichloro-4-fluoro-phenyl)-5-(trifluoromethyl)-4H-isoxazol-3-yl]-2-methyl-N-[(1S)-1-phenylethyl]benzamide (less apolar isomer) | B | 1.3 | 537/839/541 (M-C3H4BrNO) | |
| A096 | N-[3-bromo-4,5-dihydroisoxazol-5-yl]-4-[(5S)-5-(3,5-dichloro-4-fluoro-phenyl)-5-(trifluoromethyl)-4H-isoxazol-3-yl]-N-[(1S)-1-(4-methoxyphenyl)ethyl]-2-methyl-benzamide (most apolar isomer) | B | 1.31 | 567/569/571 (M-C3H4BrNO) | |
| A097 | N-[3-bromo-4,5-dihydroisoxazol-5-yl]-4-[(5S)-5-(3,5-dichloro-4-fluoro-phenyl)-5-(trifluoromethyl)-4H-isoxazol-3-yl]-N-[(1S)-1-(4-methoxyphenyl)ethyl]-2-methyl-benzamide (less apolar isomer) | B | 1.3 | 567/569/571 (M-C3H4BrNO) | |
| A098 | tert-butyl N-[4-[(5S)-5-(3,5-dichloro-4-fluoro-phenyl)-5-(trifluoromethyl)-4H-isoxazol-3-yl]-2-methyl-benzoyl]-N-[3-(diethoxymethyl)-4,5-dihydroisoxazol-5-yl]carbamate (less apolar isomer) | A | 1.37 | | 706/708 |
| A099 | 4-[(5S)-5-(3,5-dichloro-4-fluoro-phenyl)-5-(trifluoromethyl)-4H-isoxazol-3-yl]-N-(3-formyl-4,5-dihydroisoxazol-5-yl)-2-methyl-benzamide | A | 1.18 | | 532/534 |
| A100 | N-[3-(2-chloroallyloxy)-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide | C | 2.13 | | 594/596/598 |
| A101 | 4-[(5S)-5-(3,5-dichloro-4-fluoro-phenyl)-5-(trifluoromethyl)-4H-isoxazol-3-yl]-2-methyl-N-[3-(2,2,3,3-tetrafluoropropoxy)-4,5-dihydroisoxazol-5-yl]benzamide | C | 2.12 | | 634/636 |

TABLE A-continued

Compounds according to the invention

| Cpd No | chemical name | LC-MS Method | RT (min) | [M − H]⁻ | [M + H]⁺ |
|---|---|---|---|---|---|
| A102 | 4-[(5S)-5-(3,5-dichloro-4-fluoro-phenyl)-5-(trifluoromethyl)-4H-isoxazol-3-yl]-2-methyl-N-[3-(2,2,3,3,3-pentafluoropropoxy)-4,5-dihydroisoxazol-5-yl]benzamide | C | 2.21 | | 652/654 |
| A103 | 4-[(5S)-5-(3,5-dichloro-4-fluoro-phenyl)-5-(trifluoromethyl)-4H-isoxazol-3-yl]-2-methyl-N-[3-(2,2,2-trifluoroethoxy)-4,5-dihydroisoxazol-5-yl]benzamide | C | 2.12 | | 602/604 |
| A104 | N-(3-butoxy-4,5-dihydroisoxazol-5-yl)-4-[(5S)-5-(3,5-dichloro-4-fluoro-phenyl)-5-(trifluoromethyl)-4H-isoxazol-3-yl]-2-methyl-benzamide | C | 2.18 | | 576/578 |
| A105 | 4-[(5S)-5-(3,5-dichloro-4-fluoro-phenyl)-5-(trifluoromethyl)-4H-isoxazol-3-yl]-N-[3-(dimethylamino)-4,5-dihydroisoxazol-5-yl]-2-methyl-benzamide | A | 1.11 | | 547/549/551 |
| A106 | N-(3-isopentyloxy-4,5-dihydroisoxazol-5-yl)-2-methyl-4-[(5S)-5-(3,4,5-trichlorophenyl)-5-(trifluoromethyl)-4H-isoxazol-3-yl]benzamide | C | 2.33 | | 606/608/610 |
| A107 | N-[3-(2-ethoxyethoxy)-4,5-dihydroisoxazol-5-yl]-2-methyl-4-[(5S)-5-(3,4,5-trichlorophenyl)-5-(trifluoromethyl)-4H-isoxazol-3-yl]benzamide | C | 2.09 | | 608/610/612 |
| A108 | N-[3-(4-chlorophenoxy)-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide | C | 2.23 | | 630/632/634 |
| A109 | 4-[(5S)-5-(3,5-dichloro-4-fluoro-phenyl)-5-(trifluoromethyl)-4H-isoxazol-3-yl]-2-methyl-N-[3-(2-trimethylsilylethoxy)-4,5-dihydroisoxazol-5-yl]benzamide | C | 2.35 | 618/620 [M − H]⁻ | |
| A110 | N-(3-benzyloxy-4,5-dihydroisoxazol-5-yl)-2-methyl-4-[(5S)-5-(3,4,5-trichlorophenyl)-5-(trifluoromethyl)-4H-isoxazol-3-yl]benzamide | C | 2.23 | | 626/628/630 |
| A111 | N-[3-(cyclobutylmethoxy)-4,5-dihydroisoxazol-5-yl]-2-methyl-4-[(5S)-5-(3,4,5-trichlorophenyl)-5-(trifluoromethyl)-4H-isoxazol-3-yl]benzamide | C | 2.27 | | 604/606/608 |
| A112 | 2-methyl-N-[3-(2-pyridylmethoxy)-4,5-dihydroisoxazol-5-yl]-4-[(5S)-5-(3,4,5-trichlorophenyl)-5-(trifluoromethyl)-4H-isoxazol-3-yl]benzamide | C | 2.05 | | 627/629/631 |
| A113 | 2-methyl-N-(3-pent-4-ynoxy-4,5-dihydroisoxazol-5-yl)-4-[(5S)-5-(3,4,5-trichlorophenyl)-(trifluoromethyl)-4H-isoxazol-3-yl]benzamide | C | 2.16 | | 602/604/606 |
| A114 | N-[3-[2-(dimethylamino)-2-oxo-ethoxy]-4,5-dihydroisoxazol-5-yl]-2-methyl-4-[(5S)-5-(3,4,5-trichlorophenyl)-5-(trifluoromethyl)-4H-isoxazol-3-yl]benzamide | C | 1.96 | | 621/623/625 |
| A115 | N-[3-[2-(ethylamino)-2-oxo-ethoxy]-4,5-dihydroisoxazol-5-yl]-2-methyl-4-[(5S)-5-(3,4,5-trichlorophenyl)-5-(trifluoromethyl)-4H-isoxazol-3-yl]benzamide | C | 2 | | 621/623/625 |
| A116 | N-[3-[(2E)-2-methoxyiminopropoxy]-4,5-dihydroisoxazol-5-yl]-2-methyl-4-[(5S)-5-(3,4,5-trichlorophenyl)-5-(trifluoromethyl)-4H-isoxazol-3-yl]benzamide | C | 2.15 | | 621/623/625 |
| A117 | 5-[[4-[(5S)-5-(3,5-dichloro-4-fluoro-phenyl)-5-(trifluoromethyl)-4H-isoxazol-3-yl]-2-methyl-benzoyl]amino]-4,5-dihydroisoxazole-3-carboxylic acid | A | 1.08 | | 548/550 |
| A118 | 4-[(5S)-5-(3,5-dichloro-4-fluoro-phenyl)-5-(trifluoromethyl)-4H-isoxazol-3-yl]-N-[3-[(E)-hydroxyiminomethyl]-4,5-dihydroisoxazol-5-yl]-2-methyl-benzamide | A | 1.12 | | 547/549 |
| A119 | 4-[(5S)-5-(3,5-dichloro-4-fluoro-phenyl)-5-(trifluoromethyl)-4H-isoxazol-3-yl]-N-[3-[(E)-methoxyiminomethyl]-4,5-dihydroisoxazol-5-yl]-2-methyl-benzamide | A | 1.19 | | 561/563/565 |
| A120 | 4-[(5S)-5-(3,5-dichloro-4-fluoro-phenyl)-5-(trifluoromethyl)-4H-isoxazol-3-yl]-2-methyl-N-[3-(methylamino)-4,5-dihydroisoxazol-5-yl]benzamide | A | 1.07 | | 533/535 |
| A121 | N-(3-acetonyloxy-4,5-dihydroisoxazol-5-yl)-2-methyl-4-[(5S)-5-(3,4,5-trichlorophenyl)-5-(trifluoromethyl)-4H-isoxazol-3-yl]benzamide | C | 2.07 | | 592/594/596 |

TABLE A-continued

Compounds according to the invention

| Cpd No | chemical name | LC-MS Method | RT (min) | [M − H]⁻ | [M + H]⁺ |
|---|---|---|---|---|---|
| A122 | N-[3-[(3-ethyloxetan-3-yl)methoxy]-4,5-dihydroisoxazol-5-yl]-2-methyl-4-[(5S)-5-(3,4,5-trichlorophenyl)-5-(trifluoromethyl)-4H-isoxazol-3-yl]benzamide | C | 2.11 | | 634/686/638 |
| A123 | 2-methyl-N-[3-[(3-methyloxetan-3-yl)methoxy]-4,5-dihydroisoxazol-5-yl]-4-[(5S)-5-(3,4,5-trichlorophenyl)-5-(trifluoromethyl)-4H-isoxazol-3-yl]benzamide | C | 2.1 | | 620/622/624 |
| A124 | 2-methyl-N-[3-(4-pyridylmethoxy)-4,5-dihydroisoxazol-5-yl]-4-[(5S)-5-(3,4,5-trichlorophenyl)-5-(trifluoromethyl)-4H-isoxazol-3-yl]benzamide | C | 1.9 | | 627/629/631 |
| A125 | N-(3-bromo-4,5-dihydroisoxazol-5-yl)-2-methyl-4-[(5S)-5-(3,4,5-trichlorophenyl)-5-(trifluoromethyl)-4H-isoxazol-3-yl]benzamide | A | 1.25 | | 598/600/602/604 |
| A126 | 4-[5-(3,5-dichlorophenyl)-5-(trifluoromethyl)-4H-isoxazol-3-yl]-N-(3-methoxy-4,5-dihydroisoxazol-5-yl)-2-methyl-benzamide | A | 1.16 | 514/516 | |
| A127 | N-[3-(2,2-difluoroethoxy)-4,5-dihydroisoxazol-5-yl]-2-methyl-4-[(5S)-5-(3,4,5-trichlorophenyl)-5-(trifluoromethyl)-4H-isoxazol-3-yl]benzamide | C | 2.12 | | 600/602/604 |
| A128 | 4-[(5S)-5-(3,5-dichlorophenyl)-5-(trifluoromethyl)-4H-isoxazol-3-yl]-N-[3-(2,2-difluoroethoxy)-4,5-dihydroisoxazol-5-yl]-2-methyl-benzamide | C | 2.04 | | 566/568 |
| A129 | 2-methyl-4-[(5S)-5-(3,4,5-trichlorophenyl)-5-(trifluoromethyl)-4H-isoxazol-3-yl]-N-[3-(2,2,2-trifluoroethoxy)-4,5-dihydroisoxazol-5-yl]benzamide | C | 2.2 | | 618/620/622 |
| A130 | 4-[(5S)-5-(3,5-dichlorophenyl)-5-(trifluoromethyl)-4H-isoxazol-3-yl]-2-methyl-N-[3-(2,2,2-trifluoroethoxy)-4,5-dihydroisoxazol-5-yl]benzamide | C | 2.12 | | 584/586 |
| A131 | 4-[(5S)-5-(3,5-dichloro-4-fluoro-phenyl)-5-(trifluoromethyl)-4H-isoxazol-3-yl]-N-(3-ethoxy-4,5-dihydroisoxazol-5-yl)-N-[(1R)-1-(4-methoxyphenyl)ethyl]-2-methyl-benzamide | C | 2.36 | | 682/684 |
| A132 | tert-butyl N-[4-[(5S)-5-(3,5-dichloro-4-fluoro-phenyl)-5-(trifluoromethyl)-4H-isoxazol-3-yl]-2-methyl-benzoyl]-N-(3-ethoxy-4,5-dihydroisoxazol-5-yl)carbamate | C | 2.39 | | 548/550 (M-Boc) |
| A133 | 4-[(5S)-5-(3,5-dichlorophenyl)-5-(trifluoromethyl)-4H-isoxazol-3-yl]-N-(3-ethoxy-4,5-dihydroisoxazol-5-yl)-N-formyl-2-methyl-benzamide | C | 2.15 | | 558560/562 |
| A134 | 4-[(5S)-5-(3,5-dichlorophenyl)-5-(trifluoromethyl)-4H-isoxazol-3-yl]-N-formyl-N-(3-methoxy-4,5-dihydroisoxazol-5-yl)-2-methyl-benzamide | C | 2.07 | | 544/546 |
| A135 | [5-[[2-methyl-4-[(5S)-5-(3,4,5-trichlorophenyl)-5-(trifluoromethyl)-4H-isoxazol-3-yl]benzoyl]amino]-4,5-dihydroisoxazol-3-yl]methanesulfonate | A | 1.23 | | 612/614/616 |
| A136 | 4-[(5S)-5-(3,5-dichlorophenyl)-5-(trifluoromethyl)-4H-isoxazol-3-yl]-2-methyl-N-[3-(trifluoromethyl)-4,5-dihydroisoxazol-5-yl]benzamide | B | 1.25 | 552/554/556 | |
| A137 | 4-[(5S)-5-(3,5-dichlorophenyl)-5-(trifluoromethyl)-4H-isoxazol-3-yl]-N-(3-ethyl-4,5-dihydroisoxazol-5-yl)-2-methyl-benzamide | B | 1.19 | 512/514/516 | |
| A138 | 4-[(5S)-5-(3,5-dichlorophenyl)-5-(trifluoromethyl)-4H-isoxazol-3-yl]-N-formyl-2-methyl-N-[3-(trifluoromethyl)-4,5-dihydroisoxazol-5-yl]benzamide | B | 1.29 | | 582/584 |
| A139 | 4-[(5S)-5-(3,5-dichlorophenyl)-5-(trifluoromethyl)-4H-isoxazol-3-yl]-N-(3-ethyl-4,5-dihydroisoxazol-5-yl)-N-formyl-2-methyl-benzamide | B | 1.24 | 540/542/544 | |
| A140 | 4-[(5S)-5-(3,5-dichlorophenyl)-5-(trifluoromethyl)-4H-isoxazol-3-yl]-N-formyl-2-methyl-N-(3-methyl-4,5-dihydroisoxazol-5-yl)benzamide | B | 1.22 | 526/528 | |
| A141 | 4-[(5S)-5-(3,5-dichlorophenyl)-5-(trifluoromethyl)-4H-isoxazol-3-yl]-2-methyl-N-(3-methyl-4,5-dihydroisoxazol-5-yl)benzamide | B | 1.15 | 498/500/502 | |

TABLE A-continued

Compounds according to the invention

| Cpd No | chemical name | LC-MS Method | RT (min) | [M − H]⁻ | [M + H]⁺ |
|---|---|---|---|---|---|
| A142 | N-(3-bromo-4,5-dihydroisoxazol-5-yl)-4-[(5S)-5-[3-chloro-5-(trifluoromethyl)phenyl]-5-(trifluoromethyl)-4H-isoxazol-3-yl]-N-formyl-2-methyl-benzamide | B | 1.24 | 596/598/600 (M-CHO) | |
| A143 | N-[3-[(Z)-1-aminoethylideneamino]oxy-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide | C | 1.82 | | 576/578/580 |
| A144 | (3E)-5-[[4-[(5S)-5-(3,5-dichloro-4-fluoro-phenyl)-5-(trifluoromethyl)-4H-isoxazol-3-yl]-2-methyl-benzoyl]-formyl-amino]-N-hydroxy-4,5-dihydroisoxazole-3-carboximidoyl bromide | * | * | * | * |
| A145 | N-(3-cyano-4,5-dihydroisoxazol-5-yl)-2-methyl-4-[(5S)-5-(3,4,5-trichlorophenyl)-5-(trifluoromethyl)-4H-isoxazol-3-yl]benzamide | * | * | * | * |
| A146 | N-[(5R)-3-bromo-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide | * | * | * | * |
| A147 | N-[(5S)-3-bromo-4,5-dihydroisoxazol-5-yl]-4-[(5S)-5-(3,5-dichloro-4-fluoro-phenyl)-5-(trifluoromethyl)-4H-isoxazol-3-yl]-2-methyl-benzamide | * | * | * | * |
| A148 | N-[(5S)-3-methoxy-4,5-dihydroisoxazol-5-yl]-2-methyl-4-[(5S)-5-(3,4,5-trichlorophenyl)-5-(trifluoromethyl)-4H-isoxazol-3-yl]benzamide | * | * | * | * |
| A149 | N-[(5R)-3-methoxy-4,5-dihydroisoxazol-5-yl]-2-methyl-4-[(5S)-5-(3,4,5-trichlorophenyl)-5-(trifluoromethyl)-4H-isoxazol-3-yl]benzamide | * | * | * | * |
| A150 | 4-[(5S)-5-(3,5-dichloro-4-fluoro-phenyl)-5-(trifluoromethyl)-4H-isoxazol-3-yl]-N-[(5S)-3-m ethoxy-4,5-dihydroisoxazol-5-yl]-2-methyl-benzamide | * | * | * | * |
| A151 | 4-[(5S)-5-(3,5-dichloro-4-fluoro-phenyl)-5-(trifluoromethyl)-4H-isoxazol-3-yl]-N-[(5R)-3-methoxy-4,5-dihydroisoxazol-5-yl]-2-methyl-benzamide | * | * | * | * |
| A152 | tert-butyl N-[(5S)-3-methoxy-4,5-dihydroisoxazol-5-yl]-N-[2-methyl-4-[(5S)-5-(3,4,5-trichlorophenyl)-5-(trifluoromethyl)-4H-isoxazol-3-yl]benzoyl]carbamate | * | * | * | * |
| A153 | tert-butyl N-[(5R)-3-methoxy-4,5-dihydroisoxazol-5-yl]-N-[2-methyl-4-[(5S)-5-(3,4,5-trichlorophenyl)-5-(trifluoromethyl)-4H-isoxazol-3-yl]benzoyl]carbamate | * | * | * | * |
| A154 | 4-[(5S)-5-(3,5-dichlorophenyl)-5-(trifluoromethyl)-4H-isoxazol-3-yl]-2-methyl-N-[(5S)-3-(trifluoromethyl)-4,5-dihydroisoxazol-5-yl]benzamide | * | * | * | * |
| A155 | 4-[(5S)-5-(3,5-dichlorophenyl)-5-(trifluoromethyl)-4H-isoxazol-3-yl]-2-methyl-N-[(5R)-3-(trifluoromethyl)-4,5-dihydroisoxazol-5-yl]benzamide | * | * | * | * |
| A156 | 4-[(5S)-5-(3,5-dichlorophenyl)-5-(trifluoromethyl)-4H-isoxazol-3-yl]-2-methyl-N-[(5S)-3-(2,2,2-trifluoroethoxy)-4,5-dihydroisoxazol-5-yl]benzamide | * | * | * | * |
| A157 | 4-[(5S)-5-(3,5-dichlorophenyl)-5-(trifluoromethyl)-4H-isoxazol-3-yl]-2-methyl-N-[(5R)-3-(2,2,2-trifluoroethoxy)-4,5-dihydroisoxazol-5-yl]benzamide | * | * | * | * |
| A158 | 4-[(5S)-5-(3,5-dichlorophenyl)-5-(trifluoromethyl)-4H-isoxazol-3-yl]-N-[(5S)-3-ethoxy-4,5-dihydroisoxazol-5-yl]-2-methyl-benzamide | * | * | * | * |
| A159 | 4-[(5S)-5-(3,5-dichlorophenyl)-5-(trifluoromethyl)-4H-isoxazol-3-yl]-N-[(5R)-3-ethoxy-4,5-dihydroisoxazol-5-yl]-2-methyl-benzamide | * | * | * | * |

*see NMR/chiral HPLC information in the experimental section

Compound A144: mixture of isomers, 1H NMR (600 MHz, CDCL3) ä ppm 2.40 (s, 3 H) 2.41 (s, 3 H) 3.54 (dd, J = 17.8, 11.3 Hz, 1 H) 3.61 (dd, J = 17.8, 5.0 Hz, 1 H) 3.71 (d, J = 17.2 Hz, 2 H) 3.81 (dd, J = 18.2, 10.4 Hz, 1 H) 3.84 (dd, J = 18.2, 5.6 Hz, 1 H) 4.10 (d, J = 17.2 Hz, 2 H) 7.01 (br dd, J = 10.9, 5.3 Hz, 1 H) 7.02 (dd, J = 10.9, 5.4 Hz, 1 H) 7.40 (br d, J = 7.9 Hz, 1 H) 7.40 (d, J = 8.1 Hz, 1 H) 7.59 (d, J = 6.0 Hz, 4 H) 7.60-7.64 (m, 4 H) 8.65 (s, 1 H) 8.65 (s, 1 H) 8.78 (d, J = 2.5 Hz, 1 H) 9.12 (br s, 1 H)

Biological Examples

These Examples illustrate the pesticidal/insecticidal properties of compounds of formula (I).

Tests were performed as follows:

*Spodoptera littoralis* (Egyptian Cotton Leaf Worm)

Cotton leaf discs were placed on agar in 24-well microtiter plates and sprayed with aqueous test solutions prepared from 10'000 ppm DMSO stock solutions. After drying the leaf discs were infested with five L1 larvae. The samples were assessed for mortality, anti-feedant effect, and growth inhibition in comparison to untreated samples 3 days after infestation. Control of *Spodoptera littoralis* by a test sample is when at least one of mortality, anti-feedant effect, and growth inhibition is higher than the untreated sample. The following compounds resulted in at least 80% control at an application rate of 200 ppm:

A001; A002; A003; A004; A005; A006; A007; A008; A009; A010; A011; A012; A013; A014; A015; A016; A017; A018; A020; A021; A022; A023; A024; A025; A026; A027; A028; A029; A030; A031; A032; A033; A034; A035; A036; A037; A038; A039; A040; A041; A042; A043; A044; A045; A046; A047; A048; A049; A050; A051; A052; A053; A054; A055; A056; A057; A058; A059; A060; A061; A062; A063; A064; A065; A066; A067; A068; A069; A070; A071; A072; A073; A074; A075; A076; A077; A078; A079; A080; A081; A082; A083; A084; A085; A086; A087; A088; A089; A090; A091; A092; A093; A094; A095; A096; A097; A098; A099; A100; A101; A102; A103; A104; A105; A106; A107; A108; A109; A110; A111; A112; A113; A114; A115; A116; A117; A118; A119; A120; A121; A122; A123; A124; A125; A126; A127; A128; A129; A130; A131; A132; A133; A134; A135; A136; A137; A138; A139; A140; A141; A142; A143; A144; A145; A146; A147; A148; A149; A150; A151; A152; A153; A154; A155; A156; A157; A158; A159.

*Plutella xylostella* (Diamond Back Moth):

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation. The following compounds gave an effect of at least 80% in at least one of the two categories (mortality or growth inhibition) at an application rate of 200 ppm:

A001; A002; A003; A004; A005; A006; A007; A008; A009; A010; A011; A012; A013; A014; A015; A016; A017; A018; A020; A021; A022; A023; A024; A025; A026; A027; A028; A029; A030; A031; A032; A033; A034; A035; A036; A037; A038; A039; A040; A041; A042; A043; A044; A045; A046; A047; A048; A049; A050; A051; A052; A053; A054; A055; A056; A057; A058; A059; A060; A061; A062; A063; A064; A065; A066; A067; A068; A069; A070; A071; A072; A073; A074; A075; A076; A077; A078; A079; A080; A081; A082; A083; A084; A085; A086; A087; A088; A089; A090; A091; A092; A093; A094; A095; A096; A097; A098; A099; A100; A101; A102; A103; A104; A105; A106; A107; A108; A109; A110; A111; A112; A113; A114; A115; A116; A117; A118; A119; A120; A121; A122; A123; A124; A125; A126; A127; A128; A129; A130; A131; A132; A133; A134; A135; A136; A137; A138; A139; A140; A141; A142; A143; A144; A145; A146; A147; A148; A149; A150; A151; A152; A153; A154; A155; A156; A157; A158; A159.

*Diabrotica* Balteata, (Corn Root Worm)

Maize sprouts, placed on an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation. The following compounds gave an effect of at least 80% in at least one of the two categories (mortality or growth inhibition) at an application rate of 200 ppm:

A001; A002; A003; A004; A005; A006; A007; A008; A009; A010; A011; A012; A013; A014; A015; A016; A017; A018; A020; A021; A022; A023; A024; A025; A026; A027; A028; A029; A030; A031; A032; A033; A034; A035; A036; A037; A038; A039; A040; A041; A042; A043; A044; A045; A046; A047; A048; A049; A050; A051; A052; A053; A054; A055; A056; A057; A058; A059; A060; A061; A062; A063; A064; A065; A066; A067; A068; A069; A070; A071; A072; A073; A074; A075; A076; A077; A078; A079; A080; A081; A082; A083; A084; A085; A086; A087; A088; A089; A090; A091; A092; A093; A094; A095; A096; A097; A098; A099; A100; A101; A102; A103; A104; A105; A106; A107; A108; A109; A110; A111; A112; A113; A115; A116; A117; A118; A119; A120; A121; A122; A123; A124; A125; A126; A127; A128; A129; A130; A131; A132; A133; A134; A135; A136; A137; A138; A139; A140; A141; A142; A143; A144; A145; A146; A147; A148; A149; A150; A151; A152; A153; A154; A155; A156; A157; A158; A159.

*Thrips tabaci* (Onion *Thrips*):

Sunflower leaf discs were placed on agar in 24-well microtiter plates and sprayed with aqueous test solutions prepared from 10'000 ppm DMSO stock solutions. After drying the leaf discs were infested with a *thrips* population of mixed ages. The samples were assessed for mortality 6 days after infestation. The following compounds resulted in at least 80% mortality at an application rate of 200 ppm:

A001; A002; A003; A004; A005; A006; A007; A008; A009; A010; A011; A012; A013; A014; A015; A016; A017; A018; A020; A021; A022; A023; A024; A025; A026; A027; A028; A029; A030; A031; A032; A033; A034; A035; A036; A037; A038; A039; A040; A041; A042; A043; A044; A045; A046; A047; A048; A049; A050; A051; A052; A053; A054; A055; A056; A057; A058; A059; A060; A061; A062; A063; A064; A065; A066; A067; A068; A069; A070; A071; A072; A073; A074; A075; A076; A077; A078; A079; A080; A081; A082; A083; A084; A085; A086; A087; A088; A089; A090; A091; A092; A093; A094; A095; A096; A097; A098; A099; A100; A101; A102; A103; A104; A105; A106; A107; A108; A109; A110; A111; A112; A113; A114; A115; A116; A117; A118; A119; A120; A121; A122; A123; A124; A125; A126; A127; A128; A129; A130; A131; A132; A133; A134; A135; A136; A137; A138; A139; A140; A141; A142; A143; A144; A145; A146; A147; A148; A149; A150; A151; A152; A153; A154; A155; A156; A157; A158; A159.

*Tetranychus urticae* (Two-Spotted Spider Mite):

Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation. The following compounds resulted in at least 80% mortality at an application rate of 200 ppm:

A001; A002; A003; A004; A005; A007; A008; A009; A010; A011; A012; A013; A014; A015; A016; A017; A018; A020; A021; A022; A023; A024; A025; A026; A027; A028; A029; A030; A031; A032; A033; A034; A035; A036; A037; A038; A039; A040; A041; A042; A043; A044; A045; A046; A047; A048; A049; A050; A051; A052; A053; A054; A055; A056; A057; A058; A059; A060; A061; A062; A063; A064; A065; A066; A067; A068; A069; A070; A071; A072; A073;

A074; A075; A076; A077; A078; A079; A080; A081; A082; A083; A084; A085; A086; A087; A088; A089; A090; A091; A092; A093; A094; A095; A099; A100; A101; A102; A103; A104; A105; A106; A107; A108; A109; A110; A111; A112; A113; A114; A115; A116; A117; A118; A119; A120; A121; A122; A123; A124; A125; A126; A127; A128; A129; A130; A131; A132; A133; A134; A135; A136; A137; A138; A139; A140; A141; A142; A143; A144; A145; A146; A147; A148; A149; A150; A151; A152; A153; A154; A155; A156; A157; A158; A159.

*Myzus persicae* (Green Peach Aphid):

Sunflower leaf discs were placed on agar in a 24-well microtiter plate and sprayed with test solutions at an application rate of 200 ppm. After drying, the leaf discs were infested with an aphid population of mixed ages. After an incubation period of 6 days after treatment, samples were checked for mortality. The following compounds gave at least 80% mortality of *Myzus persicae*:

A001; A002; A003; A004; A005; A008; A009; A010; A011; A012; A013; A014; A015; A016; A017; A018; A021; A022; A023; A024; A025; A026; A027; A028; A029; A030; A031; A032; A033; A034; A035; A036; A037; A038; A039; A040; A041; A042; A043; A044; A045; A046; A047; A049; A050; A051; A052; A054; A055; A056; A057; A058; A059; A060; A061; A062; A063; A064; A065; A066; A069; A070; A071; A072; A073; A074; A075; A076; A077; A078; A079; A080; A081; A082; A083; A084; A085; A086; A087; A089; A090; A091; A099; A100; A101; A102; A103; A104; A105; A106; A107; A108; A109; A110; A111; A112; A113; A114; A115; A116; A119; A120; A121; A122; A123; A124; A125; A126; A127; A128; A129; A130; A132; A133; A134; A136; A137; A138; A139; A140; A141; A142; A144; A145; A147; A148; A149; A150; A154; A155; A156; A158.

The invention claimed is:

1. A compound of formula (I),

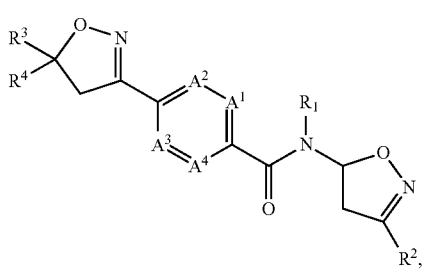

wherein $A^1$, $A^2$, $A^3$ and $A^4$ are, independently of one another, C—H, C—$R^5$ or N;

$R^1$ is hydrogen, formyl, $C_1$-$C_8$alkyl, $C_1$-$C_8$alkylcarbonyl-, $C_1$-$C_8$alkoxy, $C_1$-$C_8$alkoxy-$C_1$-$C_8$alkyl or $C_1$-$C_8$alkoxycarbonyl, phenyl-$C_1$-$C_8$alkoxycarbonyl, phenyl-$C_1$-$C_4$alkyl, or phenyl-$C_1$-$C_4$alkyl wherein the phenyl moiety is substituted by one to three $R^7$;

$R^2$ is hydrogen, halogen, cyano, —NH($R^8$), —N($R^8$)($R^9$), —O$R^{10}$, —S$R^{10}$, —S(O)$R^{10}$, —S(O)$_2R^{10}$, CO$R^M$, COO$R^{10}$, $C_1$-$C_8$alkyl or $C_1$-$C_8$alkyl substituted by one to three $R^{6a}$, $C_1$-$C_8$haloalkyl or $C_1$-$C_8$haloalkyl substituted by one to three $R^{6a}$, $C_3$-$C_8$cycloalkyl or $C_3$-$C_8$cycloalkyl substituted by one to three $R^{6b}$, $C_3$-$C_8$cycloalkyl where one carbon atom is replaced by O, S, S(O) or SO$_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, or $C_3$-$C_8$cycloalkyl-$C_1$-$C_8$haloalkyl, $C_2$-$C_8$alkenyl or $C_2$-$C_8$alkenyl substituted by one to three $R^{6a}$, $C_2$-$C_8$haloalkenyl or $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, or 5-6 membered heteroaryl-$C_1$-$C_4$alkyl or 5-6 membered heteroaryl-$C_1$-$C_4$alkyl wherein the heteroaryl moiety is substituted by one to three $R^7$;

$R^3$ is $C_1$-$C_8$haloalkyl;

$R^4$ is phenyl or phenyl substituted by one to three $R^{6b}$ or pyridine or pyridine substituted by one to three $R^{6b}$;

each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —CH=CH—CH=CH— bridge or a —N=CH—CH=CH— bridge;

each $R^{6a}$ is independently halogen, cyano, nitro, amino, hydroxy, oxo, $C_1$-$C_8$alkylamino, hydroxyimino, $C_1$-$C_8$alkyloxyimino, di-$C_1$-$C_8$alkylamino, $C_1$-$C_8$alkoxy, acetyloxy, formyloxy, $C_1$-$C_8$halo alkoxy, $C_1$-$C_4$alkylthio or tri-($C_1$-$C_4$alkyl)silyl;

each $R^{6b}$ is independently halogen, cyano, nitro, $C_1$-$C_8$alkyl, $C_1$-$C_8$haloalkyl, amino, $C_1$-$C_8$alkylamino, di-$C_1$-$C_8$alkylamino, hydroxyl, $C_1$-$C_4$alkylthio, $C_1$-$C_8$alkoxy or $C_1$-$C_8$haloalkoxy;

each $R^7$ is independently halogen, cyano, nitro, $C_1$-$C_8$alkyl, $C_1$-$C_8$haloalkyl, $C_1$-$C_8$alkoxy, or $C_1$-$C_8$haloalkoxy;

$R^8$ and $R^9$ are independently hydrogen, cyano, $C_1$-$C_8$alkyl or $C_1$-$C_8$alkyl substituted by one to three $R^{6a}$, $C_1$-$C_8$alkoxy, $C_1$-$C_8$haloalkoxy, $C_1$-$C_8$haloalkoxy substituted by one to three $R^{6a}$, $C_1$-$C_8$alkoxy substituted by one to three $R^{6a}$, $C_1$-$C_8$haloalkyl or $C_1$-$C_8$haloalkyl substituted by one to three $R^{6a}$, $C_3$-$C_8$cycloalkyl or $C_3$-$C_8$cycloalkyl substituted by one to three $R^{6b}$, $C_3$-$C_8$cycloalkyl where one carbon atom is replaced by O, S, S(O) or SO$_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, or $C_3$-$C_8$cycloalkyl-$C_1$-$C_8$haloalkyl, $C_2$-$C_8$alkenyl or $C_2$-$C_8$alkenyl substituted by one to three $R^{6a}$, $C_2$-$C_8$haloalkenyl or $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl or 5-6 membered heteroaryl-$C_1$-$C_4$alkyl wherein the heteroaryl moiety is substituted by one to three $R^7$, or $R^8$ and $R^9$ together with the nitrogen atom can be linked through a $C_3$-$C_8$alkylene chain, a $C_3$-$C_8$alkylene chain substituted by one to three $R^{6b}$ or a $C_3$-$C_8$alkylene chain, where one carbon atom is replaced by O, S, S(O) or SO$_2$; and $R^{10}$ is hydrogen, cyano, $C_1$-$C_8$alkyl or $C_1$-$C_8$alkyl substituted by one to three $R^{6a}$, $C_1$-$C_8$haloalkyl or $C_1$-$C_8$haloalkyl substituted by one to three $R^{6a}$, $C_3$-$C_8$cycloalkyl or $C_3$-$C_8$cycloalkyl substituted by one to three $R^{6b}$, $C_3$-$C_8$cycloalkyl where one carbon atom is replaced by O, S, S(O) or SO$_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, or C$_3$-C$_8$cycloalkyl-C$_1$-C$_8$haloalkyl, C$_2$-C$_8$alkenyl or C$_2$-C$_8$alkenyl substituted by one to three R$^{6a}$, C$_2$-C$_8$haloalkenyl or C$_2$-C$_8$haloalkenyl substituted by one to three R$^{6a}$, C$_2$-C$_8$alkynyl, C$_2$-C$_8$haloalkynyl, phenyl, phenyl substituted by one to three R$^7$, phenyl-C$_1$-C$_4$alkyl, phenyl-C$_1$-C$_4$alkyl wherein the phenyl moiety is substituted by one to three R$^7$, 5-6 membered heteroaryl, 5-6 membered heteroaryl substituted by one to three R$^7$, or 5-6 membered heteroaryl-C$_1$-C$_4$alkyl or 5-6 membered heteroaryl-C$_1$-C$_4$alkyl wherein the heteroaryl moiety is substituted by one to three R$^7$; or an agrochemically acceptable salt, stereoisomer, enantiomer, tautomer and N-oxide thereof.

2. The compound of claim 1, wherein A$^1$ is C—R$^5$; A$^2$ is C—H; A$^3$ is C—H; and A$^4$ is C—H, wherein R$^5$ is halogen, cyano, nitro, C$_1$-C$_8$alkyl, C$_3$-C$_8$cycloalkyl, C$_1$-C$_8$haloalkyl, or C$_2$-C$_8$alkenyl.

3. The compound of claim 1, wherein R$^2$ is halogen, C$_1$-C$_4$alkyl, C$_3$-C$_5$cycloalkyl, C$_1$-C$_4$haloalkyl, C$_1$-C$_4$alkoxy, C$_1$-C$_4$haloalkoxy, di-C$_1$-C$_4$alkylamino, C$_1$-C$_4$alkylthio, or C$_1$-C$_4$alkyloxycarbonyl.

4. The compound of claim 1, wherein R$^1$ is hydrogen, formyl, C$_1$-C$_8$alkyl, C$_1$-C$_8$alkylcarbonyl- or C$_1$-C$_8$alkoxycarbonyl-.

5. The compound of claim 1, wherein R$^3$ is C$_1$-C$_4$haloalkyl.

6. The compound of claim 1, wherein

R$^4$ is phenyl or phenyl substituted by one to three R$^{6b}$; and each R$^{6b}$ independently is halogen, cyano, nitro, C$_1$-C$_4$alkyl, C$_1$-C$_4$haloalkyl, C$_1$-C$_4$alkoxy, or C$_1$-C$_4$haloalkoxy.

7. The compound of claim 6, wherein R$^{6b}$ is bromo, chloro, fluoro, cyano, nitro, methyl, ethyl, trifluoromethyl, methoxy, difluoromethoxy, or trifluoromethoxy.

8. The compound of claim 1, wherein at least two of A$^1$, A$^2$, A$^3$ and A$^4$ is C—H.

9. The compound of claim 1, wherein R$^2$ is halogen, cyano, —NH(R$^8$), —N(R$^8$)(R$^9$), —OR$^{10}$, —SR$^{10}$, —S(O)R$^{10}$, —S(O)$_2$R$^{10}$, COR$^{10}$, COOR$^{10}$,C$_1$-C$_8$alkyl or C$_1$-C$_8$alkyl substituted by one to three R$^{6a}$, C$_1$-C$_8$haloalkyl or C$_1$-C$_8$haloalkyl substituted by one to three R$^{6a}$, C$_3$-C$_8$cycloalkyl or C$_3$-C$_8$cycloalkyl substituted by one to three R$^{6b}$, C$_3$-C$_8$cycloalkyl where one carbon atom is replaced by O, S, S(O) or SO$_2$, or C$_3$-C$_8$cycloalkyl-C$_1$-C$_8$alkyl, C$_3$-C$_8$cycloalkyl-C$_1$-C$_8$alkyl where one carbon atom in the cycloalkyl group is replaced by O, S, S(O) or SO$_2$, or C$_3$-C$_8$cycloalkyl-C$_1$-C$_8$haloalkyl, C$_2$-C$_8$alkenyl or C$_2$-C$_8$alkenyl substituted by one to three R$^{6a}$, C$_2$-C$_8$haloalkenyl or C$_2$-C$_8$haloalkenyl substituted by one to three R$^{6a}$, C$_2$-C$_8$alkynyl, C$_2$-C$_8$haloalkynyl, phenyl, phenyl substituted by one to three R$^7$, phenyl-C$_1$-C$_4$alkyl, phenyl-C$_1$-C$_4$alkyl wherein the phenyl moiety is substituted by one to three R$^7$, 5-6 membered heteroaryl, 5-6 membered heteroaryl substituted by one to three R$^7$, or 5-6 membered heteroaryl-C$_1$-C$_4$alkyl or 5-6 membered heteroaryl-C$_1$-C$_4$alkyl wherein the heteroaryl moiety is substituted by one to three R$^7$.

10. The compound of claim 1, wherein R$^2$ is halogen, cyano, —NH(R$^8$), —N(R$^8$)(R$^9$), —OR$^{10}$, —SR$^{10}$, —S(O)R$^{10}$, —S(O)$_2$R$^{10}$, COR$^{10}$, COOR$^{10}$, C$_8$haloalkyl or C$_1$-C$_8$haloalkyl substituted by one to three R$^{6a}$, C$_3$-C$_8$cycloalkyl or C$_3$-C$_8$cycloalkyl substituted by one to three R$^{6b}$, C$_3$-C$_8$cycloalkyl where one carbon atom is replaced by O, S, S(O) or SO$_2$, or C$_3$-C$_8$cycloalkyl-C$_1$-C$_8$alkyl, C$_3$-C$_8$cycloalkyl-C$_1$-C$_8$alkyl where one carbon atom in the cycloalkyl group is replaced by O, S, S(O) or SO$_2$, or C$_3$-C$_8$cycloalkyl-C$_1$-C$_8$haloalkyl, C$_2$-C$_8$alkenyl or C$_2$-C$_8$alkenyl substituted by one to three R$^{6a}$, C$_2$-C$_8$haloalkenyl or C$_2$-C$_8$haloalkenyl substituted by one to three R$^{6a}$, C$_2$-C$_8$alkynyl, C$_2$-C$_8$haloalkynyl, phenyl, phenyl substituted by one to three R$^7$, phenyl-C$_1$-C$_4$alkyl, phenyl-C$_1$-C$_4$alkyl wherein the phenyl moiety is substituted by one to three R$^7$, 5-6 membered heteroaryl, 5-6 membered heteroaryl substituted by one to three R$^7$, or 5-6 membered heteroaryl-C$_1$-C$_4$alkyl or 5-6 membered heteroaryl-C$_1$-C$_4$alkyl wherein the heteroaryl moiety is substituted by one to three R$^7$.

11. The compound of claim 1, wherein R$^2$ is —NH(R$^8$), —N(R$^8$)(R$^9$), OR$^{10}$, SR$^{10}$, —S(O)R$^{10}$, —S(O)$_2$R$^{10}$, COR$^{10}$, COOR$^{10}$, C$_8$alkyl or C$_3$-C$_8$alkyl substituted by one to three R$^{6a}$, C$_3$-C$_8$haloalkyl or C$_3$-C$_8$haloalkyl substituted by one to three R$^{6a}$, C$_3$-C$_8$cycloalkyl or C$_3$-C$_8$cycloalkyl substituted by one to three R$^{6b}$, C$_3$-C$_8$cycloalkyl where one carbon atom is replaced by O, S, S(O) or SO$_2$, or C$_3$-C$_8$cycloalkyl-C$_1$-C$_8$alkyl, C$_3$-C$_8$cycloalkyl-C$_1$-C$_8$alkyl where one carbon atom in the cycloalkyl group is replaced by O, S, S(O) or SO$_2$, or C$_3$-C$_8$cycloalkyl-C$_1$-C$_8$haloalkyl, C$_2$-C$_8$alkenyl or C$_2$-C$_8$alkenyl substituted by one to three R$^{6a}$, C$_2$-C$_8$haloalkenyl or C$_2$-C$_8$haloalkenyl substituted by one to three R$^{6a}$, C$_2$-C$_8$alkynyl, C$_2$-C$_8$haloalkynyl, phenyl, phenyl substituted by one to three R$^7$, phenyl-C$_1$-C$_4$alkyl, phenyl-C$_1$-C$_4$alkyl wherein the phenyl moiety is substituted by one to three R$^7$, 5-6 membered heteroaryl, 5-6 membered heteroaryl substituted by one to three R$^7$, or 5-6 membered heteroaryl-C$_1$-C$_4$alkyl or 5-6 membered heteroaryl-C$_1$-C$_4$alkyl wherein the heteroaryl moiety is substituted by one to three R$^7$.

12. The compound of claim 1 represented by the compound of formula (Ib)

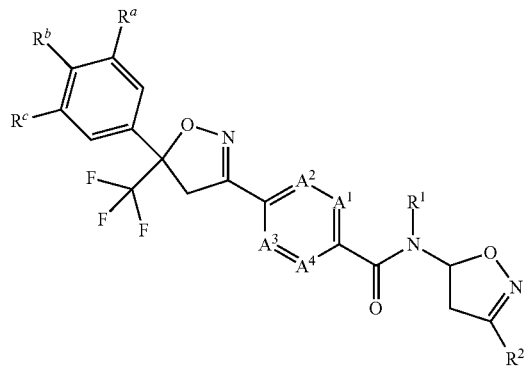

(Ib)

wherein

A$^1$ is C—R$^5$ and A$^2$, A$^3$ and A$^4$ are C—H;

R$^1$ is hydrogen, formyl, phenyl-C$_1$-C$_4$alkyl, phenyl-C$_1$-C$_4$alkyl wherein the phenyl moiety is substituted by one to three R$^7$;

R$^2$ is hydrogen, halogen, —NH(R$^8$), —N(R$^8$)(R$^9$), —OR$^{10}$, —SR$^{10}$, —S(O)R$^{10}$, —S(O)$_2$R$^{10}$, COR$^{10}$, COOR$^{10}$, C$_1$-C$_8$haloalkyl or C$_1$-C$_8$haloalkyl substituted by one to three R$^{ha}$, or C$_3$-C$_8$cycloalkyl or C$_3$-C$_8$cycloalkyl substituted by one to three R$^{6b}$;

R$^5$ is independently halogen, C$_1$-C$_8$alkyl;

each R$^{6a}$ is independently hydroxy, oxo, hydroxyimino, C$_1$-C$_8$alkyloxyimino, C$_1$-C$_8$alkoxy, acetyloxy, formyloxy or tri-(C$_1$-C$_4$alkyl)silyl;

each $R^{6b}$ is halogen, $C_1$-$C_8$haloalkyl, or $C_1$-$C_4$alkylthio;

each $R^7$ is independently halogen, $C_1$-$C_8$alkoxy, or $C_1$-$C_8$haloalkoxy;

$R^8$ and $R^9$ are independently hydrogen, $C_1$-$C_8$alkyl or $C_1$-$C_8$alkyl substituted by one to three $R^{6a}$;

$R^{10}$ is hydrogen, $C_1$-$C_8$alkyl or $C_1$-$C_8$alkyl substituted by one to three $R^{6a}$, $C_1$-$C_8$haloalkyl or $C_1$-$C_8$haloalkyl substituted by one to three $R^{6a}$, $C_3$-$C_8$cycloalkyl or $C_3$-$C_8$cycloalkyl substituted by one to three $R^{6b}$, $C_3$-$C_8$cycloalkyl where one carbon atom is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_3$-$C_8$cycloalkyl-$C_1$-$C_8$haloalkyl, $C_2$-$C_8$alkenyl or $C_2$-$C_8$alkenyl substituted by one to three $R^{6a}$, $C_2$-$C_8$haloalkenyl or $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl or 5-6 membered heteroaryl-$C_1$-$C_4$alkyl wherein the heteroaryl moiety is substituted by one to three $R^7$.

13. A pesticidal composition, which comprises at least one compound of formula (I) according to claim 1 or, where appropriate, a tautomer thereof, in each case in free form or in agrochemically utilizable salt form, as active ingredient.

14. A method for controlling pests, which comprises applying a composition according to claim 13 to the pests or their environment with the exception of a method for treatment of the human or animal body by surgery or therapy and diagnostic methods practised on the human or animal body.

15. A method for the protection of plant propagation material from the attack by pests, which comprises treating the propagation material or the site, where the propagation material is planted, with a composition according to claim 13.

16. Plant propagation material treated with the pesticidal composition according to claim 13.

* * * * *